United States Patent [19]
Ohnishi et al.

[11] Patent Number: 6,015,508
[45] Date of Patent: Jan. 18, 2000

[54] LIQUID CRYSTALLINE COMPOUNDS CONTAINING HYDROCARBON GROUPS, LIQUID CRYSTALLINE COMPOSITIONS, AND LIQUID CRYSTAL DISPLAY ELEMENTS

[75] Inventors: Noriyuki Ohnishi, Ibaraki; Hiroyuki Takeuchi; Kazutoshi Miyazawa, both of Chiba; Norihisa Hachiya, Saitama; Etsuo Nakagawa, Chiba, all of Japan

[73] Assignee: Chisso Corporation, Ohsaka-fu, Japan

[21] Appl. No.: 09/030,835

[22] Filed: Feb. 26, 1998

[30] Foreign Application Priority Data

Feb. 28, 1997 [JP] Japan ................. 9-062373

[51] Int. Cl.$^7$ .................... C09K 19/30; C09K 19/12; C09K 19/34; C07C 15/12
[52] U.S. Cl. .................. 252/299.63; 252/299.66; 252/299.61; 568/626; 568/647; 585/25
[58] Field of Search ............. 252/299.63, 299.66, 252/299.61; 585/25; 568/626, 647

[56] References Cited

U.S. PATENT DOCUMENTS

| | | | |
|---|---|---|---|
| 5,154,851 | 10/1992 | Goto et al. ............ | 252/299.63 |
| 5,308,537 | 5/1994 | Coates et al. ............ | 252/299.6 |
| 5,328,637 | 7/1994 | Buchecker et al. ............ | 252/299.6 |
| 5,370,819 | 12/1994 | Fujita et al. ............ | 252/299.01 |
| 5,449,810 | 9/1995 | Fujita et al. ............ | 558/425 |
| 5,609,791 | 3/1997 | Fujita et al. ............ | 252/299.63 |
| 5,635,108 | 6/1997 | Fujita et al. ............ | 252/299.63 |
| 5,662,830 | 9/1997 | Fujita et al. ............ | 252/299.63 |
| 5,695,681 | 12/1997 | Siemensmeyer et al. ........ | 252/299.01 |
| 5,766,366 | 7/1998 | Tomi et al. ............ | 252/299.63 |
| 5,776,367 | 7/1998 | Matsui et al. ............ | 252/299.63 |
| 5,807,500 | 9/1998 | Bremer et al. ............ | 252/299.66 |
| 5,833,879 | 11/1998 | Miyazawa et al. ........ | 252/299.63 |

*Primary Examiner*—C. H. Kelly
*Attorney, Agent, or Firm*—Wenderoth, Lind & Ponack, L.L.P.

[57] ABSTRACT

Disclosed are (A) a liquid crystalline compound of the general formula:

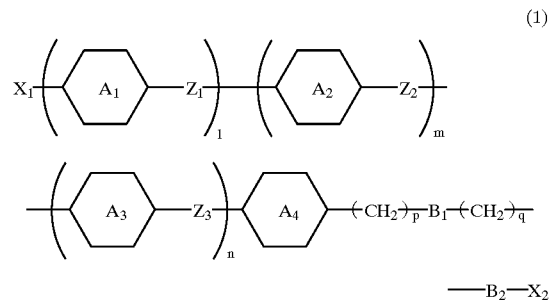

(1)

wherein $X_1$ stands for a hydrogen atom, cyano group, a halogen atom, or an alkyl group with 1–20 carbon atoms, and one or more methylene groups in the alkyl group may be replaced by —CH=CH—, —C≡C—, or oxygen atoms and one or more hydrogen atoms may be substituted by halogen atoms; $X_2$ stands for a hydrogen atom, an alkyl group with 1–10 carbon atoms, or a substituent of —($A_4$—$Z_4$)$_s$—$A_6$—$X_3$; l, m, n and s each stands for an integer of 0 or 1, and p, and q each stands for an integer of 0–5; $X_3$ for an alkyl group with 1–10 carbon atoms; $Z_1$–$Z_4$ each independently stands for a covalent bond or an alkylene group with 1–5 carbon atoms, and one or more methylene groups in the alkylene group may be replaced by —CH=CH—, —C≡C—, or an oxygen atom and one or more hydrogen atoms i the alkylene group may be substituted by halogen atoms; the ring $A_1$–$A_6$ each independently stands for a 1,4-phenylene, a 1,4-cyclohexenylene, or a trans-1,4-cyclohexylene, and the carbon atoms in the ring may be replaced by nitrogen atoms or oxygen atoms and the hydrogen atoms in the ring may be substituted by halogen atoms or cyano groups; and $B_1$ and $B_2$ each independently stands for —CH=CH— or —C≡C—, with the proviso that both of $B_1$ and $B_2$ should not be —CH=CH— at the same time, (B) a liquid crys-line composition comprising at least one liquid crystalline compound of the general formula (1), and (C) a liquid crystal display element wherein the composition (B) is used. The liquid crystalline compounds of the present invention are distinguished by their characteristics of steep threshold voltage, an adequate magnitude of values in optical or dielectric anisotropy, an extremely high ratio of elastic constants and low viscosity in addition to good compatibility with other liquid crystalline compounds.

12 Claims, No Drawings

LIQUID CRYSTALLINE COMPOUNDS CONTAINING HYDROCARBON GROUPS, LIQUID CRYSTALLINE COMPOSITIONS, AND LIQUID CRYSTAL DISPLAY ELEMENTS

BACKGROUND OF THE INVENTION

1. Field of the Invention

The present invention relates to novel liquid crystalline compounds useful for electrooptical liquid crystal display materials, and more particularly, to novel liquid crystalline compounds exhibiting suitable various physical properties and liquid crystalline compositions comprised of the novel liquid crystalline compounds. In particular, The present invention relates also to novel liquid crystalline compounds possessing low viscosity (high responsibility) and adequate magnitude of values of optical anisotropy in addition to characteristics of steep threshold voltage and good compatibility with other liquid crystalline compounds and to novel liquid crystalline compositions composed of the novel liquid crystalline compounds as well as liquid crystal display elements.

2. Description of the Prior Art

From the past, a great number of compounds has been developed to have liquid crystalline characteristics. Such liquid crystalline compounds are required to possess various characteristics, and the following characteristics are above all regarded important:

1) characteristics of a steep threshold voltage,
2) shorter response time,
3) smaller electric power for driving,
4) a wider range of working temperature (good compatibility with other liquid crystalline compounds), and
5) chemical stability.

In the characteristics 4), such properties are involved that the melting point is low and that crystallization, precipitation of crystals or phase separation like precipitation of smectic phase is difficult to take place.

In order to exhibit such favorable characteristics, liquid crystalline compounds as constituent are required to possess the following characteristics:

a) higher ration of elastic constants (K33/K11),
b) lower viscosity (Phys. Lett., 39A, 69(1972),
c) In case of adding to a liquid crystalline composition, a temperature range for nematic phase is not shortened or phase separation such as precipitation of crystals, smectic phase or the like is hard to take place,
d) smaller ratio of elastic constants (K) (Mol. Cryst. Liq. Cryst., 12, 57 (1970), and
e) adequate magnitude of values of optical anisotropy and values of dielectric anisotropy (Appl. Phys. Lett., 38 (7), 497).

Among the aforesaid characteristics required, what is required for enhancing display quality of STN liquid crystalline compositions and STN liquid crystal display elements most widely utilized at the present time is steepness in characteristics of threshold voltage. It is known that this steepness is greatly caused by the ratio of elastic constants (K33/K11) (Proc. of the Japan Display, 388 (1986). It is also known that a compound having a larger ratio of elastic constants shows characteristics of steep threshold voltage. Thus, the use of a liquid crystalline composition possessing better characteristics of threshold voltage can provide a liquid crystalline composition and a liquid crystal display element of better display quality. In STN liquid crystalline materials, this steepness is one of the most important characteristics in practical use.

It is well known that compounds having an alkenyl group in a side chain thereof has a greater ratio elastic constants (K33/K11), and various compounds are proposed hitherto [Mo. Cryst. Liq. Cryst., 122, 241 (1985), ibid. 131, 10 (1985), ibid. 149, 359 (1987), and ibid. 165, 405 (1988)]. However, the ratio of elastic constants of these compounds are not as yet large enough for practical use. Under the above circumstances, therefore, there is a great demand in this art for developing a new liquid crystalline compound which has a satisfactorily large ratio of elastic constants as well as a liquid crystalline composition containing such compounds. Till now, such demand has not yet been fulfilled.

BRIEF SUMMARY OF THE INVENTION

Accordingly, it is an object of the present invention to provide a novel liquid crystalline compound suitable for electrooptical display elements and a liquid crystalline composition containing the novel compounds.

It is another object of the present invention to provide a novel liquid crystalline compound possessing characteristics of a steep threshold voltage, a good compatibility with other liquid crystalline compounds, a low viscosity (rapid responsibility), an adequate magnitude of values of optical anisotropy, and values of dielectric anisotropy as well as a novel liquid crystalline composition composed of the liquid crystalline compounds.

It is still another object of the present invention to provide a liquid crystal display element derived from the novel liquid crystalline composition.

Other and further objects, features and advantages of the present invention will be apparent more fully from the following description.

Taking the aforesaid circumstances into consideration, the present inventors have made extensive researches for solving the problems now encountered in the prior art and for developing a novel liquid crystalline compound possessing improved electroopitcal characteristics. As a result of such extensive researches, it has been found surprisingly that a liquid crystalline compounds having a new specific structure satisfies the aforesaid characteristics and is markedly improved in liquid crystalline properties as compared with the conventional liquid crystalline compounds. More precisely, it has now been found that introduction of a group containing therein the grouping —CH=CH— and the grouping —C≡C— together, i.e. a group represented by the formula:

(referred to hereinafter arbitrarily as eneyne group, p and q each standing for a numeral of 0–5) into the molecule of a liquid crystalline compound makes it exhibit the aforesaid desirable characteristics. The present invention has been accomplished on the basis of the above finding.

DETAILED DESCRIPTION OF THE INVENTION

In accordance with the first embodiment of the present invention, there is provided a liquid crystalline compound of the general formula:

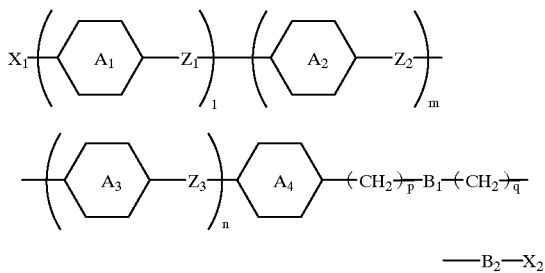

(1)

—B₂—X₂ wherein $X_1$ stands for a hydrogen atom, a cyano group, a halogen atom, or an alkyl group with 1–20 carbon atoms, and one or more methylene groups in the alkyl group may be replaced by —CH=CH—, —C≡C—, or oxygen atoms and one or more hydrogen atoms may be substituted by halogen atoms; $X_2$ stands for a hydrogen atom, an alkyl group with 1–10 carbon atoms, or a substituent of —($A_5$—$Z_4$)$_s$—$A_6$—$X_3$; l, m, n and s each stands for an integer of 0 or 1, and p, and q each stands for an integer of 0–5; $X_3$ for an alkyl group with 1–10 carbon atoms; $Z_1$–$Z_4$ each independently stands for a covalent bond or an alkylene group with 1–5 carbon atoms, and one or more methylene groups in the alkylene group may be replaced by —CH=CH—, —C≡C—, or an oxygen atom and one or more hydrogen atoms in the alkylene group may be substituted by halogen atoms; the ring $A_1$–$A_6$ each independently stands for a 1,4-phenylene, a 1,4-cyclohexenylene, or a trans-1,4-cyclohexylene, and the carbon atoms in the ring may be replaced by nitrogen atoms or oxygen atoms and the hydrogen atoms in the ring may be substituted by halogen atoms or cyano groups; and $B_1$ and $B_2$ each independently stands for —CH=CH— or —C≡C—, with the proviso that both of $B_1$ and $B_2$ should not be —CH=CH— at the same time.

In accordance with the second embodiment of the present invention, there is provided a liquid crystalline compound of the general formula (1) wherein $X_1$ stands for an alkyl group, an alkenyl group, an alkoxymethyl group, a halogen atom, or a cyano group.

In accordance with the third embodiment of the present invention, there is provided a liquid crystalline compound of the general formula (1) wherein $X_2$ stands for a hydrogen atom or an alkyl group with 1–10 carbon atoms.

In accordance with the fourth embodiment of the present invention, there is provided a liquid crystalline compound of the general formula (1) wherein $X_2$ stands for a substituent of —($A_5$—$Z_4$)$_s$—$A_6$—$X_3$ wherein $A_5$, $Z_4$, $A_6$, and $X_3$ have the same meanings as given above.

In accordance with the firth embodiment of the present invention, there is provided a liquid crystalline composition which comprises at least one of the aforesaid liquid crystalline compounds.

In accordance with the sixth embodiment of the present invention, there is provided a liquid crystalline composition which comprises at least one of the liquid crystalline compound disclosed in any of the aforesaid first to fourth embodiments as a first component and at least one of the liquid crystalline compound selected from the group consisting of the general formulas (2), (3) and (4):

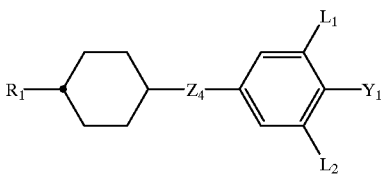

(2)

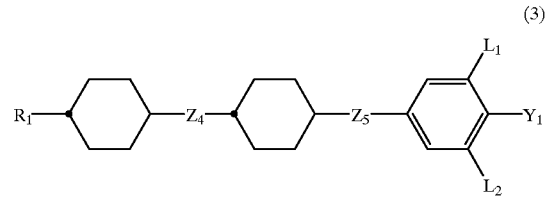

(3)

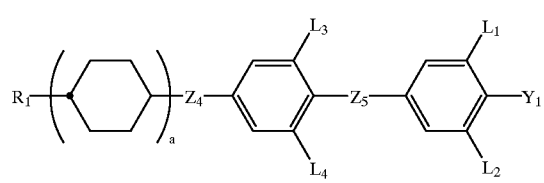

(4)

wherein $R_1$ stands for an alkyl group with 1–10 carbon atoms; $Y_1$ stands for a fluorine atom, a chlorine atom, —OCF₃, —OCF₂H, —CH₃, —CF₂H, or —CFH₂; $L_1$, $L_2$, $L_3$, and $L_4$ each independently stands for a hydrogen atom or a fluorine atom; $Z_4$ and $Z_5$ each independently stands for —CH₂CH₂—, —CH=CH—, or a covalent bond; and a stands for an integer of 1 or 2, as a second component.

In accordance with the seventh embodiment of the present invention, there is provided a liquid crystalline composition which comprises at least one liquid crystalline compound disclosed in any of the aforesaid first to fourth embodiments as a first component and at least one liquid crystalline compound selected from the group consisting of the following general formulas (5), (6), (7), (8) and (9):

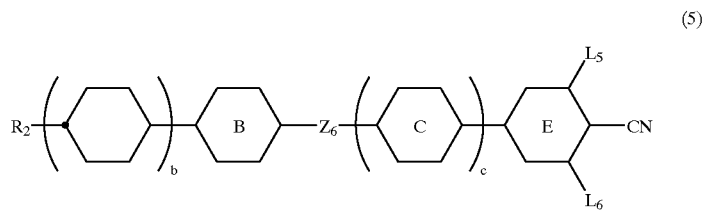

(5)

wherein $R_2$ stands for a fluorine atom, and an alkyl group with 1–10 carbon atoms, or an alkenyl group with 2–10 carbon atoms, and one or more methylene groups in those groups may be replaced by oxygen atoms with the proviso that plural consecutive methylene groups are not replaced by oxygen atoms; the ring B stands for a trans-1,4-cyclohexylene, a 1,4-phenylene, or a trans-1,3-dioxan-2,5-diyl; the ring C stands for a trans-1,4-cyclohexylene, a 1,4-phenylene, or a pyrimidin-2,5-diyl; the ring E stands for a tans-1,4-cyclohexylene, or a 1,4-phenylene group; $Z_6$ stands for —$CH_2CH_2$—, —$CO_2$, or a covalent bond; $L_5$ and $L_6$ each independently stands for a hydrogen atom or a fluorine atom; and b and c each independently stands for an integer of 0 or 1, 2–10 carbon atoms, one or more methylene groups in those groups may be replaced by oxygen atoms with the proviso that plural consecutive methylene groups are not replaced by oxygen atoms; the ring H stands for a trans-1,4-cyclohexylene, a 1,4-phenylene, or pyrimidin-2,5-diyl; the ring I stands for a trans-1,4-cyclohexylene or a 1,4-phenylene; $Z_{10}$ stands for —C≡C—, —$CO_2$—, —$CH_2$—$CH_2$—, —CH=CH—C≡C—, or a covalent bond; and $Z_{11}$ stands for —$CO_2$— or a covalent bond, (9)

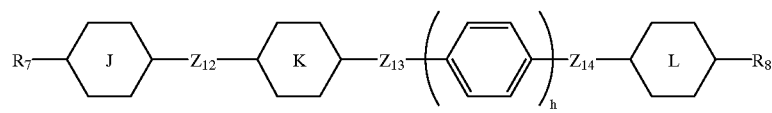

wherein $R_7$ and $R_8$ stand each independently for an alkyl group with 1– carbon atoms or an alkenyl group with 2–10 carbon atoms, one or more methylene groups in those groups may be replaced by an oxygen atom, with the proviso that plural consecutive methylene groups are not replaced by oxygen atoms; the ring J stands for a trans-1,4-cyclohexylene, a 1,4-phenylene, or a pyrimidin-2,5-diyl; the ring K stands for a trans-1,4-cyclohexylene, a 1,4-phenylene, in which one or more hydrogen atoms on the 1,4-phenylene ring may be substituted by one or more fluorine atoms, or a pyrimidin-2,5-diyl; the ring L stands for a trans-1,4-cyclohexylene or a 1,4-phenylene; $Z_{12}$ and $Z_{13}$ stand each independently for —$CO_2$—, —$CH_2CH_2$— or a covalent bond; $Z_{14}$ stands for —CH=CH—, —C≡$C_{13}$, (6)

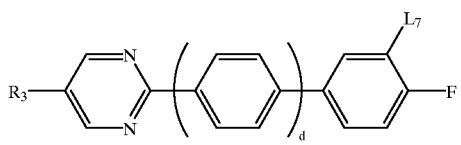

wherein $R_3$ stands for an alkyl group with 1–10 carbon atoms; $L_7$ stands for a hydrogen atom or a fluorine atom; and d stands for an integer of 0 or 1, (7)

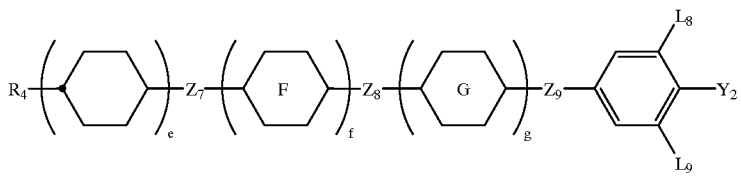

wherein $R_4$ stands for an alkyl group with 1–10 carbon atoms; the rings F and G each independently stands for a trans-1,4-cyclohexylene or a 1,4-phenylene; $Z_7$ and $Z_8$ each independently stands for —$CO_2$— or a covalent bond; $Z_9$ stands for —$CO_2$— or —C≡C—; $L_8$ and $L_9$ each independently stands for a hydrogen atom or fluorine atom; $Y_2$ stands for a fluorine atom, —$OCF_2H$, —$CF_3$, —$CF_2H$, or —$CFH_2$; and e, f and g each independently stands for an integer of 0 or 1, (8)

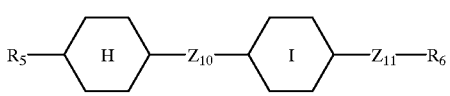

wherein $R_5$ and $R_6$ each independently stands for an alkyl group with 1–10 carbon atoms or an alkenyl group with —$CO_2$— or a covalent bond; and h for an integer of 0 or 1; as a second component.

In accordance with the eighth embodiment of the present invention, there is provided a liquid crystalline composition which comprises at least one liquid crystalline compound disclosed in any of the aforesaid first to fourth embodiments as a first component, at least one selected from the liquid crystalline compounds of the general formulas (2), (3), and (4) as a part of the second component and at least one selected from the liquid crystalline compounds of the general formulas (5), (6), (7), (8), and (9) as the other part of the second component.

In accordance with the ninth embodiment of the present invention, there is provided a liquid crystal display element wherein the liquid crystalline composition disclosed in any one of the fifth to eighth embodiments of the present invention is used.

The liquid crystalline compounds of the present invention can be classified into compounds having eneyne groups at the terminal ends of the molecule thereof (1-1) and compounds having eneyne group at the central part the molecule thereof (1-2).

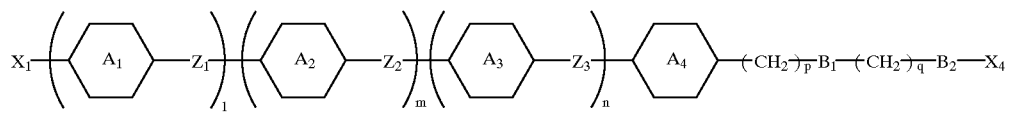
(1-1)
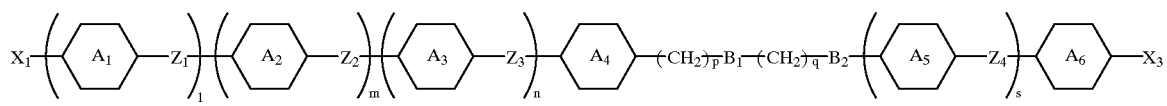
(1-2)
wherein $X_1$, $X_3$, $A_1$–$A_6$, $B_1$, $B_2$, $Z_1$–$Z_4$, l, m, n, n, p, and q have the same meanings as given above and $X_4$ stands for an alkyl group with 1–10 carbon atoms.
More particularly, the liquid crystalline compounds of the present invention can be developed as will be shown hereinafter.
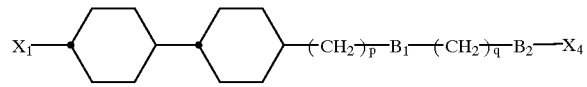
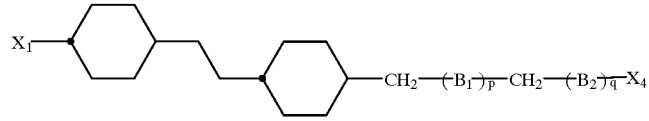
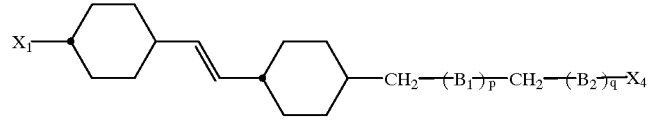
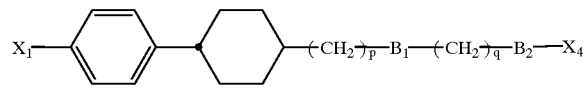
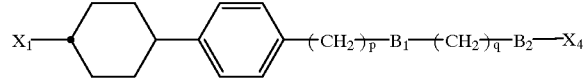
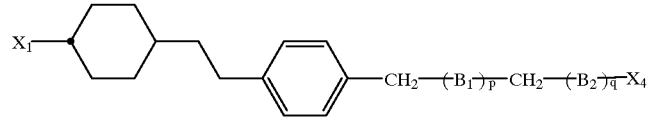
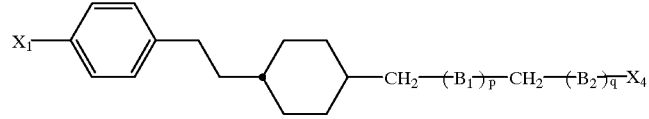
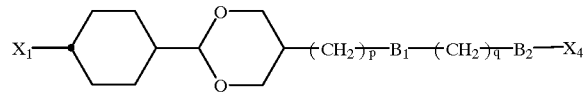
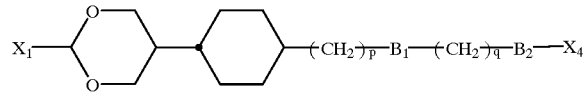
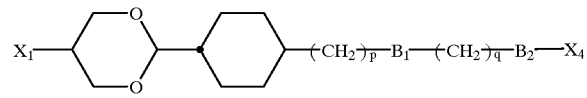

-continued
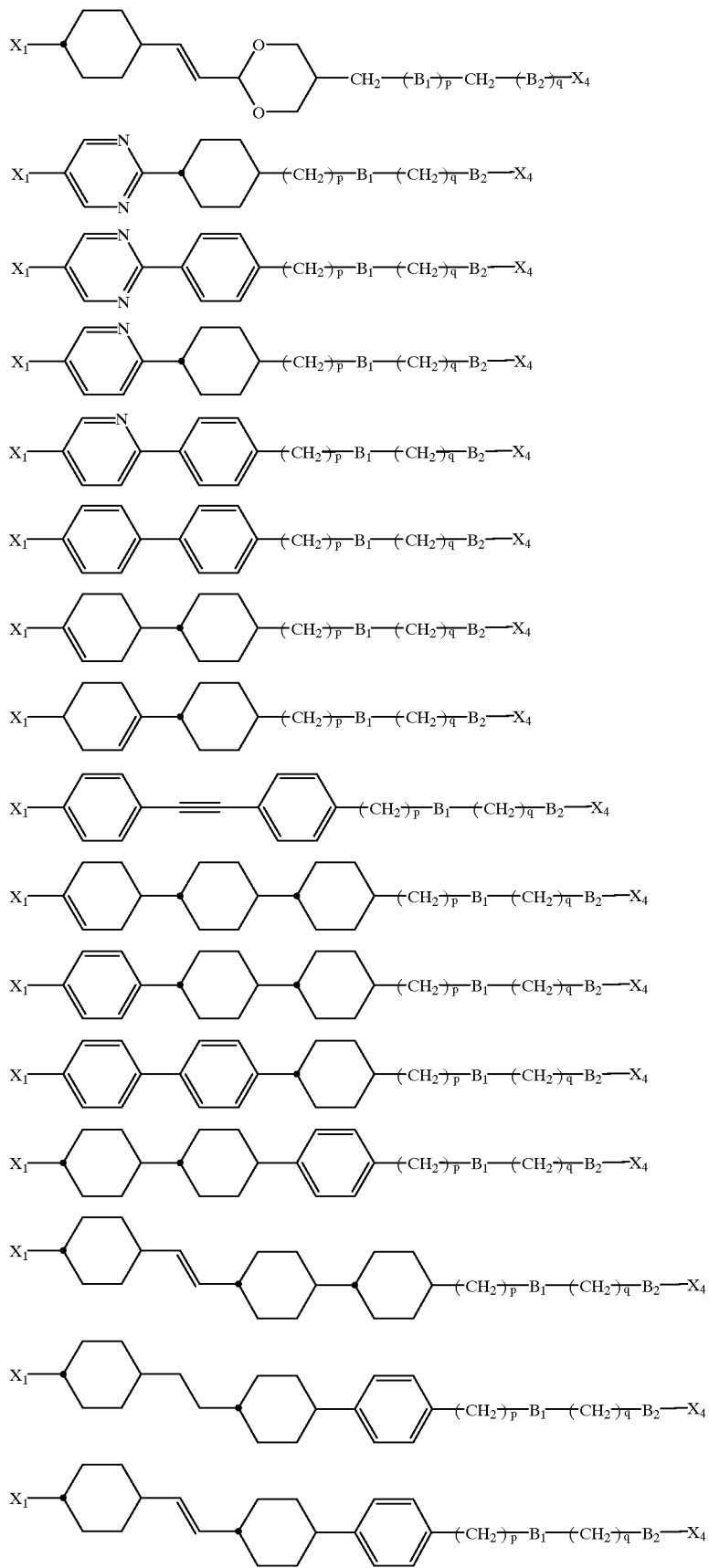

-continued
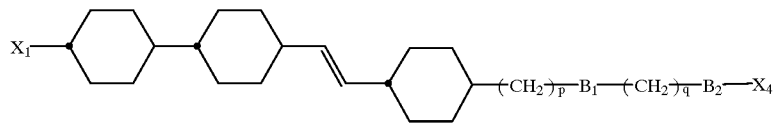
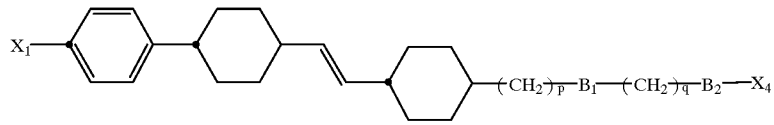
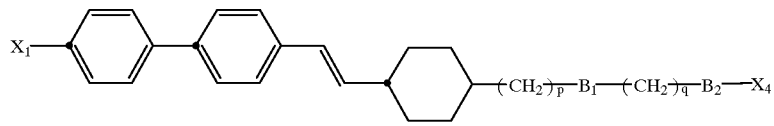
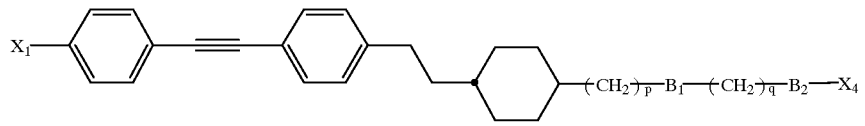
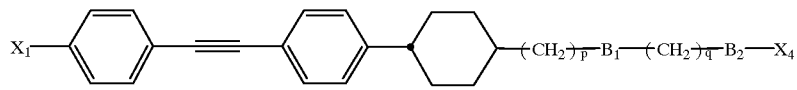
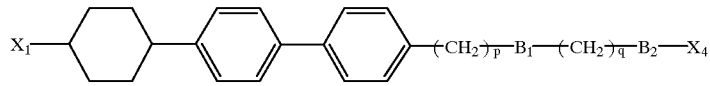
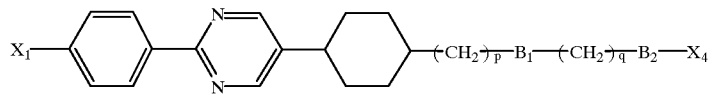
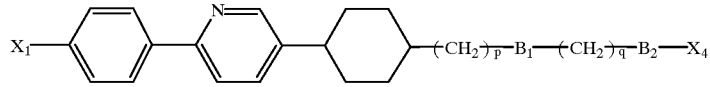
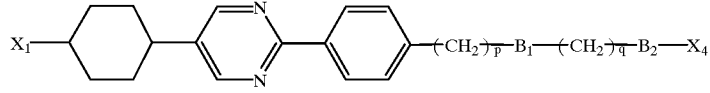
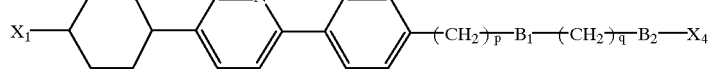
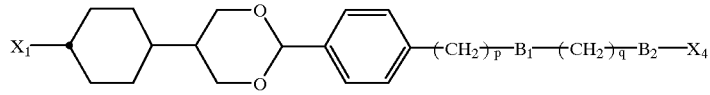
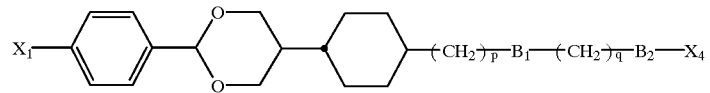
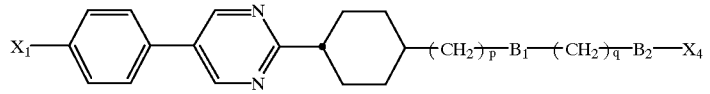
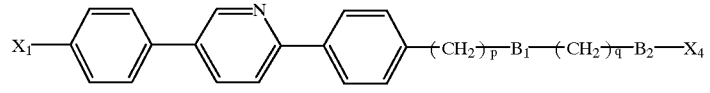
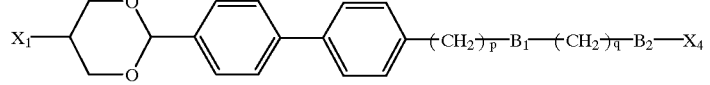
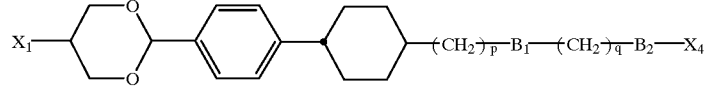

-continued
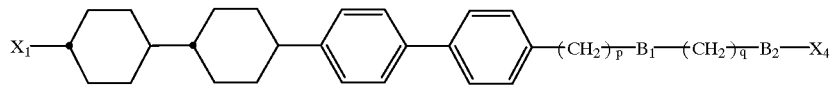
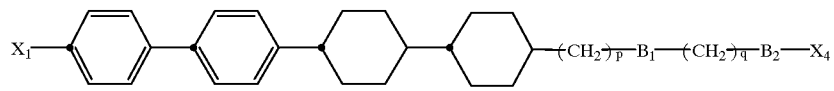
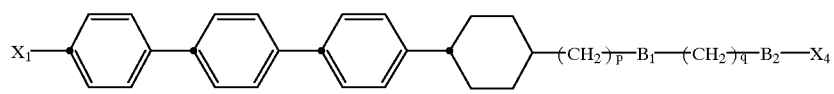
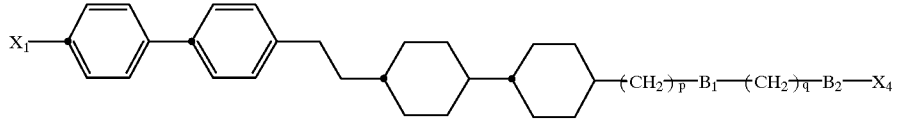
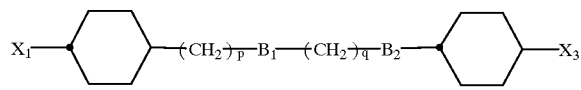
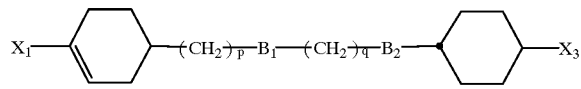
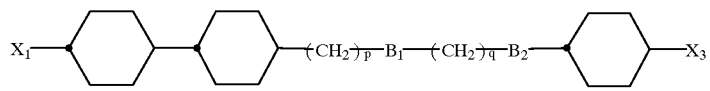
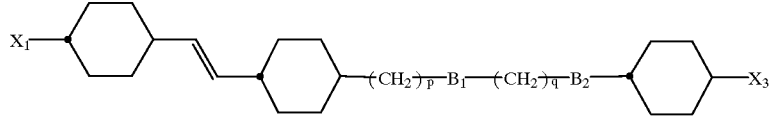
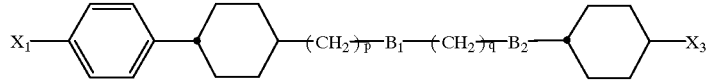
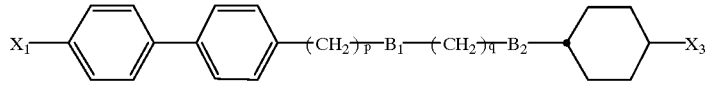
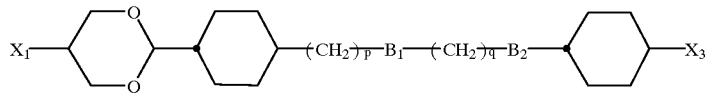
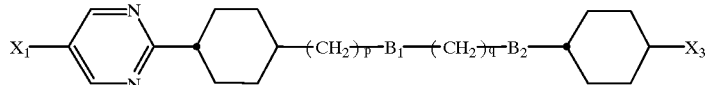
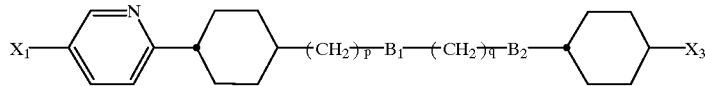
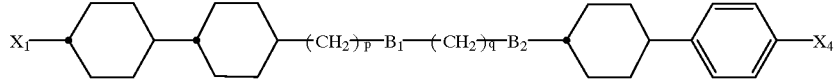
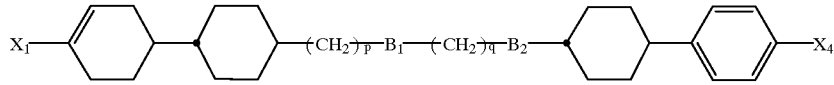
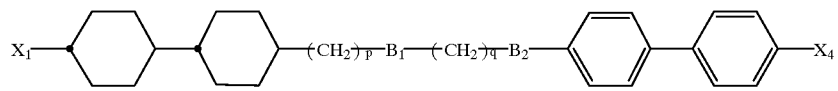

In the above formulas, $X_1$, p, q, $B_1$ and $B_2$ have the same meanings as give above and $X_4$ stands for an alkyl group with 1–10 carbon atoms. Hydrogen atoms in each ring as depicted may be replaced by a cyano group and a halogen atom.

The notations p and q each stands for an integer of 0–5. In case of considering chemical stability of these compounds, p is preferably at least one when $A_4$ stands for a 1,4-phenylene group. In all of the cases, the compound wherein q is at least 1 is preferable in consideration of chemical stability.

Suitable characteristics can be achieved by the use of any eneyne group that contains the grouping —CH═CH— and the grouping —C≡C— together in the molecule. Preferable are the following eneyne groups:

—CH═CH—C≡C—$X_2$
—CH═CH—CH$_2$—C≡C—$X_2$
—CH═CH—(CH$_2$)$_2$—C≡C—$X_2$
—CH═CH—(CH$_2$)$_3$—C≡C—$X_2$
—CH═CH—(CH$_2$)$_4$—C≡C—$X_2$
—CH═CH—(CH$_2$)$_5$—C≡C—$X_2$
—CH$_2$—CH═CH—C≡C—$X_2$
—CH$_2$—CH═CH—CH$_2$—C≡C—$X_2$
—CH$_2$—CH═CH—(CH$_2$)$_2$—C≡C—$X_2$
—CH$_2$—CH═CH—(CH$_2$)$_3$—C≡C—$X_2$
—CH$_2$—CH═CH—(CH$_2$)$_4$—C≡C—$X_2$
—(CH$_2$)$_2$—CH═CH—C≡C—$X_2$
—(CH$_2$)$_2$—CH═CH—C≡C—$X_2$
—(CH$_2$)$_2$—CH═CH—CH$_2$—C≡C—$X_2$
—(CH$_2$)$_2$—CH═CH—(CH$_2$)$_2$—C≡C—$X_2$
—(CH$_2$)$_2$—CH═CH—(CH$_2$)$_3$—C≡C—$X_2$
—(CH$_2$)$_3$—CH═CH—C≡C—$X_2$
—(CH$_2$)$_3$—CH═CH—CH$_2$—C≡C—$X_2$
—(CH$_2$)$_3$—CH═CH—(CH$_2$)$_2$—C≡C—$X_2$
—(CH$_2$)$_4$—CH═CH—C≡C$_{13\ X2}$
—(CH$_2$)$_4$—CH═CH—CH$_2$—C≡C—$X_2$
—C≡C—CH═CH—$X_2$
—C≡C—CH$_2$—CH═CH—$X_2$
—C≡C—(CH$_2$)$_2$—CH═CH—$X_2$
—C≡C—(CH$_2$)$_3$—CH═CH—$X_2$
—C≡C—(CH$_2$)$_4$—CH═CH—$X_2$
—C≡C—(CH$_2$)$_5$—CH═CH—$X_2$
—CH$_2$—C≡C—CH═CH—$X_2$
—CH$_2$—C≡C—CH$_2$—CH═CH—$X_2$
—CH$_2$—C≡C—(CH$_2$)$_2$—CH═CH—$X_2$
—CH$_2$—C≡C—(CH$_2$)$_3$—CH═CH—$X_2$
—CH$_2$—C≡C—(CH$_2$)$_4$—CH═CH—$X_2$
—(CH$_2$)$_2$—C≡C—CH═CH—$X_2$
—(CH$_2$)$_2$—C≡C—CH$_2$—CH═CH—$X_2$
—(CH$_2$)$_2$—C≡C—(CH$_2$)$_2$—CH═CH—$X_2$
—(CH$_2$)$_2$—C≡C—(CH$_2$)$_3$—CH═CH—$X_2$
—(CH$_2$)$_3$—C≡C—CH═CH—$X_2$
—(CH$_2$)$_2$—C≡C—CH$_2$—CH═CH—$X_2$
—(CH$_2$)$_3$—C≡C—(CH$_2$)$_2$—CH═CH—$X_2$
—(CH$_2$)$_4$—C≡C—CH═CH—$X_2$
—(CH$_2$)$_4$—C≡C—CH$_2$—CH═CH—$X_2$

In the above formulas, $X_2$ has the same meanings as given above. More preferable are the following compounds:

—CH═CH—CH$_2$—C≡C—$X_2$
—CH═CH—(CH$_2$)$_2$—C≡C—$X_2$
—CH═CH—(CH$_2$)$_3$—C≡C—$X_2$
—CH$_2$—CH═CH—CH$_2$—C≡C—$X_2$
—CH$_2$—CH═CH—(CH$_2$)$_2$—C≡C—$X_2$
—(CH$_2$)$_2$—CH═CH—CH$_2$—C≡C—$X_2$
—(CH$_2$)$_2$—CH═CH—(CH$_2$)$_2$—C≡C—$X_2$
—(CH$_2$)$_3$—CH═CH—CH$_2$—C≡C—$X_2$
—(CH$_2$)$_3$—CH═CH—(CH$_2$)$_2$—C≡C—$X_2$
—C≡C—CH$_2$—CH═CH—$X_2$
—C≡C—(CH$_2$)$_2$—CH═CH—$X_2$
—C≡C—(CH$_2$)$_3$—CH═CH—$X_2$
—CH$_2$—C≡C—CH$_2$—CH═CH—$X_2$
—CH$_2$—C≡C—(CH$_2$)$_2$—CH═CH—$X_2$
—(CH$_2$)$_2$—C≡C—CH$_2$—CH═CH—$X_2$
—(CH$_2$)$_2$—C≡C—(CH$_2$)$_2$—CH═CH—$X_2$
—(CH$_2$)$_3$—C≡C—CH$_2$—CH═CH—$X_2$
—(CH$_2$)$_3$—C≡C—(CH$_2$)$_2$—CH═CH—$X_2$

In the above formulas, $X_2$ has likewise the same meaning as given above.

The liquid crystalline compounds represented by the general formula (1) possess an extremely high ratio of elastic constants (K33/K11) as compared with the conventional liquid crystalline compounds. The liquid crystalline compounds represented by the general formula (1) also exhibit a greater value of K33/K11 as compared with the known liquid crystalline compounds. Further, the liquid crystalline compounds show very little temperature dependency, especially in lower temperature ranges, of the above ratio as compared with the known liquid crystalline compounds.

All of the liquid crystalline compounds represented by the general formula (1) show good solubility to other liquid crystalline compounds or liquid crystalline compositions so that a liquid crystalline composition using the compounds represented by the general formula (1) does not damage the nematic phase even at a low temperature (for example, at —20° C. required in aspect of practical use).

Since the liquid crystalline compounds represented by the general formula (1) exhibit suitable physiochemical characteristics as electroptical display material, a liquid crystalline composition possessing favorable physiochemical characteristics can by provided by using the compounds of the general formula (1).

All of the compounds of the general formula (1) shows a low viscosity so that in case of preparing a liquid crystalline composition, the viscosity of a whole composition will not be increased even if the compounds are used in greater amounts. These compounds show an extremely small temperature dependency of viscosity, in particular at a low temperature range. By using these low viscosity compounds, it is now possible to prepare a liquid crystalline composition having a rapid responsibility.

All of the compounds of the general formula (1) possesses a suitable magnitude of values of optical anisotropy and a suitable magnitude of values of dielectric anisotropy. In addition, all of the compounds of the general formula (1) is of an extremely chemical stability so that a liquid crystalline composition using these compounds is very high in specific resistance and voltage retention rate. These compounds also show an extremely high stability to external factors such as ultraviolet light and heating, thus exhibiting a satisfactory chemical resistance as a constructive element for a practical liquid crystalline composition.

The compounds of the present invention are particularly suitable for STN liquid crystalline compositions but are also suitably used for other applications. For example, these compounds are utilizable as TN liquid crystalline compounds, liquid crystalline compounds are utilizable as TN liquid crystalline compounds for polymer dispersion-type liquid crystal elements, strong dielectric liquid crystalline compounds, and strong anti-dielectric liquid crystalline compounds.

The liquid crystalline composition of the present invention preferably contains 0.1–99.9% by weight of at least one compound of the general formula (1) for exhibiting good characteristics.

The liquid crystalline composition of the present invention is accomplished by blending a first component containing at least one compound of the general formula (1) with compounds suitably selected from a group of the compounds represented by the general formulas (2)–(9) according to a desired purpose.

The following compounds are preferably used as compounds of the general formulas (2)–(4) wherein $R_1$ has the same meaning as given above:

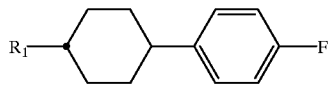
(2-1)

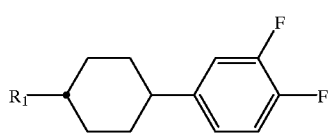
(2-2)

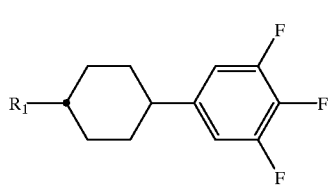
(2-3)

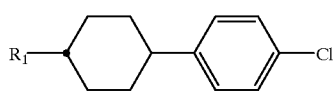
(2-4)

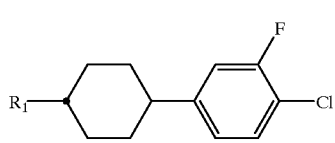
(2-5)

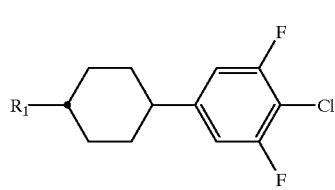
(2-6)

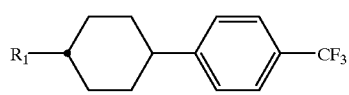
(2-7)

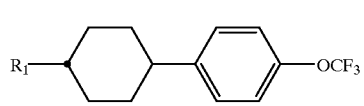
(2-8)

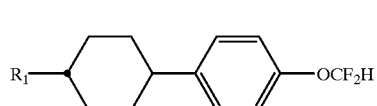
(2-9)

(2-10)

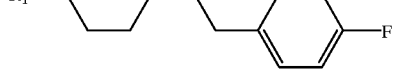

-continued

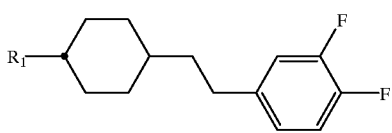
(2-11)

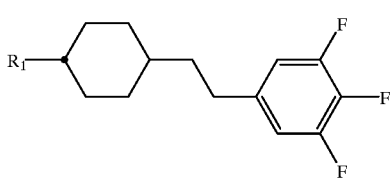
(2-12)

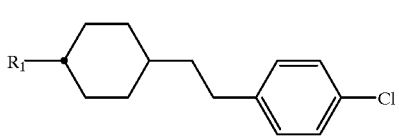
(2-13)

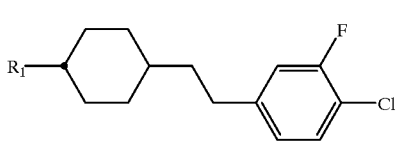
(2-14)

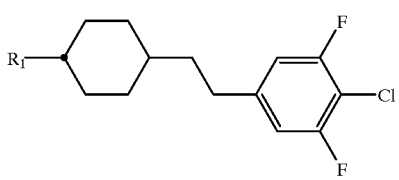
(2-15)

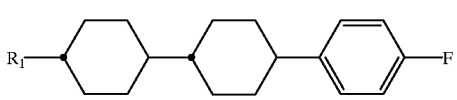
(3-1)

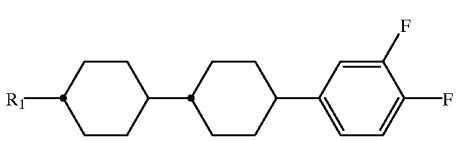
(3-2)

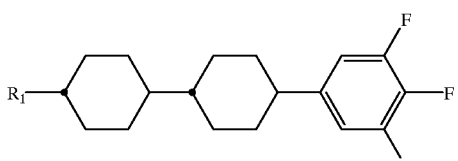
(3-3)

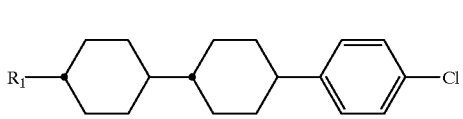
(3-4)

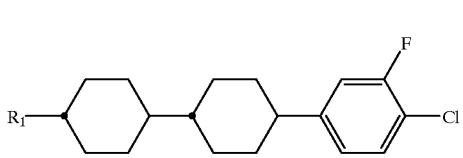
(3-5)

(3-6)
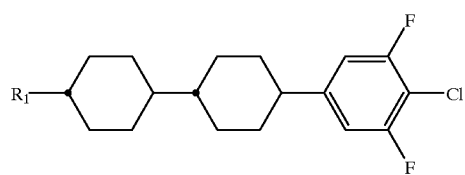
(3-7)
(3-8)
(3-9)
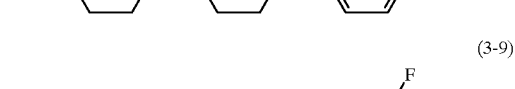
(3-10)
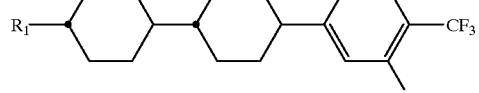
(3-11)
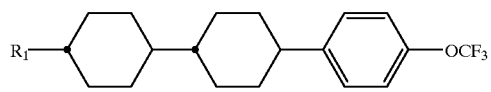
(3-12)
(3-13)
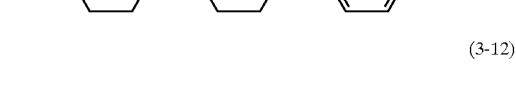
(3-14)
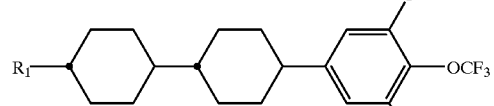
(3-15)
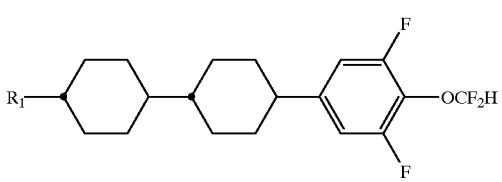
(3-16)
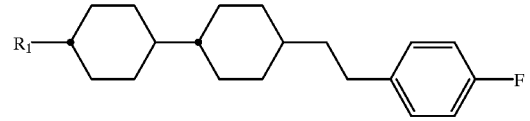
(3-17)
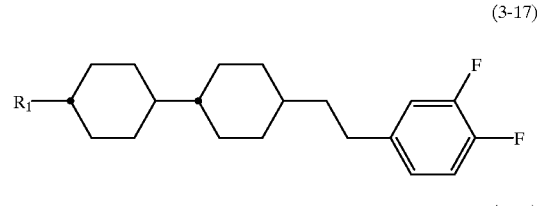
(3-18)
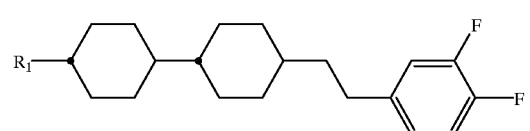
(3-19)
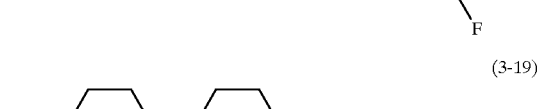
(3-20)
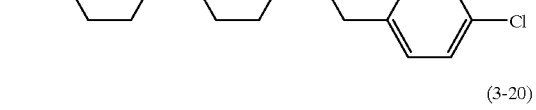
(3-21)
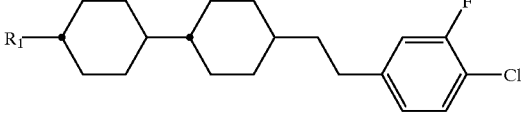
(3-22)
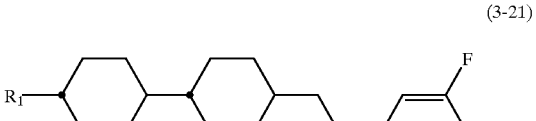

(3-23)
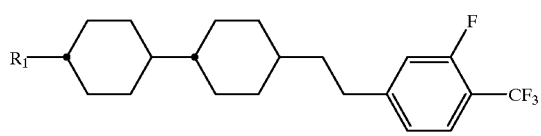
(3-24)
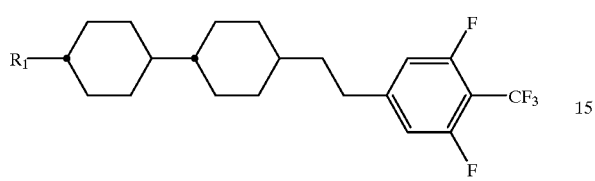
(3-25)
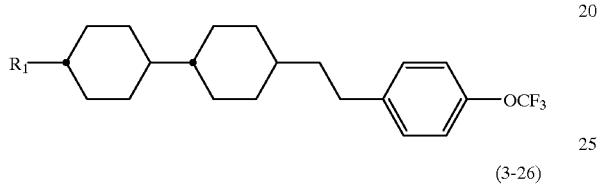
(3-26)
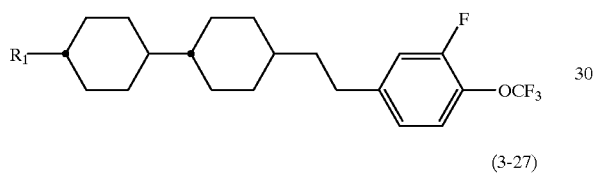
(3-27)
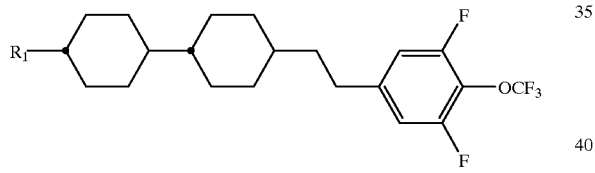
(3-28)
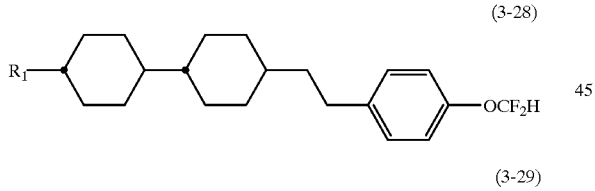
(3-29)
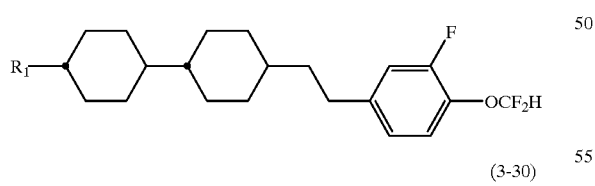
(3-30)
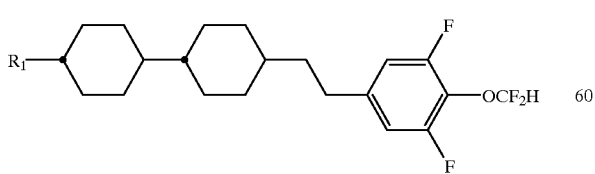
(3-31)
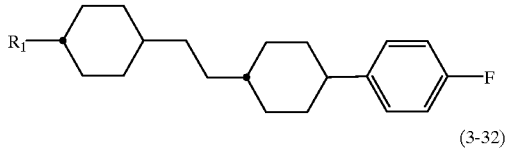
(3-32)
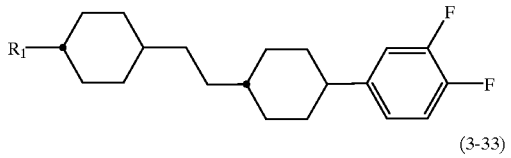
(3-33)
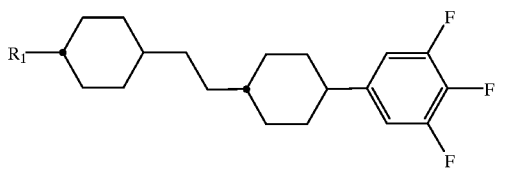
(3-34)
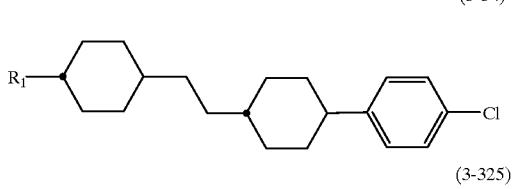
(3-325)
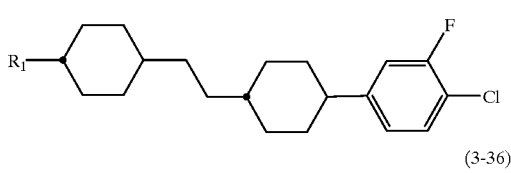
(3-36)
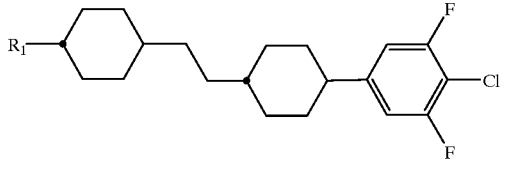
(3-37)
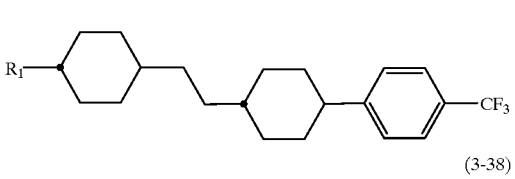
(3-38)
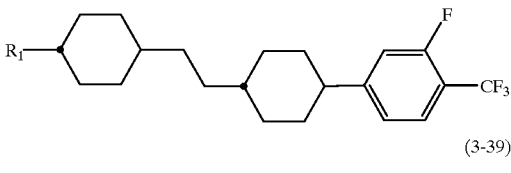
(3-39)
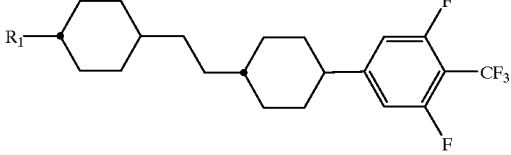

-continued
(3-40) 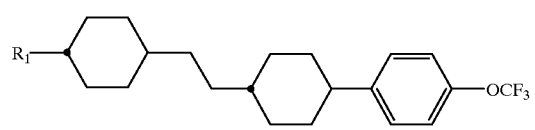
(3-41) 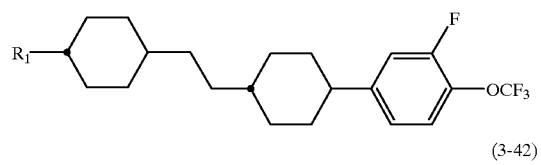
(3-42) 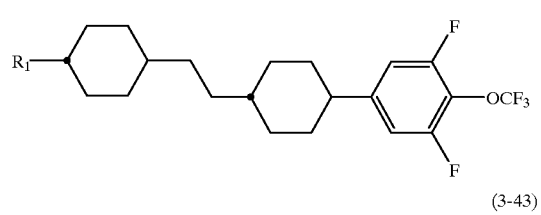
(3-43) 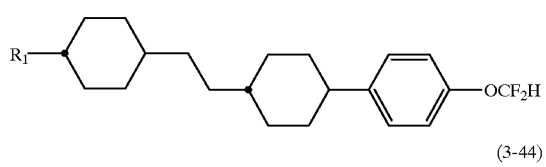
(3-44) 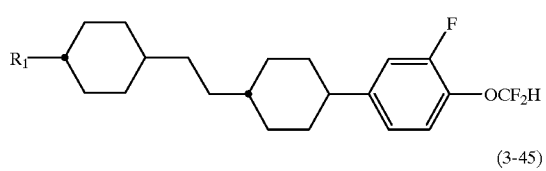
(3-45) 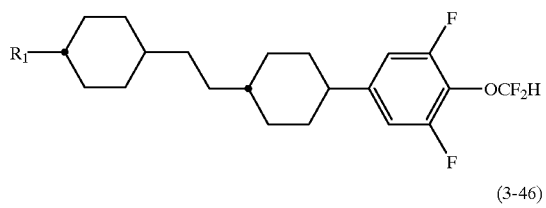
(3-46) 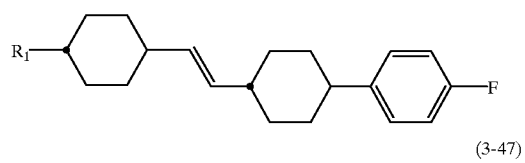
(3-47) 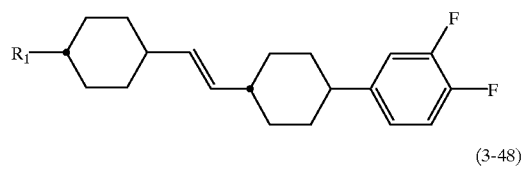
(3-48) 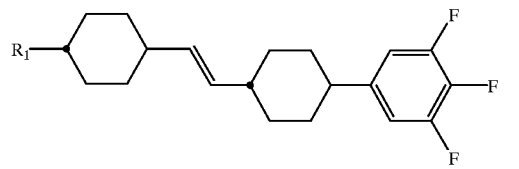
-continued
(4-1) 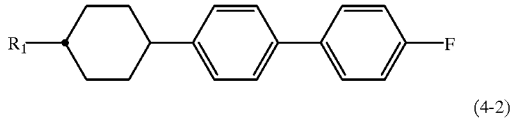
(4-2) 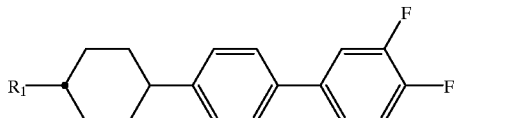
(4-3) 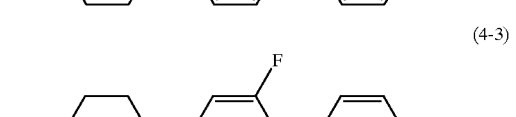
(4-4) 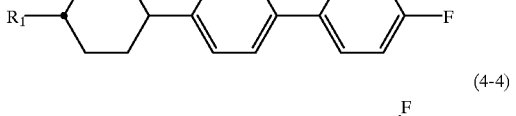
(4-5) 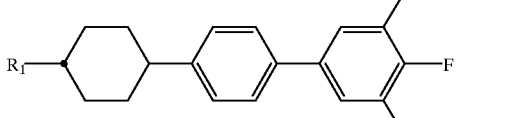
(4-6) 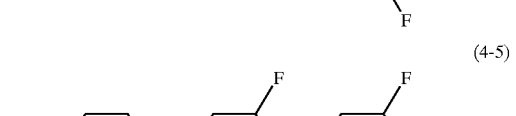
(4-7) 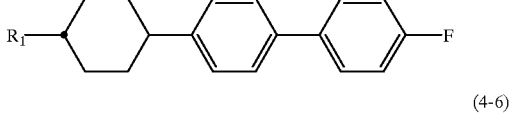
(4-8) 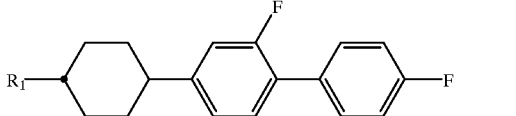
(4-9) 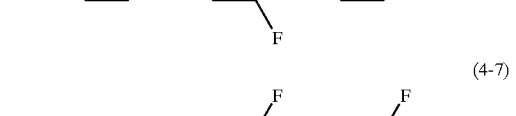
(4-10) 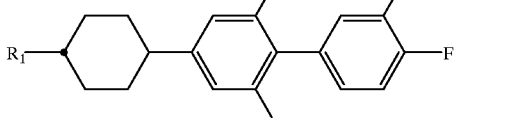

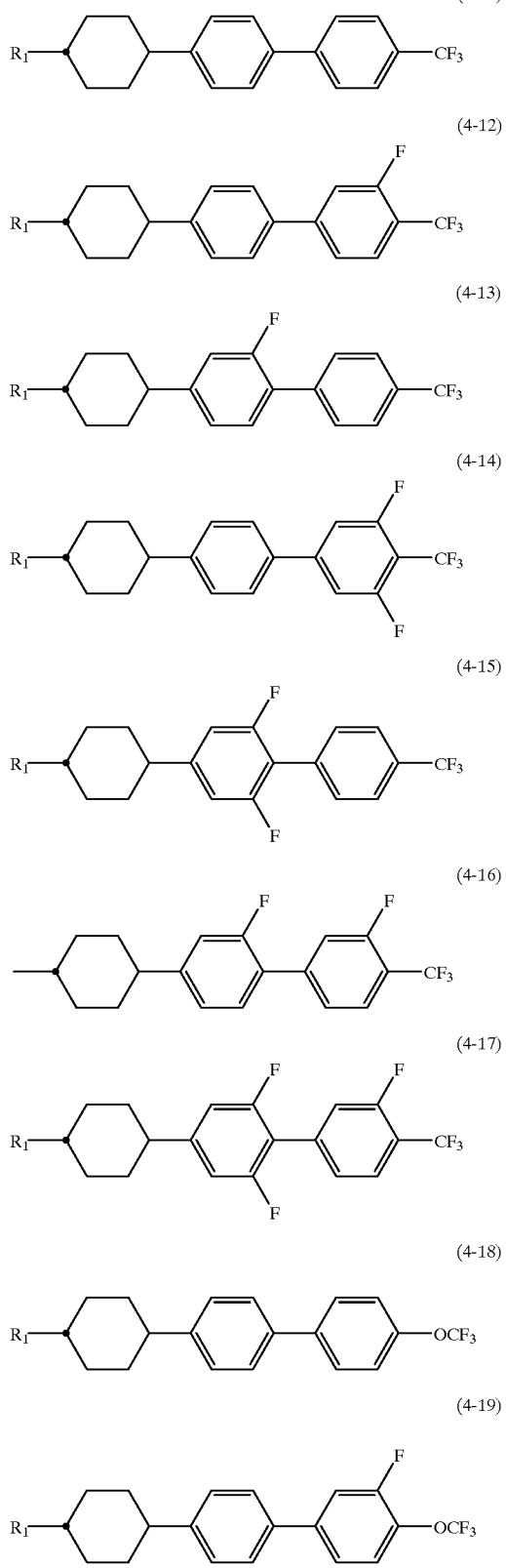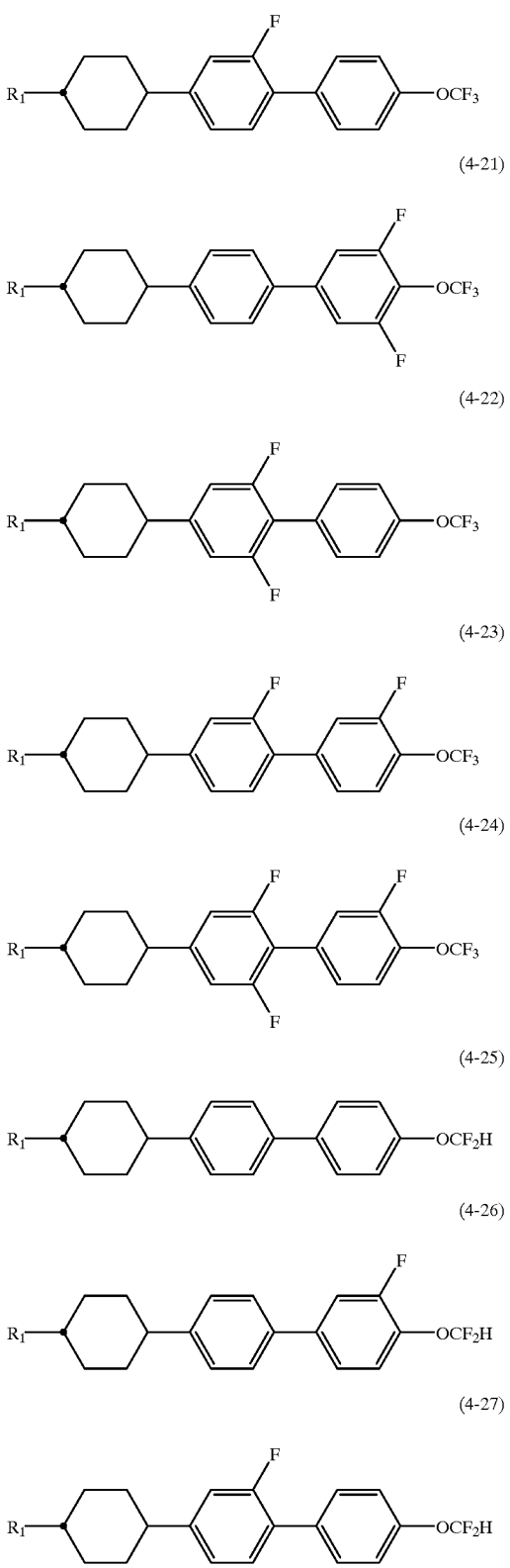

(4-28)
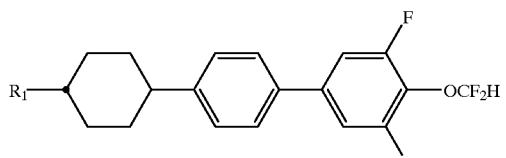
(4-29)
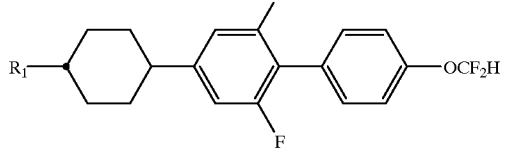
(4-30)
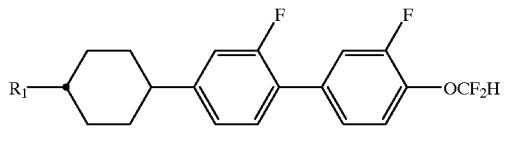
(4-31)
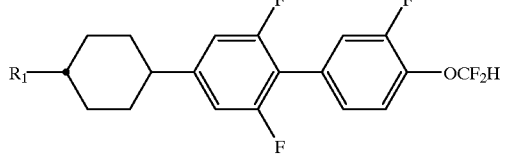
(4-32)
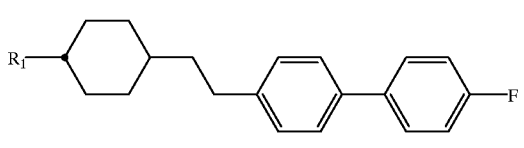
(4-33)
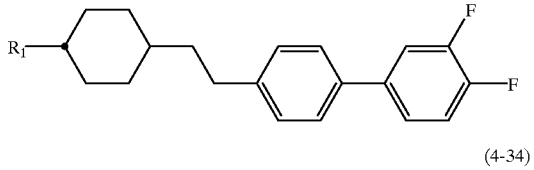
(4-34)
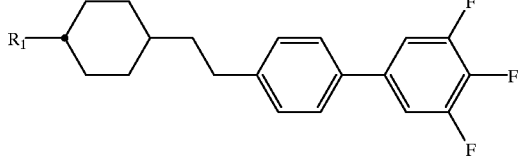
(4-35)
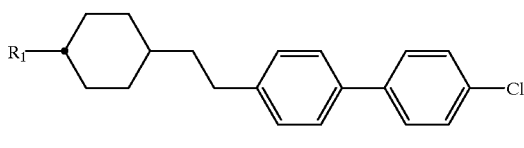
(4-36)
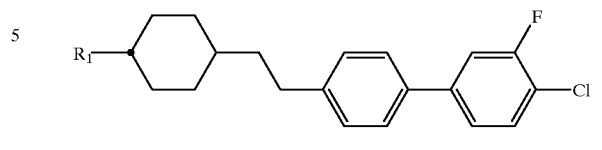
(4-37)
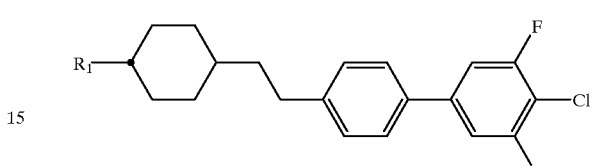
(4-38)
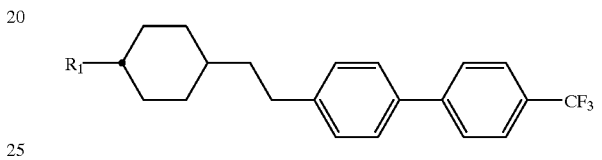
(4-39)
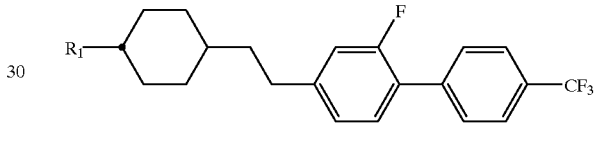
(4-40)
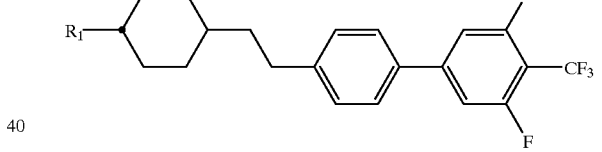
(4-41)
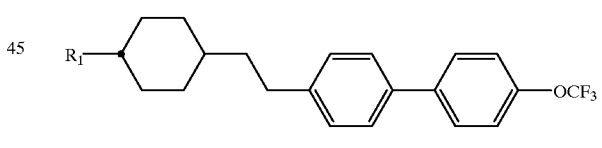
(4-42)
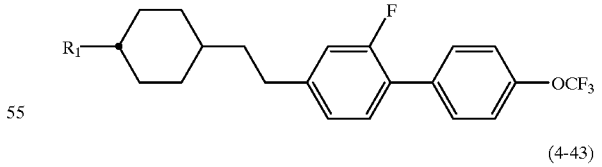
(4-43)
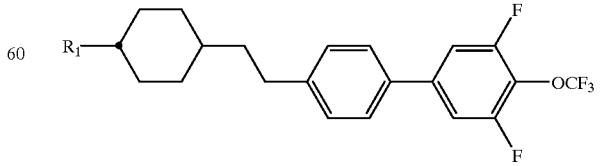

(4-44)
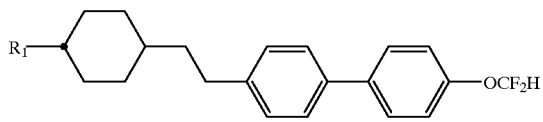

(4-45)
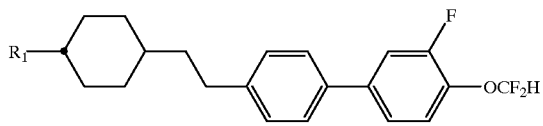

(4-46)
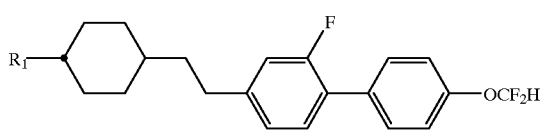

(4-47)
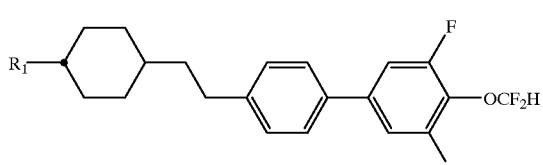

(4-48)
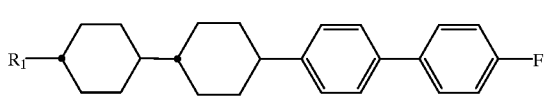

(4-49)
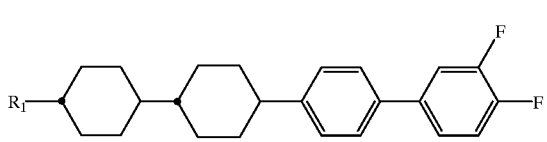

(4-50)

(4-51)

(4-52)

(4-53)

The compounds represented by the general formulas (2)–(4) show positive values of dielectric anisotropy and are excellent in thermal stability and chemical stability so that these compounds are indispensable for the preparation of a liquid crystalline composition for TFT where high trustworthiness such as a high voltage retention rate (or a large value of specific resistance) is required.

In the preparation of a liquid crystalline composition for TFT, the amount of a compound of the general formulas (2)–(4) is properly used within the range of 1–99% by weight based on the total weight of the liquid crystalline composition but is preferably used within the range of 10–97% more preferably 40–95% by weight. In this case, the composition may contain compounds represented by the general formulas (5)–(9). In the preparation of liquid crystalline compositions for STN or TN display use, compounds of the general formulas (2)–(4) can also be used.

Illustrative of the compounds of the general formulas (5)–(7) are preferably the compounds shown by the following formulas wherein $R_2$, $R_3$ and $R_4$ have the same meanings give above:

(5-1)
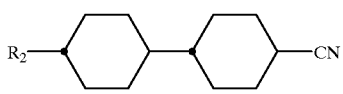

(5-2)
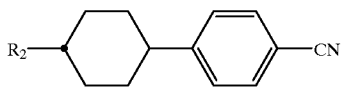

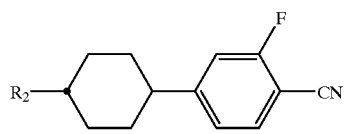
(5-3)
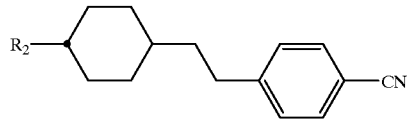
(5-4)
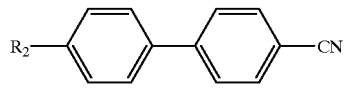
(5-5)
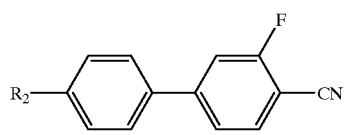
(5-6)
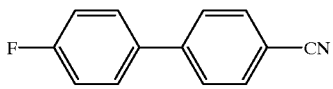
(5-7)
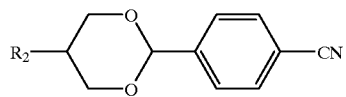
(5-8)
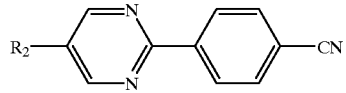
(5-9)
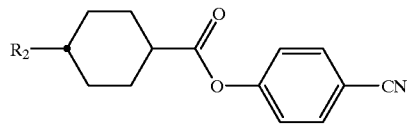
(5-10)
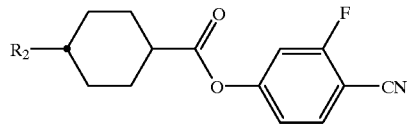
(5-11)
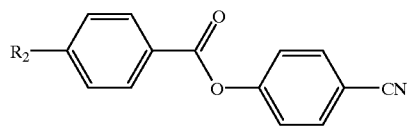
(5-12)

-continued
(5-13)
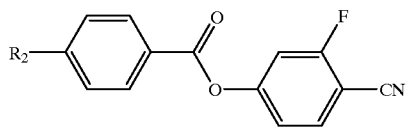
(5-14)
(5-15)
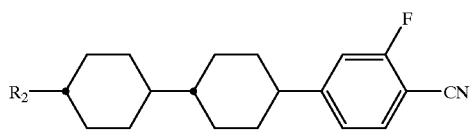
(5-16)
(5-17)
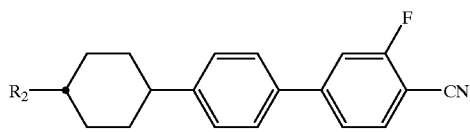
(5-18)
(5-19)
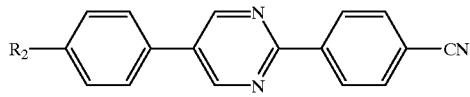
(5-20)
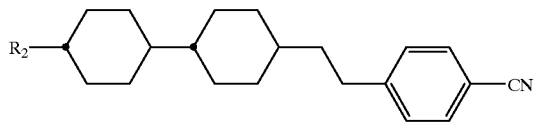
(5-21)
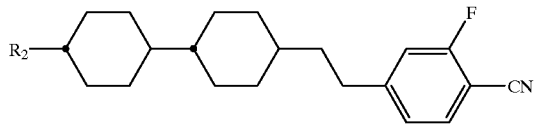
(5-22)
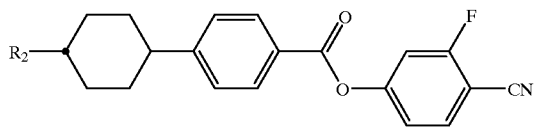

-continued
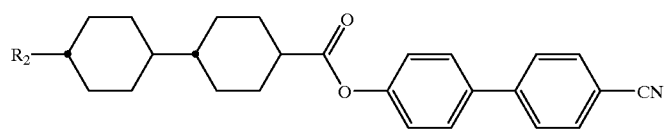 (5-23)
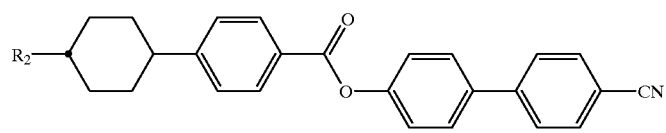 (5-24)
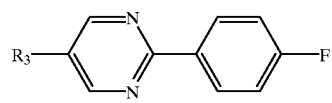 (6-1)
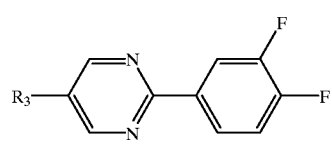 (6-2)
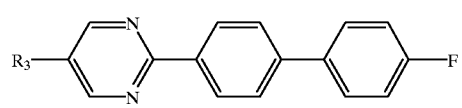 (6-3)
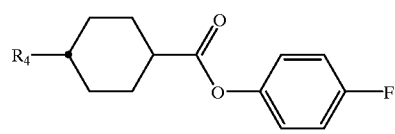 (7-1)
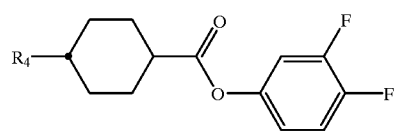 (7-2)
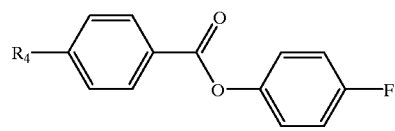 (7-3)
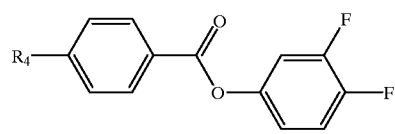 (7-4)
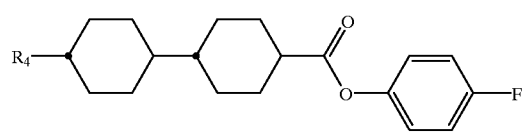 (7-5)

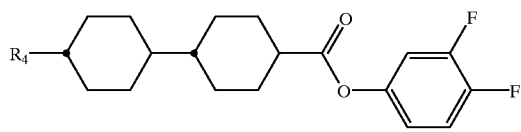 (7-6)
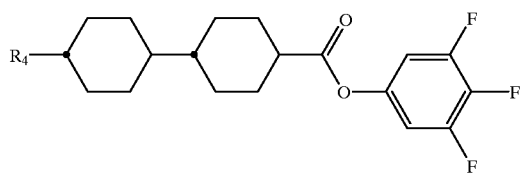 (7-7)
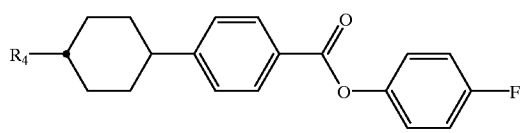 (7-8)
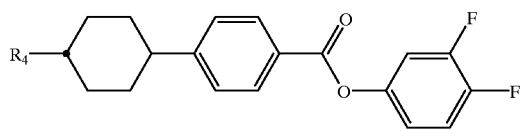 (7-9)
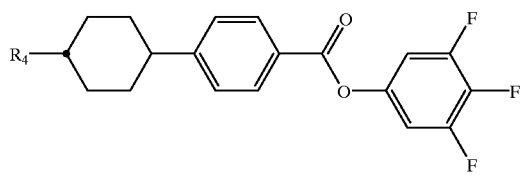 (7-10)
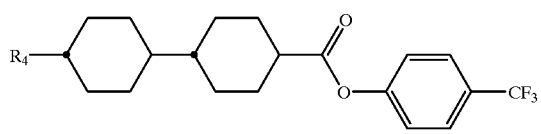 (7-11)
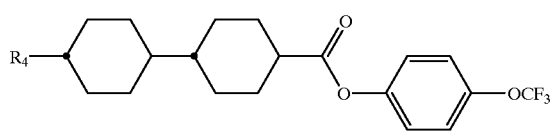 (7-12)
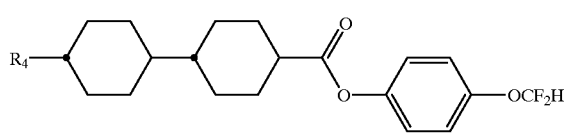 (7-13)
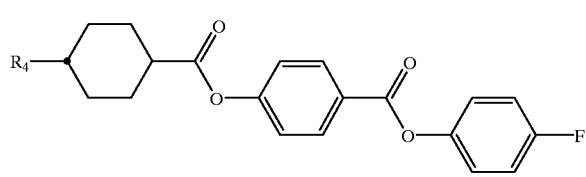 (7-14)

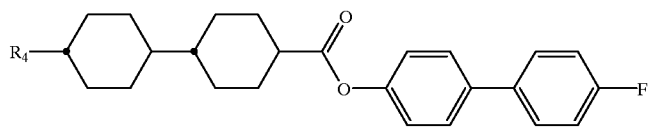
(7-15)
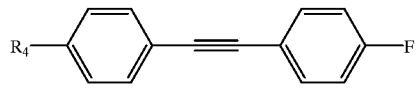
(7-16)
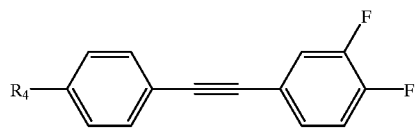
(7-17)
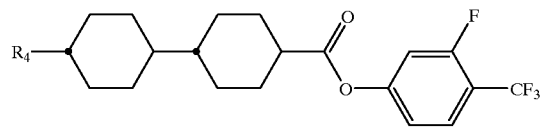
(7-18)
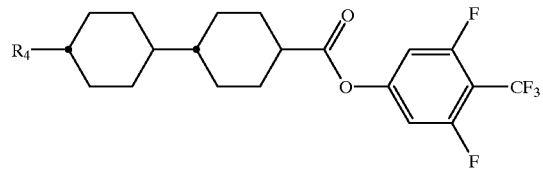
(7-19)
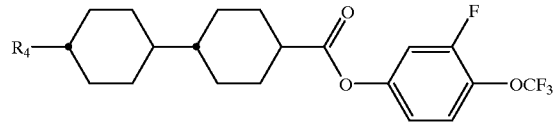
(7-20)
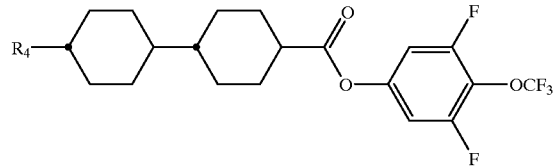
(7-21)
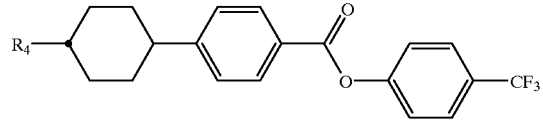
(7-22)
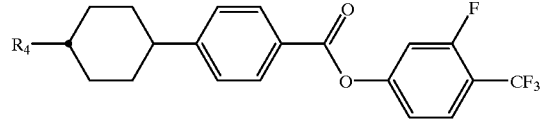
(7-23)

-continued

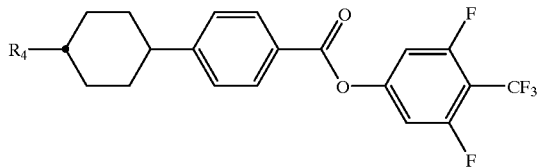
(7-24)

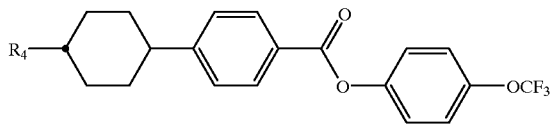
(7-25)

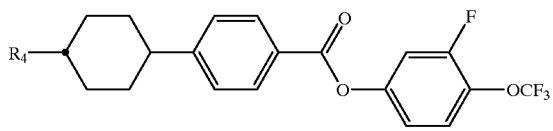
(7-26)

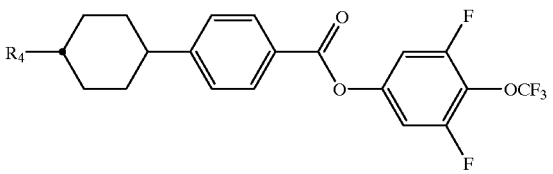
(7-27)

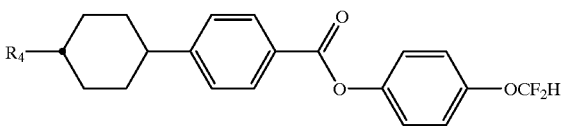
(7-28)

The compounds of the general formulas (5)–(7) show positive great values of dielectric anisotropy and are used for the purpose of minimizing the value of threshold voltage. The compounds are also used for the purpose of adjusting viscosity and values of optical anisotropy or of broadening the nematic range such as elevating the temperature of transparent point. Further, the compounds are used for the purpose of improving steepness of threshold voltage.

Illustrative of the compounds of the general formulas (8)–(9) are preferably the compounds shown by the following formulas wherein $R_5$–$R_8$ have the same meanings given above:

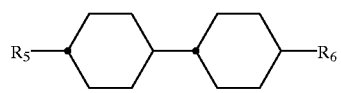
(8-1)

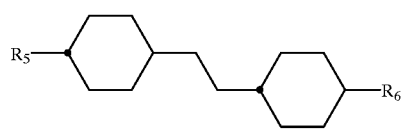
(8-2)

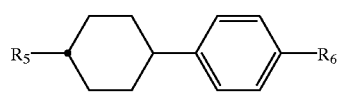
(8-3)

(8-4)
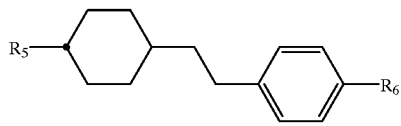
(8-5)
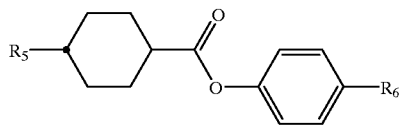
(8-6)
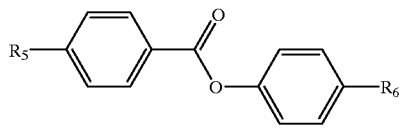
(8-7)
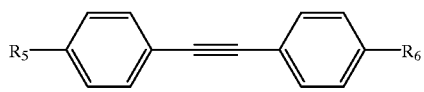
(8-8)
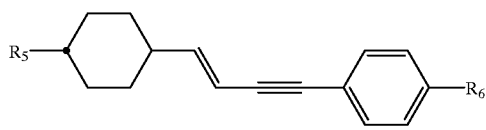
(9-1)
(9-2)
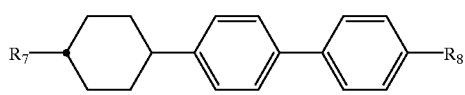
(9-3)
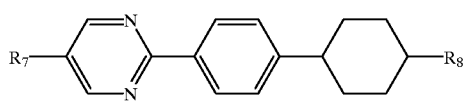
(9-4)
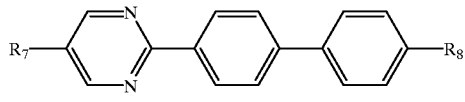
(9-5)
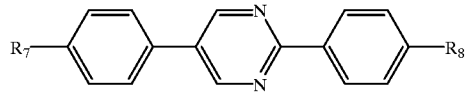
(9-6)
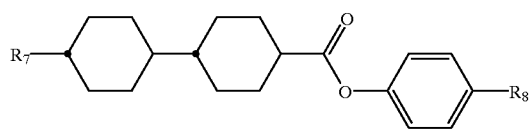

-continued (9-7)
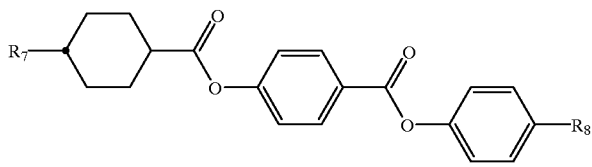

(9-8)
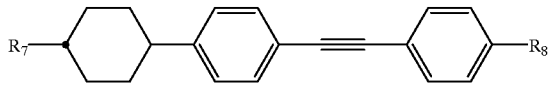

(9-9)
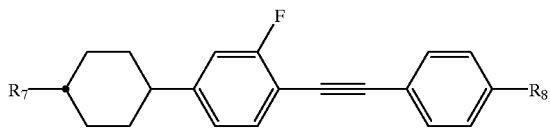

(9-10)
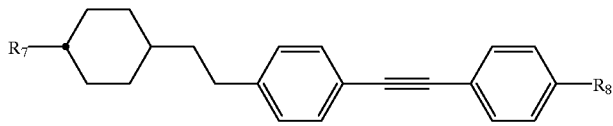

(9-11)
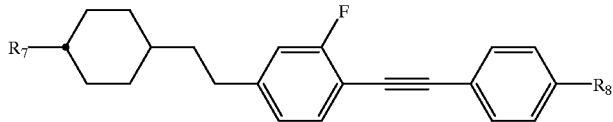

(9-12)
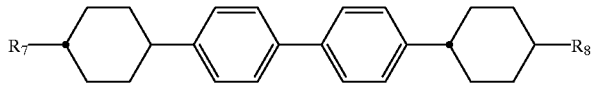

(9-13)
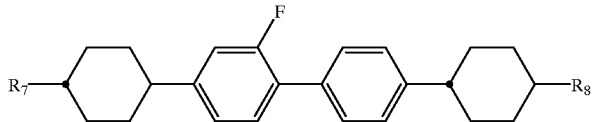

The compounds of the general formulas (8) and (9) show negative or slightly positive values of dielectric anisotropy. The compounds of the general formula (8) are chiefly used for the purpose f decreasing viscosity or adjusting the value of optical anisotropy. The compounds of the general formula (9) are used for the purpose of broadening the nematic range such as elevating the temperature of transparent point or of adjusting the values of optical anisotropy.

The compounds of the general formulas (5)–(9) are indispensable especially for preparing a liquid crystalline composition for use in STN display or TN display. In the preparation of a liquid crystalline composition for STN display or TN display, a compound of the general formulas (5)–(9) is properly used in an amount within the range of 1–99% by weight but is used preferably within the range of 10–97% by weight, more preferably 40–95% by weight. In this case, a part of the compounds represented by the general formulas (2)–(4) may be used together.

The liquid crystalline composition of the present invention is prepared in a conventional manner. In general, individual ingredients are dissolved together at a high temperature under reduced pressure but individual liquid crystalline compounds may be dissolved in organic solvents and mixed together and thereafter the solvents may be distilled off to prepare the composition.

The liquid crystalline composition is improved and optimized by incorporating therewith additives. These additives are widely known and actually described in detail in literatures. Usually, a chiral doping agent is added for inducing a spiral structure of liquid crystal, adjusting a twisted angle, and preventing counter-twist.

The liquid crystalline composition of the present invention can be incorporated with a dichromatic coloring agent such as merocyanine, azo, azomethine, azoxy, quinophthalone, anthraquinone, tetrazine or the like and used as a liquid crystalline composition for guest-host (G/H) mode. Alternatively, the liquid crystalline composition can also be used as a liquid crystalline composition for a polymer dispersion type liquid crystal display element (PDLCD) represented by NCAP made by micro-capsulation of nematic liquid crystals and a polymer network liquid crystal display element (PNLCD) wherein three-dimensional reticulated high molecules are formed in liquid crystals. In addition, the liquid crystalline composition can be used as a liquid crystalline composition for double refraction control (ECB) mode or dynamic scattering (DS) mode.

The liquid crystalline compounds of the general formula (1) can be produced according to an organic synthetic chemical procedure. For example, these compounds can be synthesized by properly combining the methods disclosed in literatures such as Organic Synthesis, Organic Reactions, Lecture of Experimental Chemistry and the like.

A compound of the general formula (1) wherein $B_1$ stands for the grouping —CH=CH— can be prepared according to the following route:

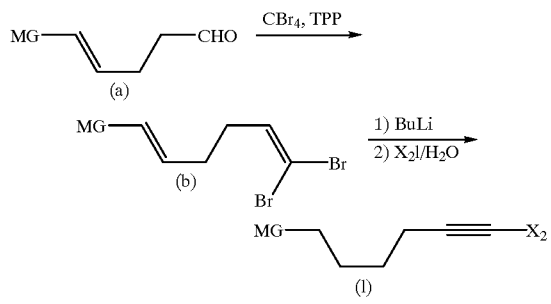

wherein MG stands for a mesogen (residue of an organic compound) represented by thee grouping:

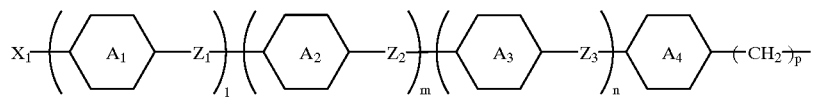

More precisely, a γ-δ unsaturated aldehyde (a) is reacted in the presence of triphenylphosphine (TPP) with carbon tetrabromide to form a dibromide (b) thereof. The dibromide is then reacted with butyl lithium followed by a halide to form a compound of the general formula (1). If water is used in place of the halide, a compound of the general formula (1) wherein $X_2$ stands for a hydrogen atom.

The γ, δ unsaturated aldehyde (a) can be prepared, for example, according to the following route:

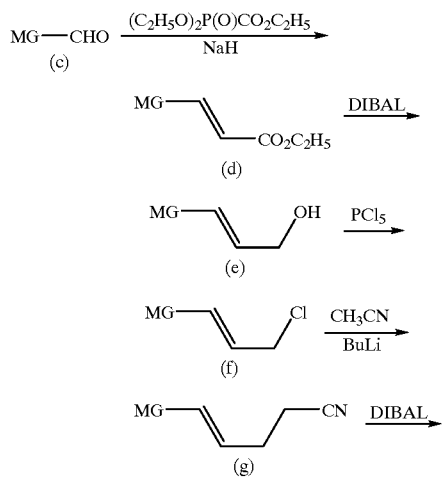

More precisely, an aldehyde (c) is subjected to Wittig-Honer reaction to form an α, β-unsaturated ester (d) which is reduced with diisobutylaluminum hydride (DIBAL) to form a β, γ-unsaturated alcohol (e). This compound (e) is chlorinated to form a compound (f) which is further reacted with butyllithium and acetonitrile to form a compound (g). Next, the compound (g) is reduced with DIBAL to form the compound (a).

The γ, δ-unsaturated aldehyde (a) can also be prepared according to the following route:

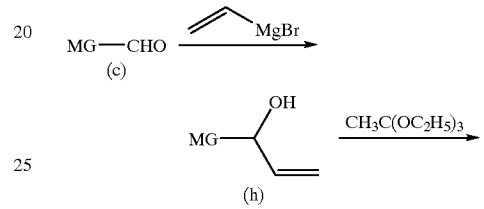

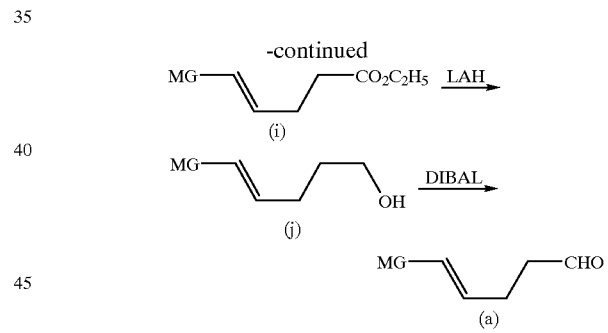

More precisely, the aldehyde (c) is reacted with vinylmagnesium bromide to form an α, β-unsaturated alcohol (h). The compound (h) is then reacted with ethyl carbonate to form a compound (i) which is further reacted with lithium aluminum hydride (LAH) to form an unsaturated alcohol (j). The compound (i) is reacted with an oxidizing agent such as pyridinium chlorochromate to form the α, β-unsaturated aldehyde (a).

A compound of the general formula (1) wherein $B_1$ stands for the grouping —C≡C— can be prepared using the aldehyde (c) as starting material according to the following route:

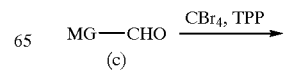

-continued

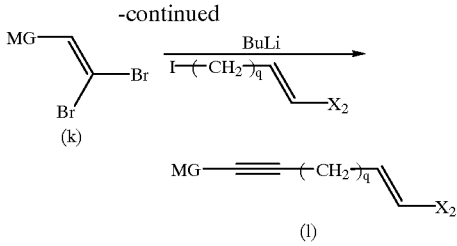

More precisely, the compound (c) is converted into a compound (k) according to the aforesaid condition and the latter is reacted with butyllithium and an alkenyl halide to form a compound of the general formula (1).

The elements constituting the compounds of the general formula (1) may be replaced by their isotopes (e.g. $_{12}C$ by $_{13}C$, H by D).

EXAMPLES

The present invention will now be illustrated in more detail by way of Examples. In these Examples, C stands for crystal, N for nematic phase, S for smectic phase and I for isotropic liquid, and the unit of phase transition temperature is shown by (° C.)

EXAMPLE 1

Preparation of 4-toluyl-4'-(hex-1-en-5-yl)bicyclohexane [the general formula (1) wherein $X_1$ stands for methyl group, $X_2$ stands for hydrogen atom, the ring $A_2$ stand for 1,4-phenylene, the rings $A_3$ and $A_4$ each stands for trans-1,4-cyclohexylene group, $Z_2$ and $Z_3$ together are a covalent bond, 1=p=0, m=n=1, q=1, $B_1$ stands for —CH=CH—, and $B_2$ stands for —C≡C—]

To 1.5 liters solution of ethyl diethylphosphonoacetate (0.78 mol) in tetrahydrofuran (THF) was added dropwise potassium t-butoxide in nitrogen atmosphere at a temperature below 0° C. After stirring the mixture for 2 hours at the same temperature, a 300 ml solution of 4-(4-toluyl-cyclohexyl)cyclohexane-carbonaldehyde (0.65 mol) in THF was added dropwise at the same temperature for 1 hour. After addition, the mixture was allowed to elevate temperature up to room temperature and continued for further 10 hours. One liter of water was then added to the reaction liquid and the mixture was extracted with ethyl acetate. The organic phase was washed with water and dried over anhydrous magnesium sulfate. Upon removal of the solvent by evaporation under reduced pressure, ethyl 3-(4-toluylbicyclohex-4'-yl) acrylate was obtained as a brown solid.

To 600 ml solution of the resultant acrylic derivative in toluene was added dropwise a 1M toluene solution of diisobutyl aluminum hydride (corres. to 1.35 mol) in nitrogen atmosphere at a temperature below 10° C. The mixture was warmed up to room temperature and stirred for 1.5 hours. The reaction liquid was again cooled and 500 ml of water and 500 ml of 6M-hydrochloric acid were then added dropwise to the liquid successively. After allowing the mixture to stand stationarily, the toluene layer was separated, washed with water, dried over anhydrous magnesium sulfate, and subjected to elimination of the solvent under reduced pressure, and then the residue was purified by way of column chromatography (eluent: dichloromethane/ethanol mixed solvent) to afford 3-(4-toluylbicyclohex-4'-yl)-2-propenol (0.62 mols) in 200 ml of dimethylformamide (DMF) was added dropwise in nitrogen atmosphere at room temperature. After stirring the mixture at room temperature for 3 hours, the reaction liquid was poured into 2 liters of water and the mixture was extracted with ethyl acetate. The organic phase was washed successively with water, a saturated aqueous solution of sodium bicarbonate and water, dried over anhydrous magnesium sulfate, and subjected to elimination of the solvent under reduced pressure, and the residue was purified by way of column chromatography (eluent: heptane) to give 3-(4-toluylbicyclohex-4'-yl)-chloroprop-2-ene (0.59 mol).

To a solution of 3-(4-toluylbicyclohex-4'-yl)-chloroprop-2-ene in 300 ml of THF was dropwise a 1 M solution of n-butyllithium in cyclohexane (corres. to 0.55 mol) in nitrogen atmosphere below –60° C. in 2 hours. After stirring the mixture for 2 hours at the same temperature, acetonitrile (0.53 mol) was added dropwise to the mixture and the whole was stirred for one hour at the same temperature. Water (200 ml) was added to the reaction mixture which was then extracted with ethyl acetate. The ethyl acetate layer was washed with water, dried over anhydrous magnesium sulfate, and subjected to removal of the solvent under reduced pressure to effect concentration of the extract. The concentrate was then purified by way of column chromatography (eluent: toluene/ethyl acetate mixed solvent) whereby 4-(4-toluylbicyclohex-4'-yl)-cyanobut-3-ene (0.29 mol) was obtained as colorless crystals.

To a mixture of 4-(4-toluylbicyclohex-4'-yl)-cyanobut-3-ene ) (0.25 mol) and 100 ml of toluene was added dropwise a 1 M toluene solution of diisobutylaluminum hydride (corres. to 0.25 mol) at a temperature below 10° C. The mixture was allowed to warm up to room temperature and stirred for 1.5 hours. The reaction solution was again cooled and 100 ml of water followed by 50 ml of 6 M hydrochloric acid was added dropwise to the reaction solution. After allowing the mixture to stand stationarily, the toluene layer was washed with water, dried over anhydrous magnesium sulfate, subjected to removal of the solvent conducted under reduced pressure, and the residue was purified by was of silica gel column chromatography (eluent: toluene) whereby 5-(4-toluylbicyclohex-4'-yl)pent-4-enal (0.20 mol), triphenyl-phosphine (0.25 mol), carbon tetrabromide (0.25 mol) and 100 ml of dichloromethane was stirred at room temperature all the day around. Water (50 ml) was added to the reaction mixture and the whole was stirred vigorously whereby the organic layer separated out was washed with water satisfactorily. The organic phase was dried over anhydrous magnesium sulfate and subjected to removal of the solvent under reduced pressure whereby 1,1-dibromo-6-(4-toluylbicyclohex-4'-yl)-1,5-pentadiene (0.12 mol) was obtained as a residual brown solid.

To a mixture of 1,1-dibromo-6-(4-tolylbicyclohex-4'-yl)-1,5-pentadiene (0.10 mol) and 190 ml of THF was added dropwise a 1.6 M hexane solution of butyl lithium (corres. to 0.22 mol) at 31 78° C., and the whole was stirred for one hour at the same temperature. Water (50 ml) was added to the reaction mixture and the whole was slowly warmed up to room temperature and stirred for 30 minutes at the same temperature. Water (200 ml) was added to the reaction mixture and the organic phase separated out was well washed with water and dried over anhydrous magnesium sulfate. The solvent was eliminated under reduced pressure and the residue was purified by way of column chromatography (eluent: heptane) followed by recrystallization (solvent: ethanol/hexane mixed solvent) whereby the title compound (0.07 mol) was obtained. The structure of this compound was identified by various spectral data.

Example 2

In accordance with the procedure illustrated in Example 1, the following compounds of the present invention represented by the general formula (1-1) were prepared:

$$-\left(\!\!\left\langle\!\! A_1 \!\!\right\rangle\!\!-Z_1\!\!\right)_{\!l}\!\!\left(\!\!\left\langle\!\! A_2 \!\!\right\rangle\!\!-Z_2\!\!\right)_{\!m}\!\!\left(\!\!\left\langle\!\! A_3 \!\!\right\rangle\!\!-Z_3\!\!\right)_{\!n}\!\!\left\langle\!\! A_4 \!\!\right\rangle\!\!-$$

| $X_1$ | | W | $X_2$ | |
|---|---|---|---|---|
| $C_3H_7$ | 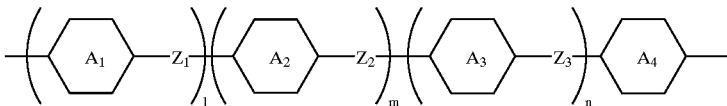 | W01 | H | |
| $C_3H_7$ | 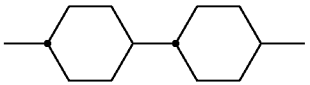 | W02 | H | |
| $C_5H_{11}$ | 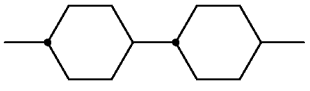 | W02 | H | SB 87.4N 110.2I |
| $C_3H_7$ | 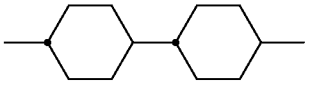 | W02 | $CH_3$ | |
| $C_3H_7$ |  | W03 | H | |
| $C_3H_7$ | 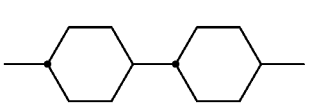 | W05 | H | |
| $C_3H_7$ | 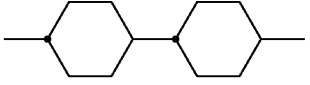 | W(01) | H | |
| $C_3H_7$ | 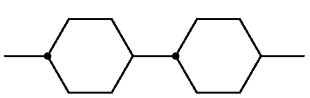 | W(02) | $CH_3$ | |
| $C_3H_7$ | 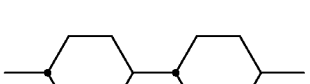 | W(02) | $C_3H_7$ | |
| $C_3H_7$ | 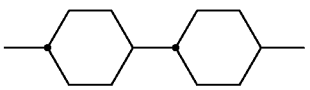 | W(03) | H | |
| $C_3H_7$ | 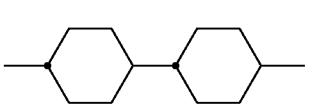 | W(04) | H | |

6,015,508
-continued
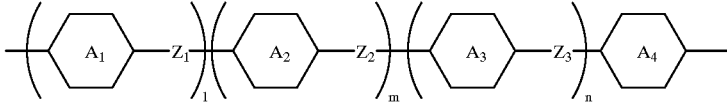
| $X_1$ | | W | $X_2$ |
|---|---|---|---|
| $C_3H_7$ | 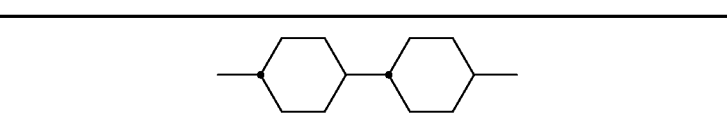 | W(05) | $CH_3$ |
| $C_3H_7$ | 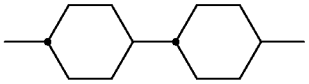 | W(05) | $C_2H_5$ |
| $C_3H_7$ | 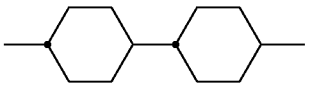 | W02 | H |
| $C_3H_7$ | 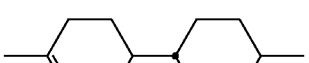 | W11 | H |
| $C_3H_7$ | 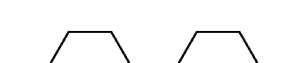 | W12 | $CH_3$ |
| $C_3H_7$ |  | W31 | H |
| $C_3H_7O$ |  | W(31) | H |
| $C_3H_7$ |  | W(15) | $CH_3$ |
| $F(CH_2)_2$ |  | W(35) | H |
| $CH_3OCH_2$ | 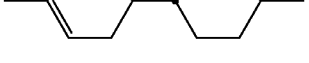 | W(55) | H |
| $C_3H_7$ | 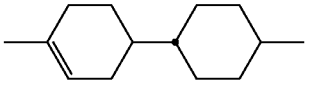 | W02 | H |

-continued $$-\left(\boxed{A_1}-Z_1\right)_l-\left(\boxed{A_2}-Z_2\right)_m-\left(\boxed{A_3}-Z_3\right)_n-\boxed{A_4}-$$

| $X_1$ | | W | $X_2$ |
|---|---|---|---|
| $C_5H_{11}$ | -⌬-CH$_2$CH$_2$-⌬- | W02 | $CH_3$ |
| $C_5H_{11}$ | -⌬-CH$_2$CH$_2$-⌬- | W02 | H |
| $C_3H_7$ | -⌬-CH$_2$CH$_2$-⌬- | W(02) | $CH_3$ |
| $C_3H_7$ | -⌬-CH=CH-⌬- | W02 | H |
| $C_3H_7$ | -⌬-CH=CH-⌬- | W(02) | H |
| $C_3H_7OCH_2$ | -⌬-CH=CH-⌬- | W(02) | $CH_3$ |
| $C_3H_7$ | -⌬-(CH$_2$)$_4$-⌬- | W02 | $CH_3$ |
| $C_3H_7$ | -(dioxane)-⌬- | W02 | H |
| $C_3H_7$ | -(dioxane)-⌬- | W41 | $CH_3$ |
| $C_3H_7$ | -(dioxane)-⌬(phenyl)- | W21 | H |
| $C_5H_{11}$ | -(dioxane)-⌬(phenyl)- | W22 | $CH_3$ |

-continued
| | | | |
|---|---|---|---|
| X₁ | structure | W | X₂ |
| C₃H₇O | 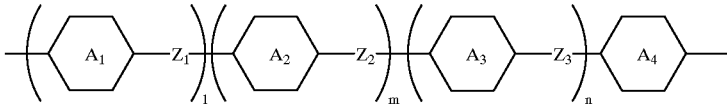 | W(22) | H |
| F(CH₂)₂ | 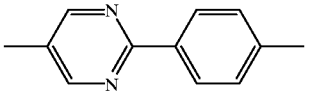 | W(22) | CH₃ |
| C₃H₇ | 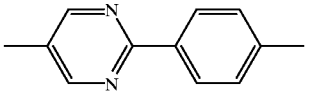 | W02 | H |
| F | 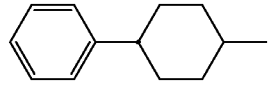 | W02 | CH₃ |
| C₅H₁₁ | 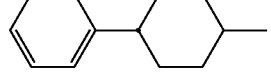 | W(02) | H |
| C₃H₇ | 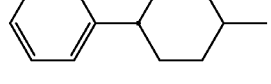 | W(02) | CH₃ |
| NC | 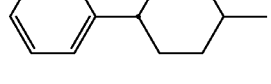 | W02 | H |
| NC | 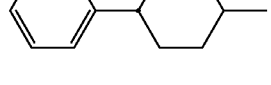 | W(01) | H    C52.0I |
| F | 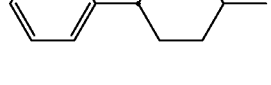 | W02 | H |
| F | 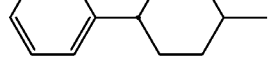 | W02 | CH₃ |
| NC | 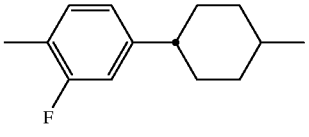 | W02 | H |

-continued
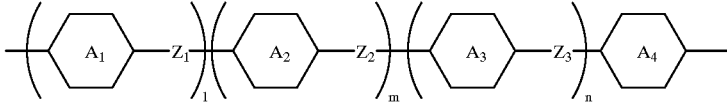
| $X_1$ | | W | $X_2$ |
|---|---|---|---|
| $C_3H_7$ |  | W02 | $CH_3$ |
| $C_3H_7$ | 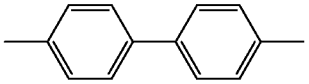 | W02 | $C_2H_5$ |
| $C_3H_7O$ | 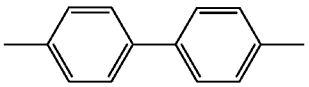 | W02 | H |
| $C_3H_7$ | 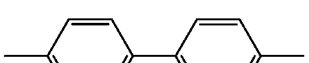 | W22 | H |
| $C_3H_7$ | 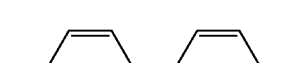 | W22 | $CH_3$ |
| NC |  | W22 | H |
| F | 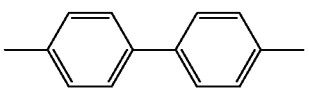 | W22 | H |
| F | 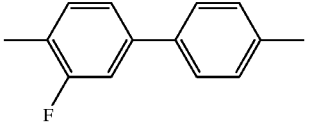 | W22 | H |
| $C_3H_7$ | 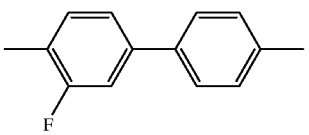 | W02 | H |
| $C_3H_7$ |  | W02 | $CH_3$ |
| $C_5H_{11}$ | 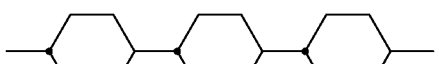 | W(01) | H |

| | | | |
|---|---|---|---|
| | 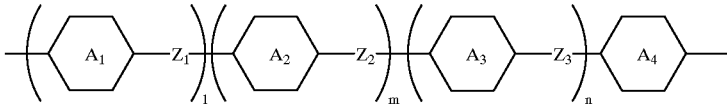 | | |
| $X_1$ | | W | $X_2$ |
| $C_3H_7$ |  | W(01) | $CH_3$ |
| $C_3H_7$ | 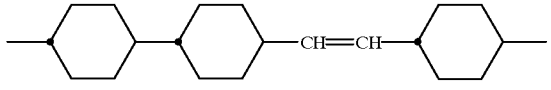 | W02 | H |
| $C_3H_7$ | 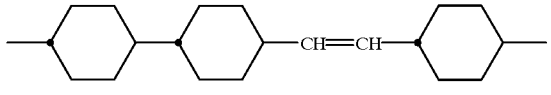 | W21 | H |
| $C_3H_7$ | 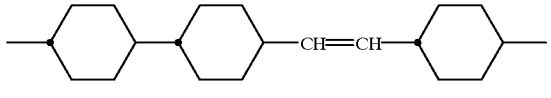 | W(01) | H |
| $C_3H_7$ | 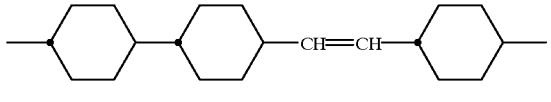 | W(02) | $CH_3$ |
| $C_3H_7$ | 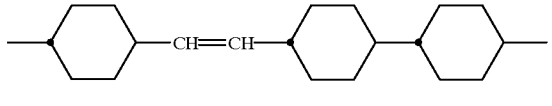 | W22 | H |
| $C_3H_7$ | 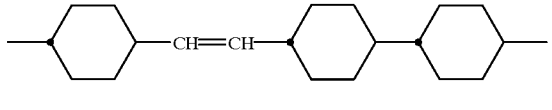 | W(21) | H |
| $C_3H_7$ | 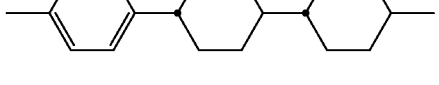 | W01 | H |
| $C_3H_7$ | 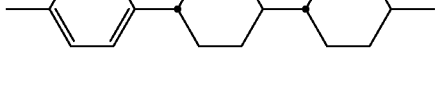 | W02 | $CH_3$ |
| F | 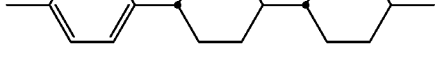 | W02 | $C_2H_5$ |
| NC | 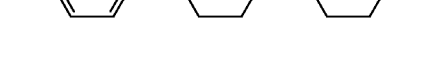 | W02 | H |

-continued
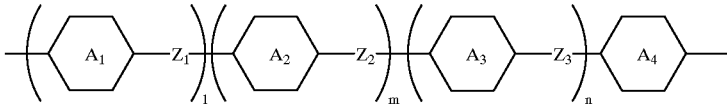
| $X_1$ | | W | $X_2$ |
|---|---|---|---|
| $C_3H_7$ |  | W(01) | H |
| F | 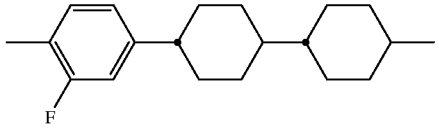 | W22 | H |
| $CF_3O$ | 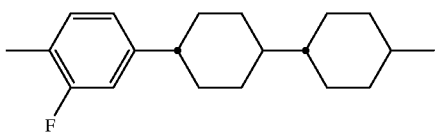 | W22 | $CH_3$ |
| F | 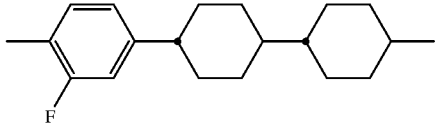 | W22 | H |
| $C_3H_7$ | 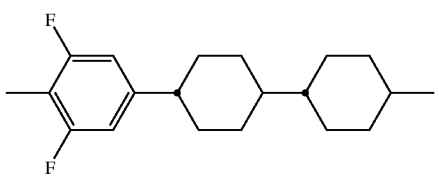 | W02 | H |
| $C_3H_7$ | 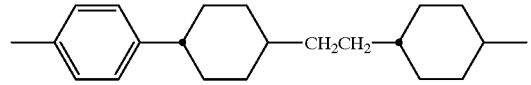 | W21 | H |
| $C_5H_{11}$ | 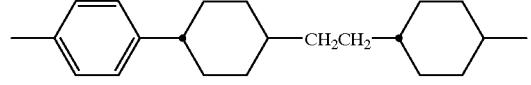 | W02 | $CH_3$ |
| $C_3H_7$ | 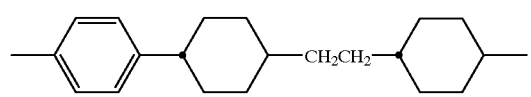 | W22 | $CH_3$ |
| F | 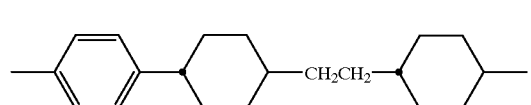 | W02 | H |
| NC | 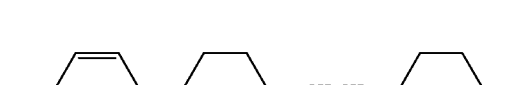 | W02 | H |

-continued
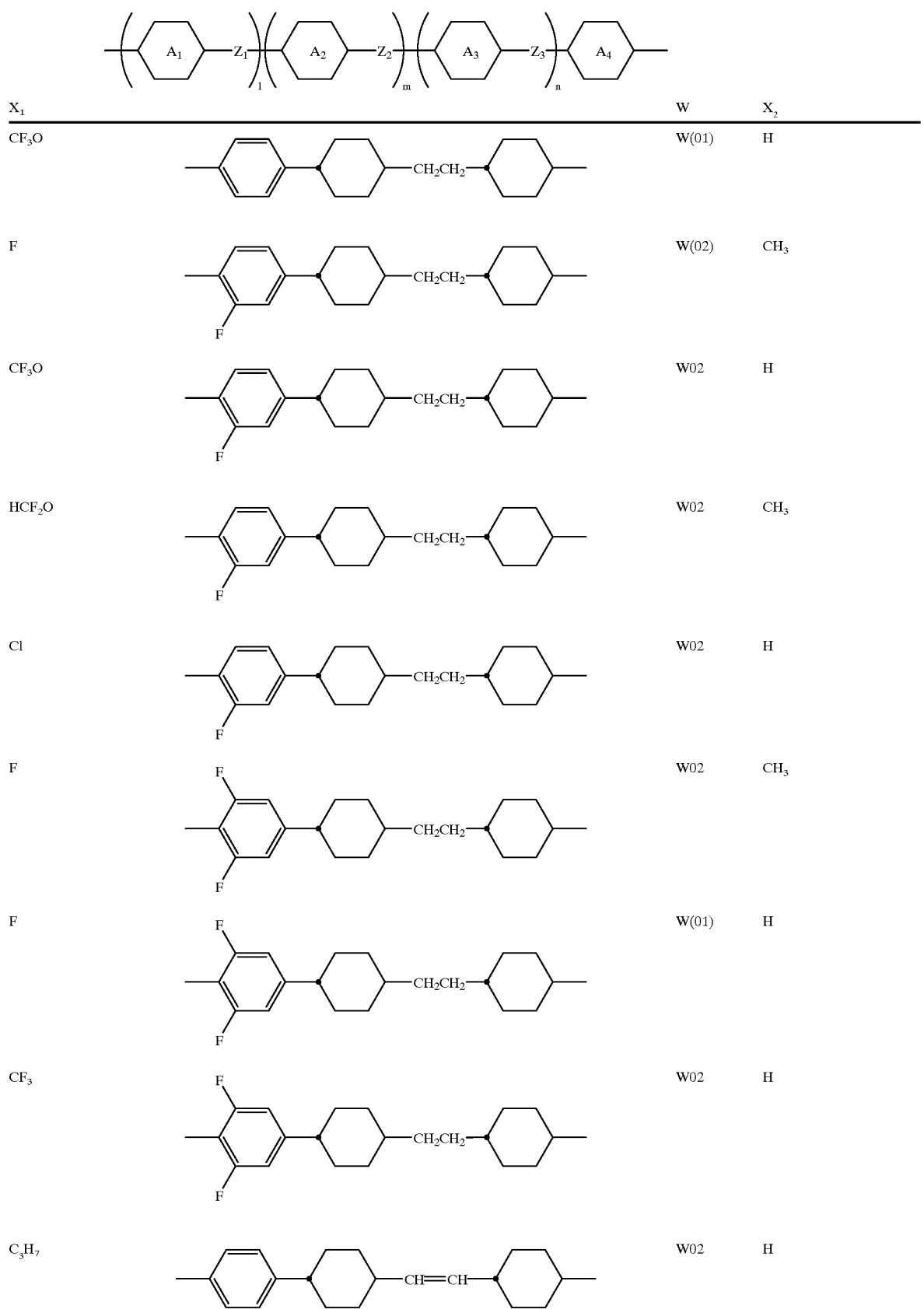
| $X_1$ | | W | $X_2$ |
|---|---|---|---|
| CF$_3$O | | W(01) | H |
| F | | W(02) | CH$_3$ |
| CF$_3$O | | W02 | H |
| HCF$_2$O | | W02 | CH$_3$ |
| Cl | | W02 | H |
| F | | W02 | CH$_3$ |
| F | | W(01) | H |
| CF$_3$ | | W02 | H |
| C$_3$H$_7$ | | W02 | H |

-continued
$$\mbox{---}\!\!\left(\!\!\boxed{A_1}\!\!-\!Z_1\!\right)_{\!l}\!\!\left(\!\!\boxed{A_2}\!\!-\!Z_2\!\right)_{\!m}\!\!\left(\!\!\boxed{A_3}\!\!-\!Z_3\!\right)_{\!n}\!\!\boxed{A_4}\!\!\mbox{---}$$
| $X_1$ | | W | $X_2$ |
|---|---|---|---|
| $C_3H_7$ | 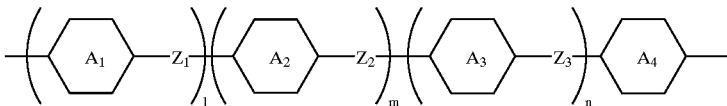 | W21 | H |
| $C_5H_{11}$ | 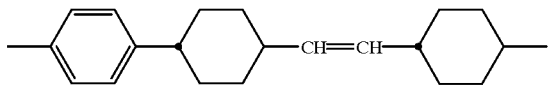 | W02 | $CH_3$ |
| $C_3H_7$ | 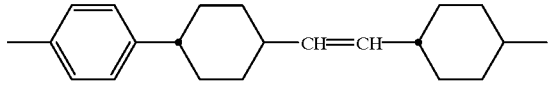 | W22 | $CH_3$ |
| F | 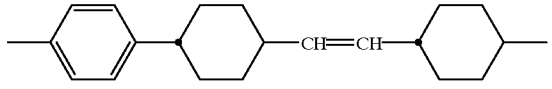 | W02 | H |
| NC | 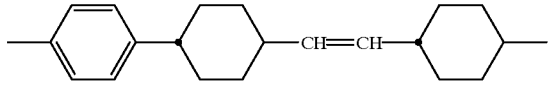 | W02 | H |
| $CF_3O$ | 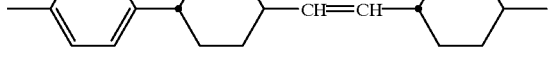 | W(01) | H |
| F | 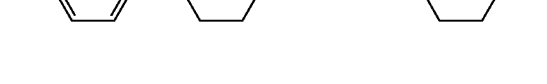 | W(02) | $CH_3$ |
| $CF_3O$ | 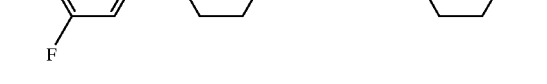 | W02 | H |
| $HCF_2O$ | 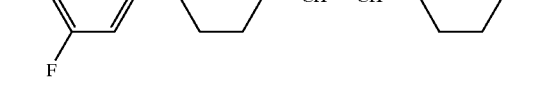 | W02 | $CH_3$ |
| Cl | 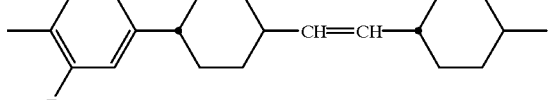 | W02 | H |

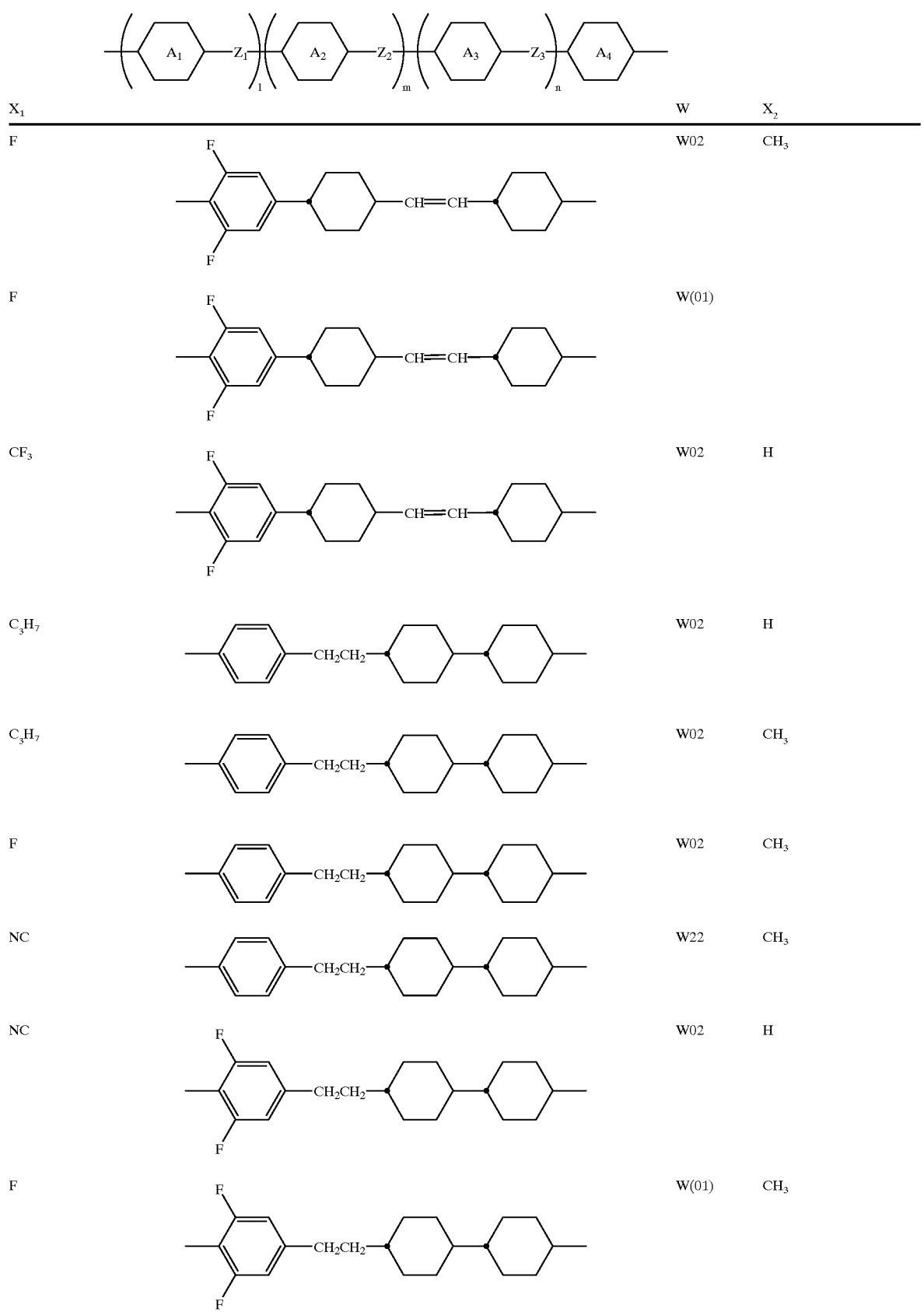

-continued

| $X_1$ | $\left(\!\!\left(\!\!\begin{array}{c}A_1\end{array}\!\!\right)\!\!-\!Z_1\!-\!\right)_{\!l}\!\left(\!\!\left(\!\!\begin{array}{c}A_2\end{array}\!\!\right)\!\!-\!Z_2\!-\!\right)_{\!m}\!\left(\!\!\left(\!\!\begin{array}{c}A_3\end{array}\!\!\right)\!\!-\!Z_3\!-\!\right)_{\!n}\!\left(\!\!\begin{array}{c}A_4\end{array}\!\!\right)\!\!-$ | W | $X_2$ |
|---|---|---|---|
| $C_5H_{11}$ | 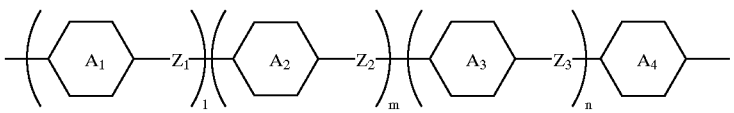 | W02 | H |
| $C_3H_7$ |  | W02 | $CH_3$ |
| Cl | 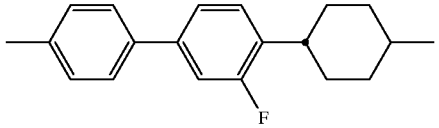 | W02 | H |
| F | 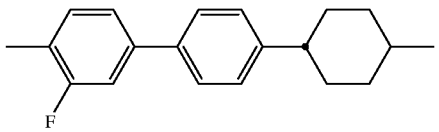 | W02 | $CH_3$ |
| F | 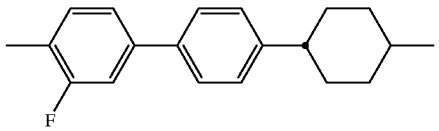 | W(01) | $C_2H_5$ |
| $CF_3O$ | 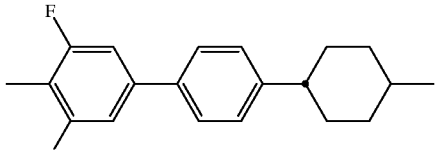 | W02 | H |
| $C_3H_7$ | 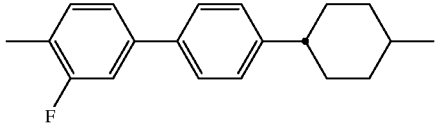 | W01 | H |
| $C_2H_7$ | 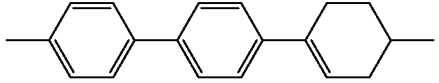 | W02 | H |
| F |  | W02 | H |

-continued
| X₁ | (structure) | W | X₂ |
|---|---|---|---|
| C₃H₇ | 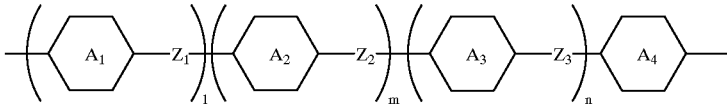 | W02 | H |
| C₃H₇ | 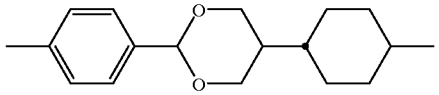 | W(01) | H |
| F | 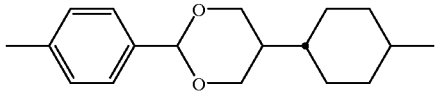 | W(02) | C₃H₇ |
| C₃H₇ | 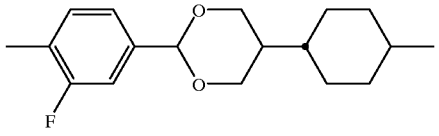 | W02 | H |
| C₃H₇ | 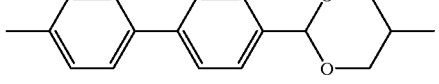 | W(01) | CH₃ |
| F | 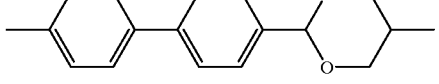 | W11 | H |
| C₃H₇ | 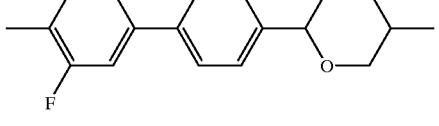 | W02 | H |
| C₃H₇ | 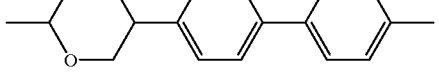 | W(15) | CH₃ |
| F(CH₂)₂ | 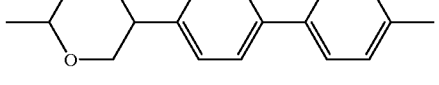 | W02 | H |
| C₃H₇ | 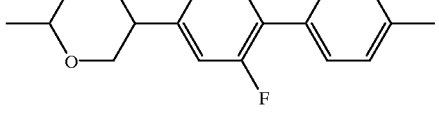 | W01 | H |

-continued $$-\left(\!\!\left(\!\!\begin{array}{c}A_1\end{array}\!\!\right)\!\!-Z_1\!\!\right)_{\!l}\!\!\left(\!\!\left(\!\!\begin{array}{c}A_2\end{array}\!\!\right)\!\!-Z_2\!\!\right)_{\!m}\!\!\left(\!\!\left(\!\!\begin{array}{c}A_3\end{array}\!\!\right)\!\!-Z_3\!\!\right)_{\!n}\!\!\left(\!\!\begin{array}{c}A_4\end{array}\!\!\right)\!\!-$$

| $X_1$ | | W | $X_2$ |
|---|---|---|---|
| $C_5H_{11}$ | 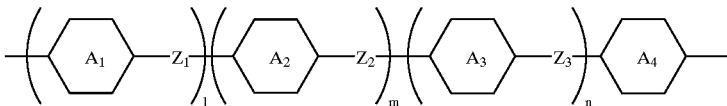 | W02 | H |
| $C_3H_7$ | 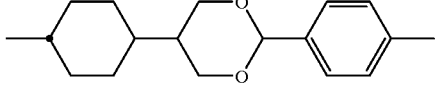 | W02 | $C_2H_5$ |
| $C_3H_7$ | 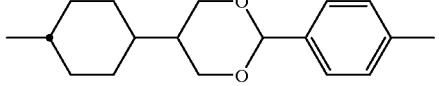 | W(01) | H |
| $C_5H_{11}$ | 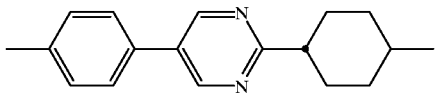 | W02 | H |
| $C_3H_7$ | 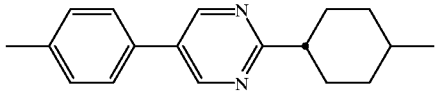 | W02 | $CH_3$ |
| $C_3H_7$ | 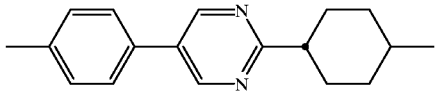 | W(01) | $CH_3$ |
| $C_3H_7$ | 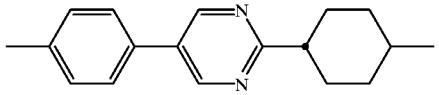 | W02 | H |
| $C_3H_7$ | 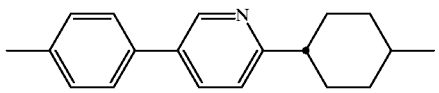 | W02 | $CH_3$ |
| $C_3H_7$ | 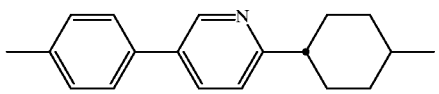 | W(01) | $CH_3$ |
| $F(CH_2)_2$ | 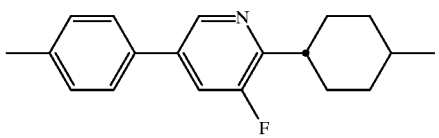 | W02 | H |

-continued
| | | | |
|---|---|---|---|
| X₁ | (structure) | W | X₂ |
| C₃H₇ | 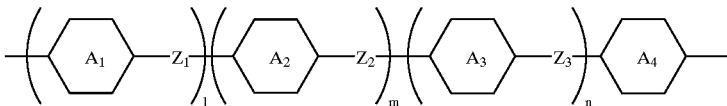 | W01 | H |
| C₅H₁₁ |  | W02 | H |
| C₃H₇ |  | W02 | C₂H₅ |
| C₃H₇ |  | W(01) | H |
| C₅H₁₁ |  | W42 | H |
| C₃H₇ |  | W(42) | CH₃ |
| C₃H₇ |  | W(01) | CH₃ |
| C₃H₇ |  | W02 | H |
| C₃H₇ | 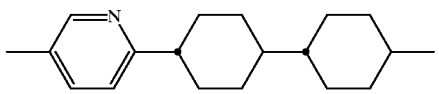 | W02 | CH₃ |
| C₃H₇ | 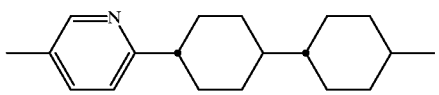 | W(01) | CH₃ |

-continued
| | | | |
|---|---|---|---|
| $X_1$ | structure | W | $X_2$ |
| $F(CH_2)_2$ | 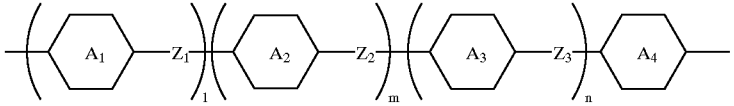 | W02 | H |
| $C_3H_7$ | 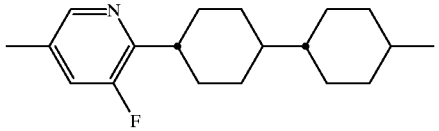 | W02 | H |
| $C_5H_{11}$ | 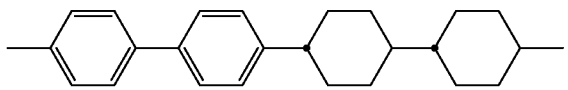 | W02 | $CH_3$ |
| F | 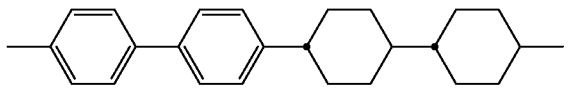 | W02 | $C_2H_5$ |
| F | 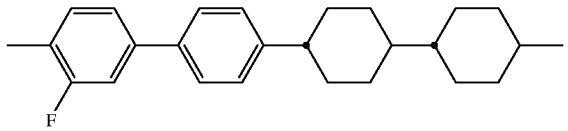 | W(01) | H |
| $C_5H_{11}$ | 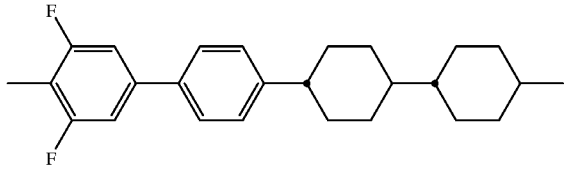 | W02 | H |
| $CF_3O$ | 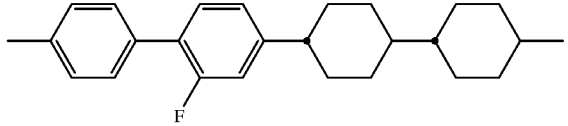 | W02 | $CH_3$ |
| $C_3H_7$ | 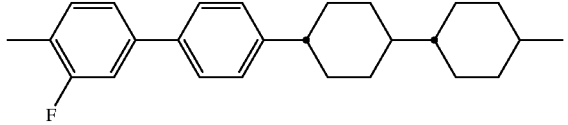 | W(01) | $CH_3$ |
| $C_3H_7$ | 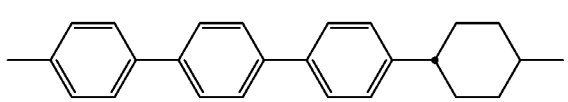 | W02 | H |

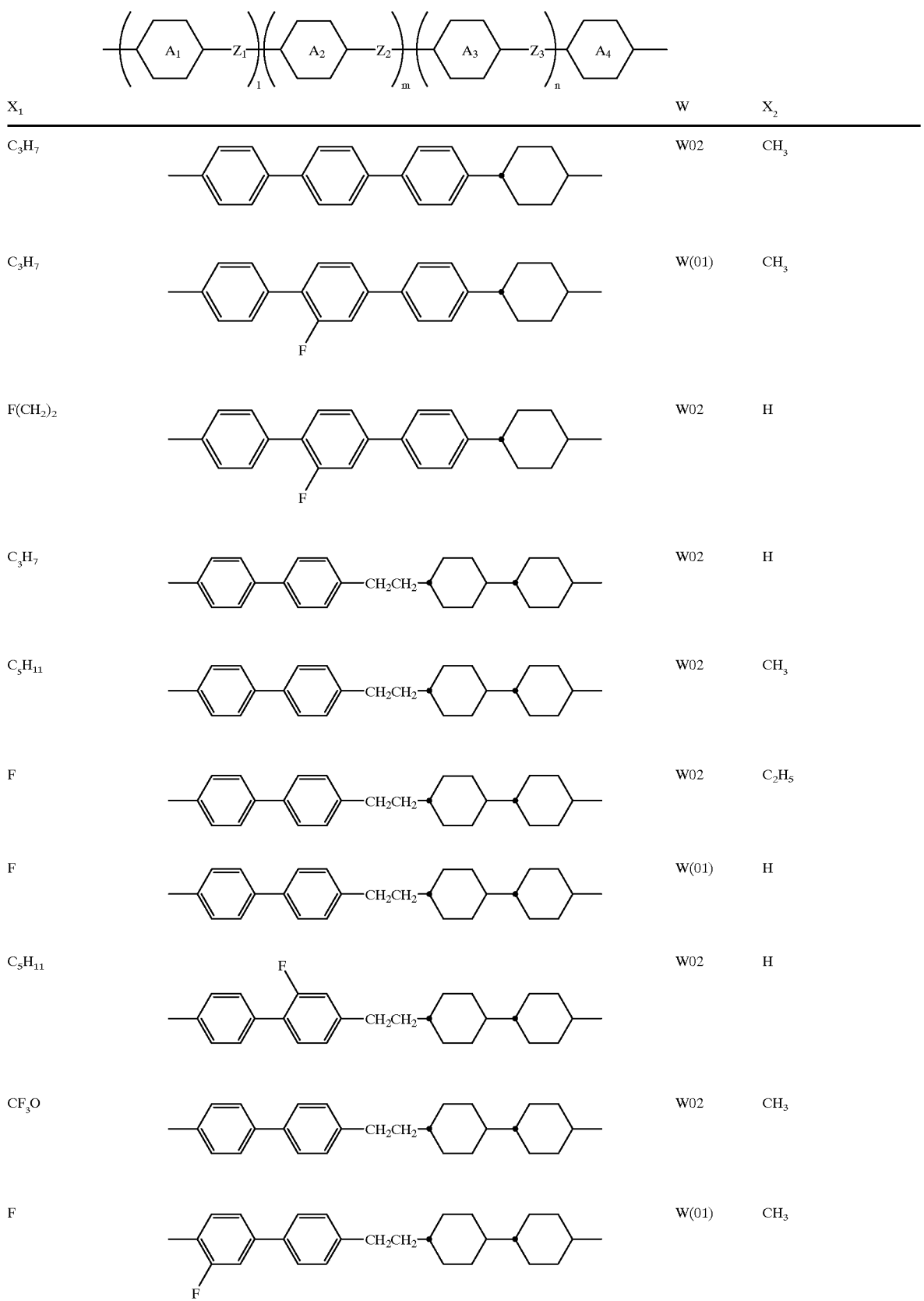

-continued
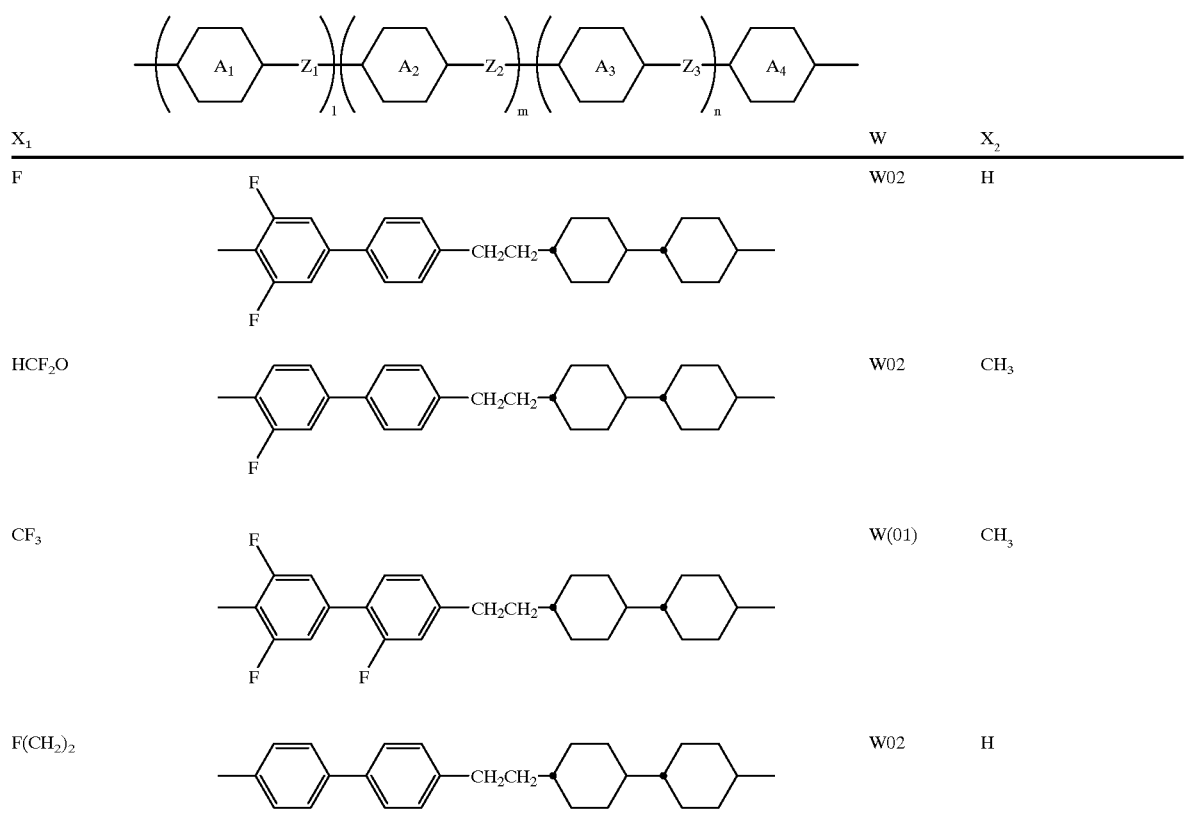
In these formulas, W stands for the grouping —(CH$_2$)$_p$—B$_1$—(CH$_2$)$_q$—B$_2$— and its various forms are abbreviated herein as W$_{01}$–W$_{55}$. These various forms are shown by the following:
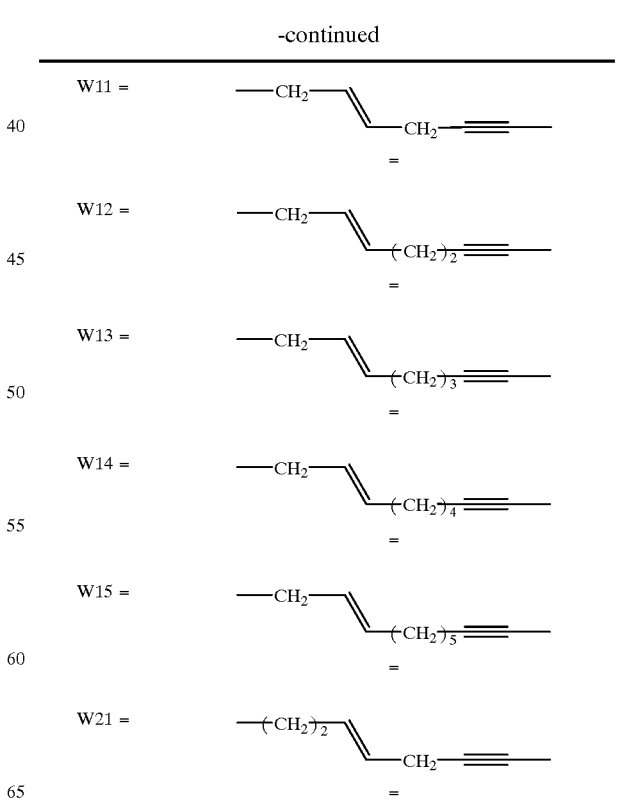

| | |
|---|---|
| W22 = | —(CH₂)₂—CH=CH—(CH₂)₂—C≡C— |
| W23 = | —(CH₂)₂—CH=CH—(CH₂)₃—C≡C— |
| W24 = | —(CH₂)₂—CH=CH—(CH₂)₄—C≡C— |
| W25 = | —(CH₂)₂—CH=CH—(CH₂)₅—C≡C— |
| W31 = | —(CH₂)₃—CH=CH—CH₂—C≡C— |
| W32 = | —(CH₂)₃—CH=CH—(CH₂)₂—C≡C— |
| W33 = | —(CH₂)₃—CH=CH—(CH₂)₃—C≡C— |
| W34 = | —(CH₂)₃—CH=CH—(CH₂)₄—C≡C— |
| W35 = | —(CH₂)₃—CH=CH—(CH₂)₅—C≡C— |
| W41 = | —(CH₂)₄—CH=CH—CH₂—C≡C— |
| W42 = | —(CH₂)₄—CH=CH—(CH₂)₂—C≡C— |
| W43 = | —(CH₂)₄—CH=CH—(CH₂)₃—C≡C— |
| W44 = | —(CH₂)₄—CH=CH—(CH₂)₄—C≡C— |
| W45 = | —(CH₂)₄—CH=CH—(CH₂)₅—C≡C— |
| W51 = | —(CH₂)₅—CH=CH—CH₂—C≡C— |
| W52 = | —(CH₂)₅—CH=CH—(CH₂)₂—C≡C— |
| W53 = | —(CH₂)₅—CH=CH—(CH₂)₃—C≡C— |
| W54 = | —(CH₂)₅—CH=CH—(CH₂)₄—C≡C— |
| W55 = | —(CH₂)₅—CH=CH—(CH₂)₅—C≡C— |
| W(01) = | —C≡C—CH₂—CH=CH— |
| W(02) = | —C≡C—(CH₂)₂—CH=CH— |
| W(03) = | —C≡C—(CH₂)₃—CH=CH— |
| W(04) = | —C≡C—(CH₂)₄—CH=CH— |
| W(05) = | —C≡C—(CH₂)₅—CH=CH— |
| W(11) = | —CH₂—C≡C—CH₂—CH=CH— |
| W(12) = | —CH₂—C≡C—(CH₂)₂—CH=CH— |
| W(13) = | —CH₂—C≡C—(CH₂)₃—CH=CH— |
| W(14) = | —CH₂—C≡C—(CH₂)₄—CH=CH— |
| W(15) = | —CH₂—C≡C—(CH₂)₅—CH=CH— |
| W(21) = | —(CH₂)₂—C≡C—(CH₂)₂—CH=CH— |

W(22) = 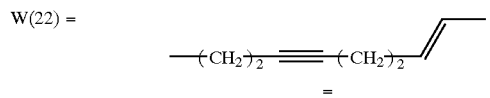
W(23) = 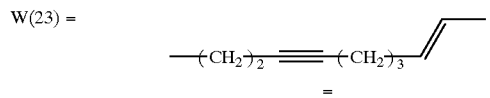
W(24) = 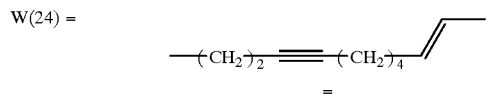
W(25) = 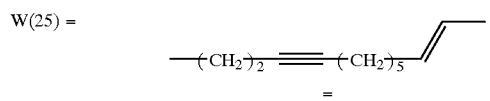
W(31) = 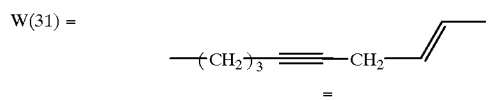
W(32) = 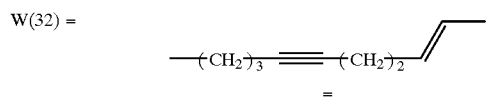
W(33) = 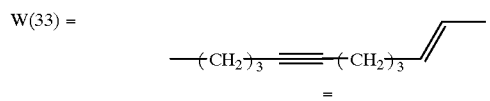
W(34) = 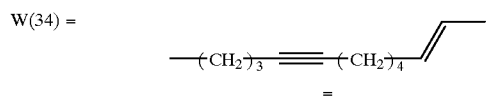
W(35) = 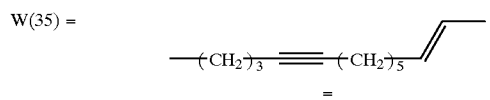
W(41) = 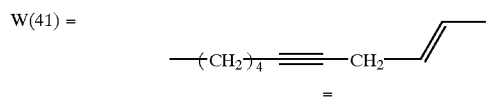
W(42) = 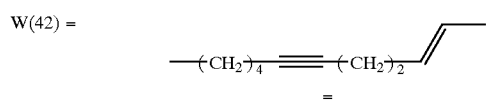
W(43) = 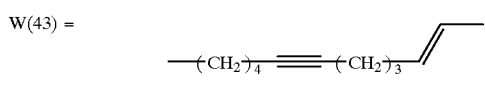
W(44) = 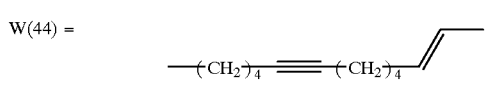
W(45) = 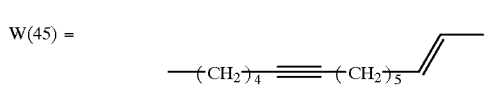
W(51) = 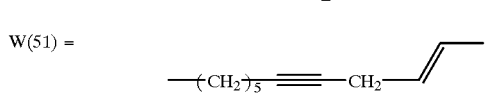
W(52) = 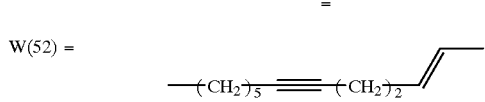
W(53) = 
W(54) = 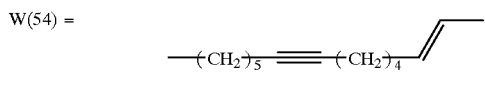
W(55) = 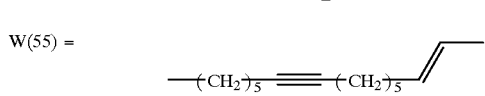
Example 3
In accordance with the procedure illustrated in Example 1, the following compounds of the present invention (1-2) were prepared:

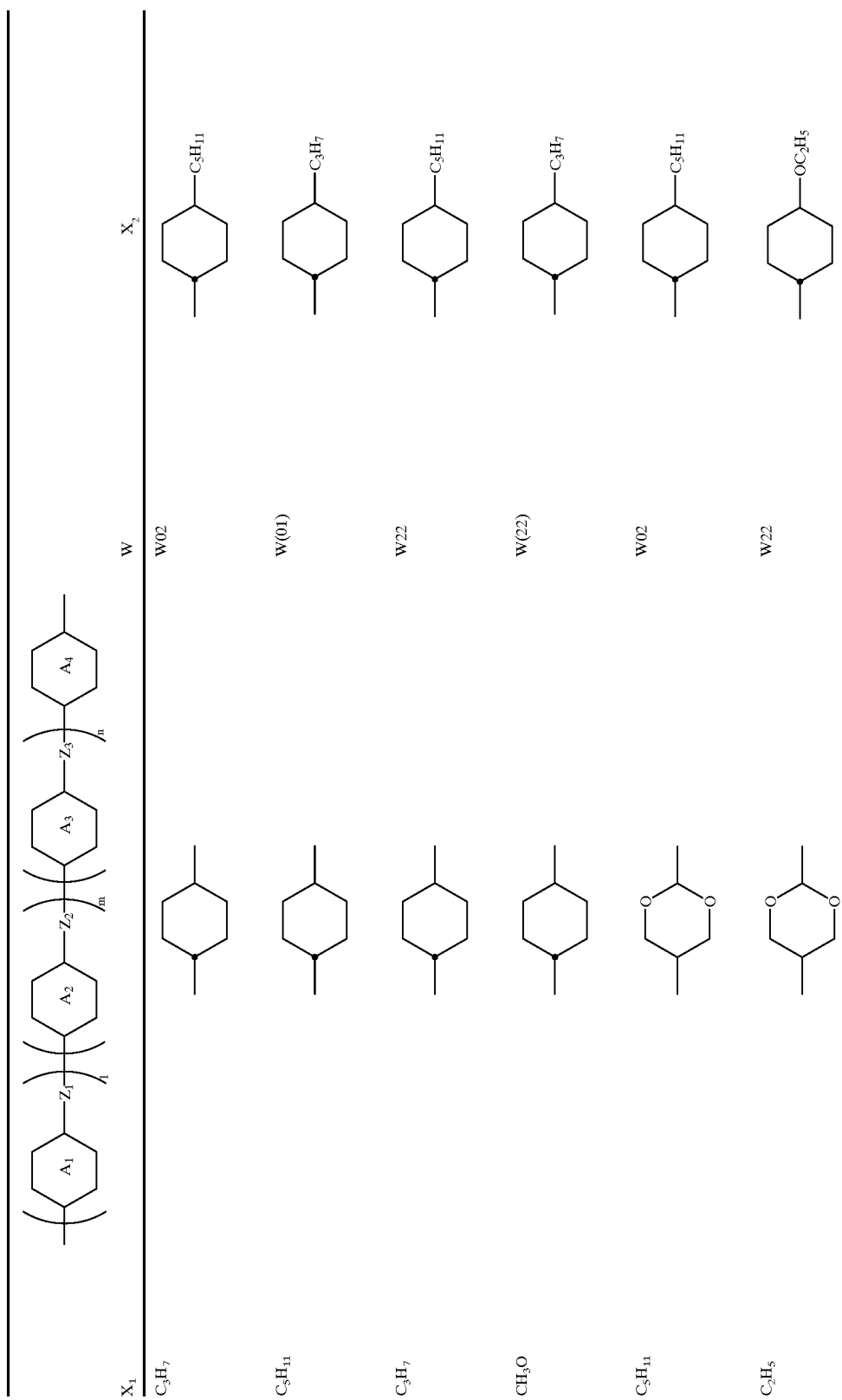

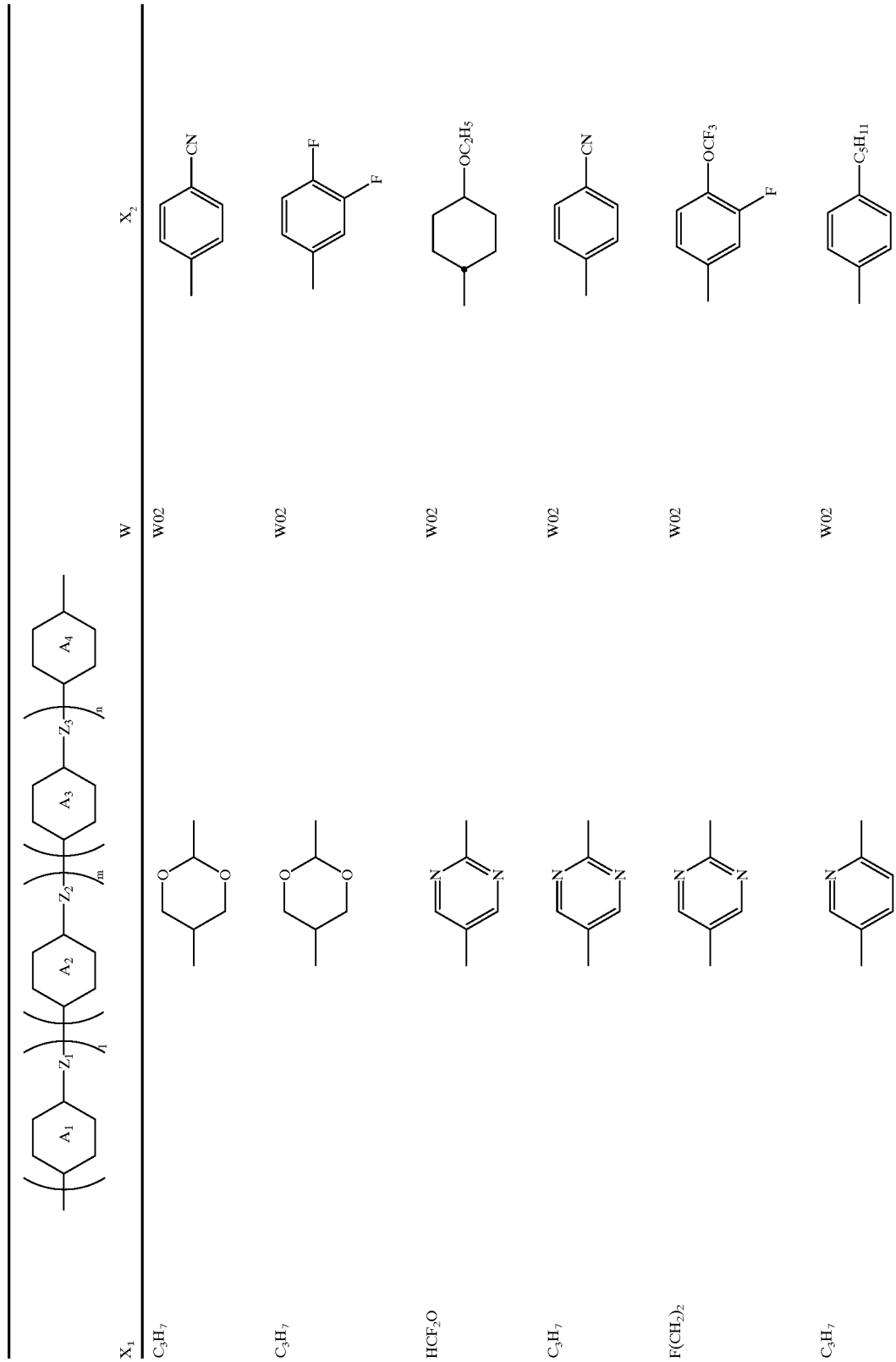

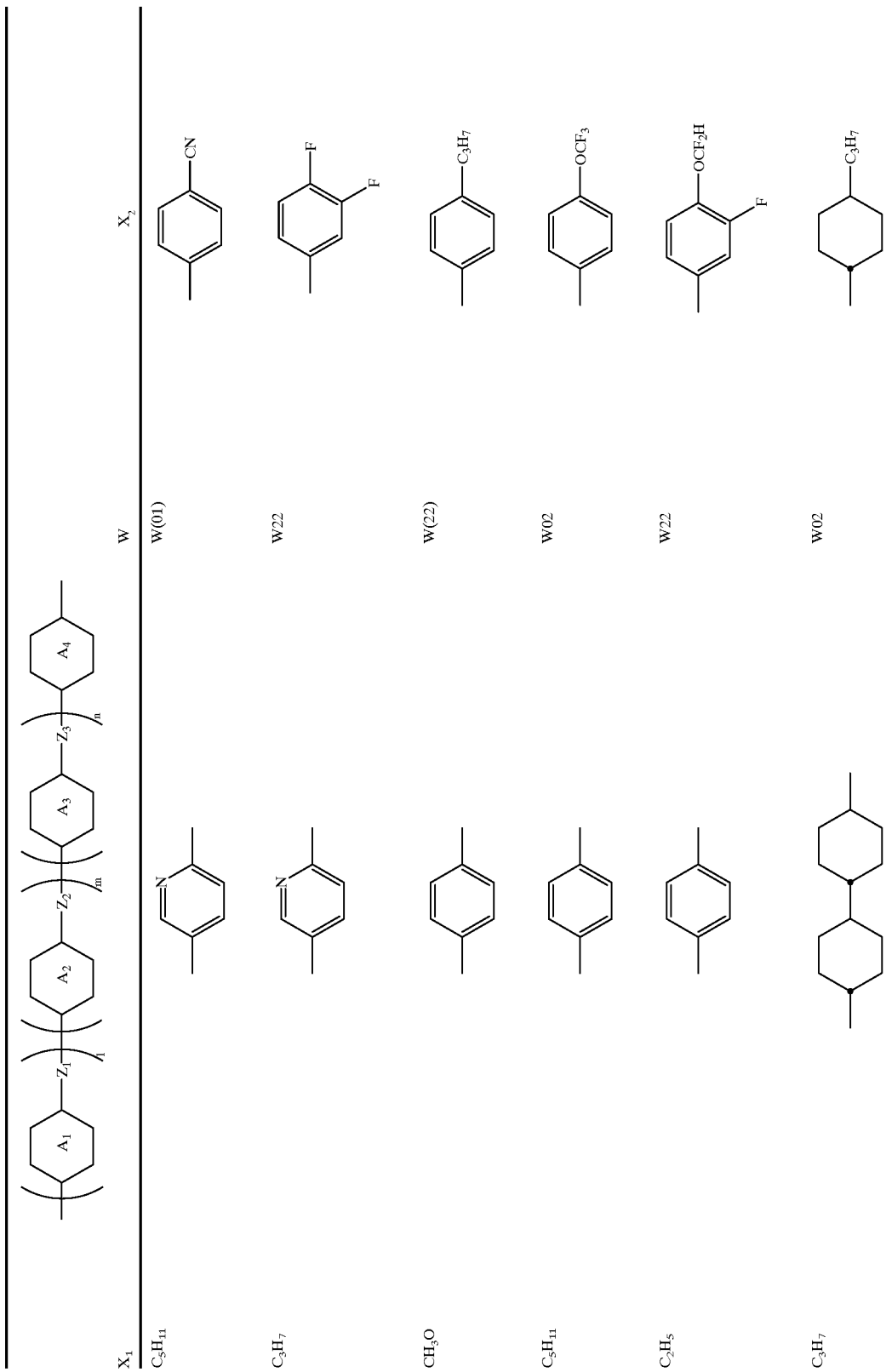

-continued

| $X_1$ | $A_1$-$(Z_1)_l$-$A_2$-$(Z_2)_m$-$A_3$-$(Z_3)_n$-$A_4$ | W | $X_2$ |
|---|---|---|---|
| $C_3H_7$ | Cy–Cy | W02 | Cy–$C_5H_{11}$ |
| $C_5H_{11}$ | Cy–Cy | W02 | Cy–$OC_2H_5$ |
| $C_3H_7$ | Cy–CH=CH–Cy | W02 | Cy–$C_3H_7$ |
| $F(CH_2)_2$ | Cy–CH=CH–Cy | W02 | Cy–CH=$CH_2$ |
| $C_3H_7$ | Cy–Ph | W02 | Cy–$C_3H_7$ |
| $C_5H_{11}$ | Cy–Ph | W(01) | Cy–CH=$CH_2$ |
| NC | Cy–Ph | W22 | Cy–$C_3H_7$ |

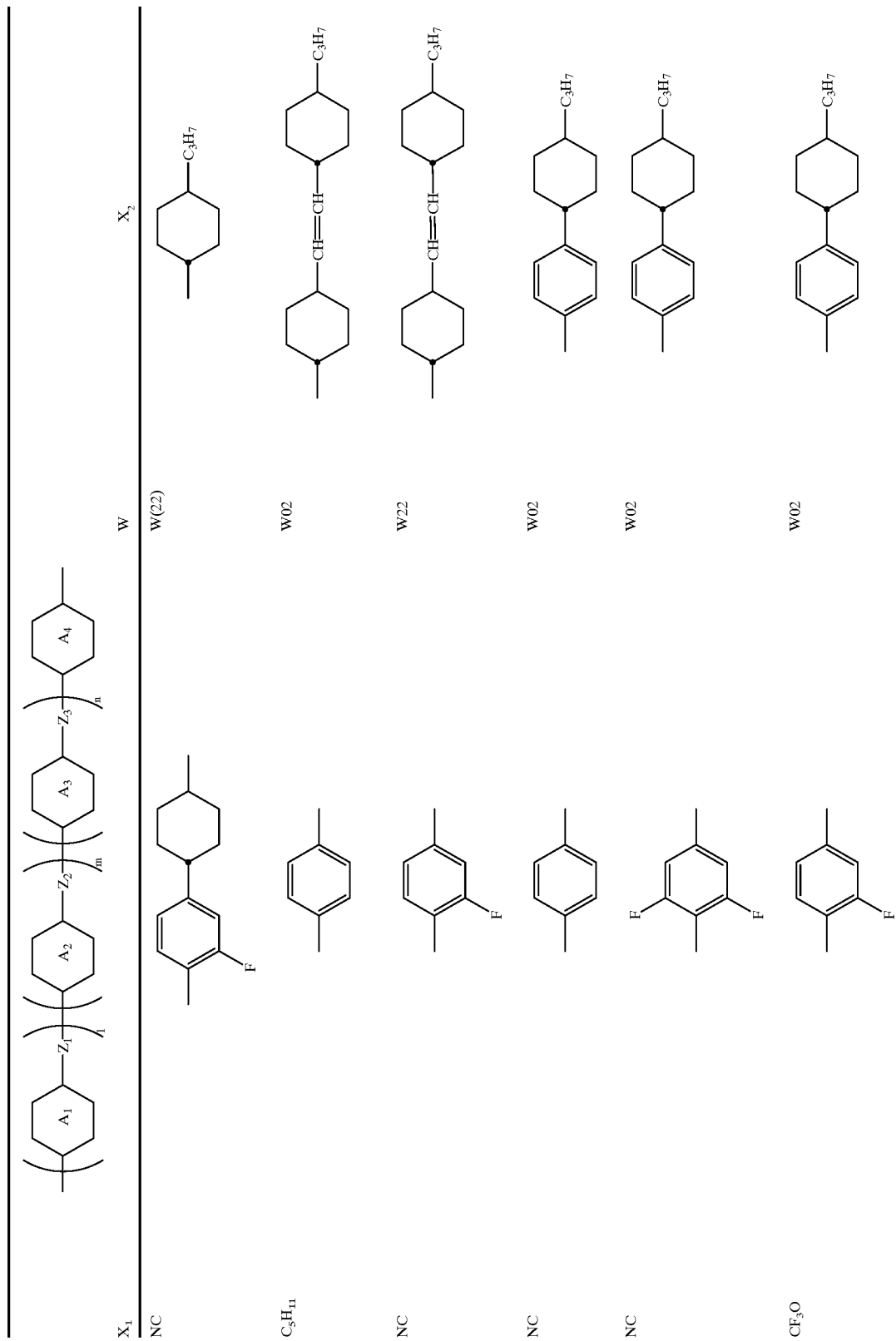

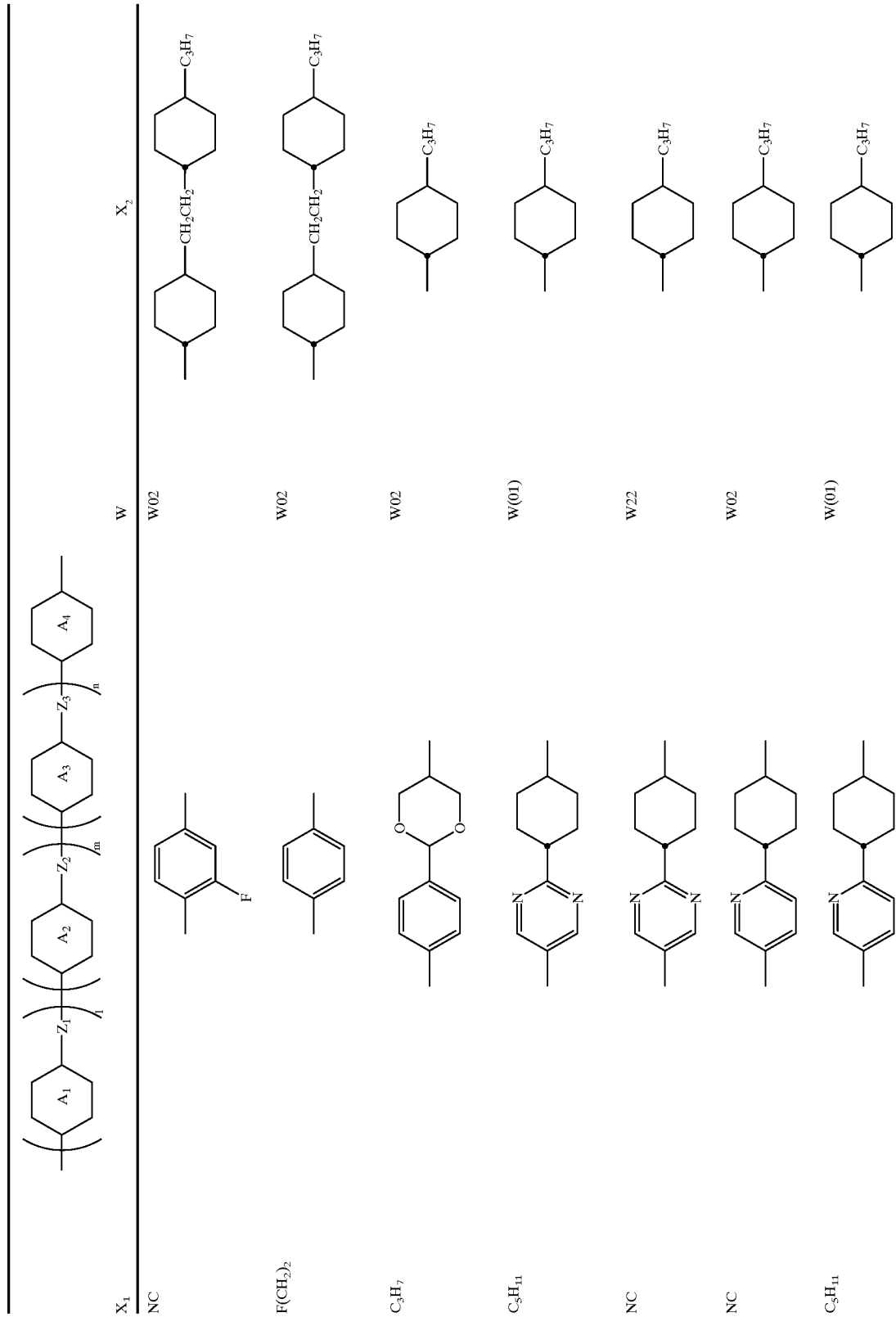

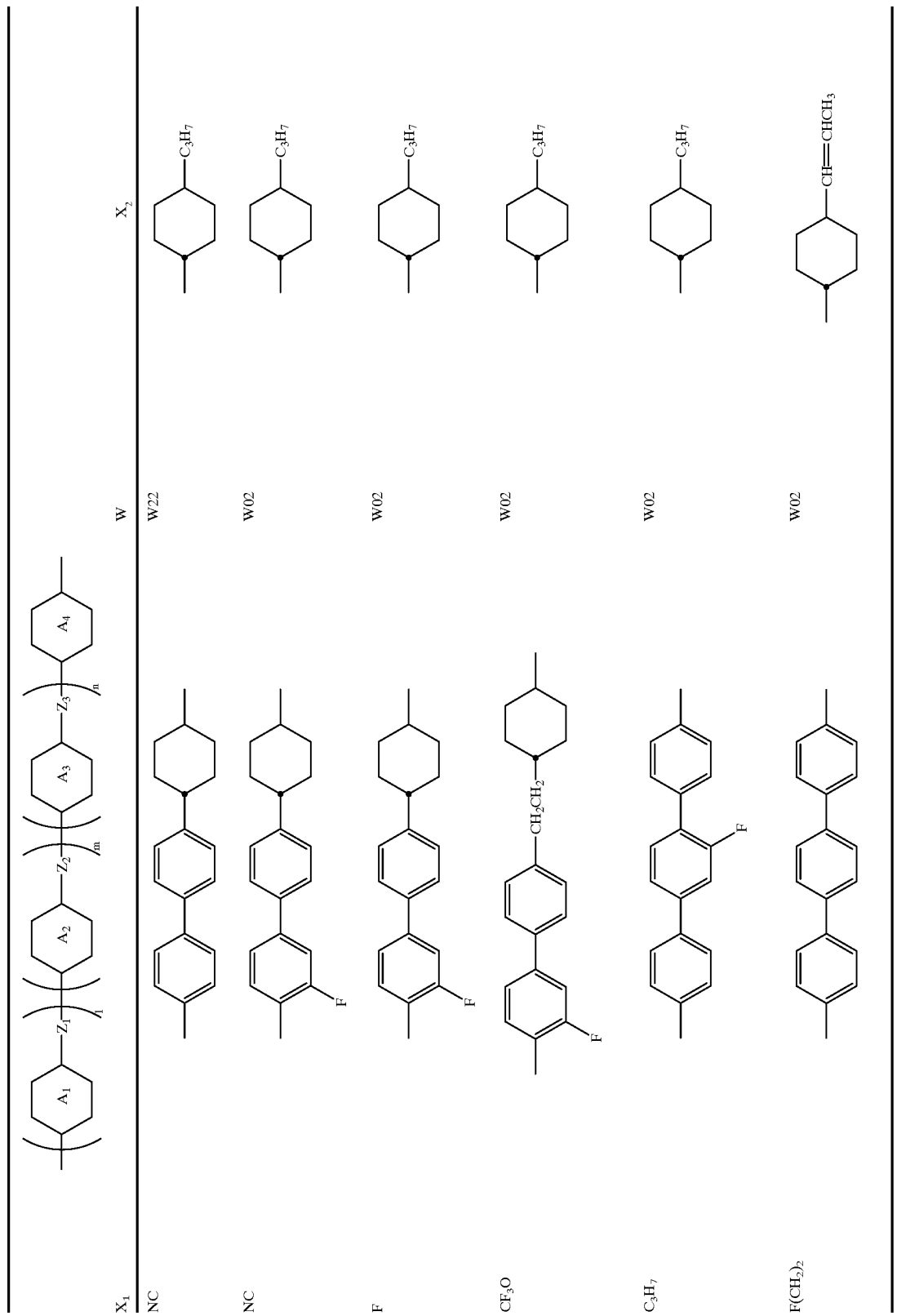

In the above formulas, $W_{01}$–$W_{55}$ have the same meanings as given above.

Example 4 (Use Example 1)

A liquid crystalline composition B1 comprising the following ingredients was prepared.

| | |
|---|---|
| 4-(4-propylcyclohexyl)benzontrile | 24% by weight, |
| 4-(4-pentylcyclohexyl)benzontrile | 36% by weight, |
| 4-(4-heptylcyclohexyl)benzontrile | 25% by weight, and |
| 4-[4-(4-pentylcyclohexyl)phenyl]benzontrile | 24% by weight. |

This composition possesses the following characteristics:
a transparent point: 71.1° C.,
a value of dielectric anisotropy: 11.0,
a value of optical anisotropy: 0.137, and
a viscosity of 26.2 MPa·s.

The liquid crystalline composition B1 was incorporated with 15% by weight of a compound of Example 2 [4'-pentyl-4-(hex-1-en-5-yl)bicyclohexane, a phase transition temperature: SB87.4N110.21)]to prepare a liquid crystalline composition A1 which possesses a transparent point: 77.9° C., a value of dielectric anisotropy: 9.5, a value of optical anisotropy: 0.131, a viscosity: 25.1 mPa·s, and K33/K11=2.11 and shows an increases transparent point and a depressed viscopsity. The composition A1 was allowed to stand in a freezer kept at −20° C. and its state was observed, but neither appearance of smectic phase nor precipitation of crystals were detected.

Comparative Example 1

The liquid crystalline composition B1 prepared in Example 4 (85% by weight) was incorporated with 4'-propyl-4-(3-butenyl)bicyclohexane prepared in accordance with the process disclosed in Japanese Laid-open Patent Appln. No. 61-83136 (15% by weight) to prepare a liquid crystalline composition A2. A ratio of K33/K11 of this composition was 1.78. When this composition was allowed to stand in a freezer kept at 31° C., a smectic phase appeared after 3 days.

As the namatic liquid crystalline composition containing the compound of the general formula (1), the following examples (Use Examples 2–21) can further be shown. The compounds listed in these Use Examples are shown according to the rule of the following Table:

TABLE 1

Table: Method of designating compounds using notations

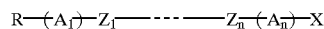

| 1) Left end terminal groups | Notations | 3) Groups connected | Notations |
|---|---|---|---|
| $C_aH_{2a+1}$— | a— | —$CH_2CH_2$— | 2 |
| $C_aH_{2a+1}O$— | aO— | —COO— | E |
| $C_aH_{2a+1}OC_bH_{2b}$— | aOb— | | |
| $CH_2$=$CHC_aH_{2a}$— | Va— | —C≡C— | T |
| $C_aH_{2a+1}CH$=$CHC_bH_{2b}$— | aVb— | —CH=CH— | V |
| $C_aH_{2a+1}CH$=$CHC_bH_{2b}CH$=$CHC_dH_{2d}$— | aVbVc— | —$CF_2O$— | $CF_2O$ |

| 2) Ring structures —(An)— | Notations | 4) Right end terminal groups | Notations |
|---|---|---|---|
| 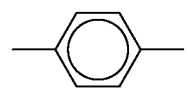 | B | —F | —F |
| 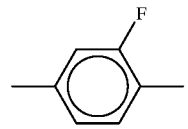 | B(F) | —Cl | —CL |
| 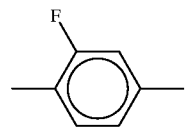 | B(2F) | —CN | —C |
| 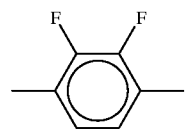 | B(2F,3F) | —$CF_3$ | —CF3 |

TABLE 1-continued
Table: Method of designating compounds using notations
| Structure | Symbol | Z group | X group |
|---|---|---|---|
| (2,6-difluoro phenyl) | B(F,F) | —OCF$_3$ | —OCF3 |
| (2-chloro phenyl) | B(CL) | —OCF$_2$H | —OCF2H |
| cyclohexyl | H | —C$_w$H$_{2w+1}$ | —W |
| pyrimidine | Py | —OC$_2$H$_{2w+1}$ | —OW |
| dioxane | D | —COOCH$_3$ | —EMe |
| cyclohexene | Ch | | |
TABLE 2
5) Example of designation
Example 1
3-H2B(F,F)B(F)-F
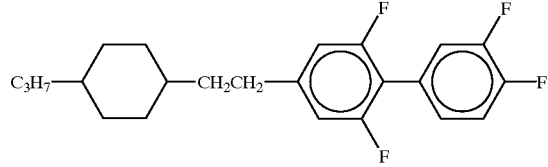
Example 2
3-HB(F)TB-2
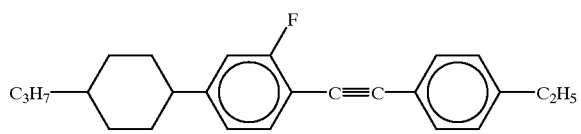

TABLE 2-continued

5) Example of designation

Example 3

1V2-BEB(F,F)-C

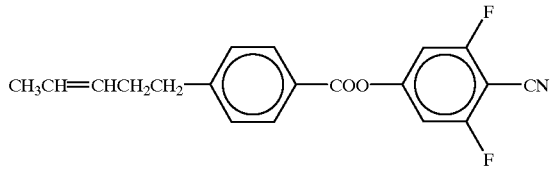

In the above Table, a, b, c, and w are respectively an integer of at least 1. Among the left-end and right-end terminal groups, those not defined in the Table stand for the following groups:

Left-end terminal groups (Notations):

C—: NC— 1V2—: $CH_3$13 CH=CH—$CH_2CH_2$13

V—: $CH_2$=CH—

V2: $CH_2$=CH—$CH_2CH_2$—.

Right-end terminal groups (Notations):

—T1V: —C≡C—$CH_2$—CH=$CH_2$

—V2T: —CH=CH—$CH_2CH_2$—C≡CH

—V2T1: —CH=CH—$CH_2CH_2$—C≡C—$CH_3$

—2V2T: —$CH_2CH_2$—CH=CH—$CH_2CH_2$—C≡CH

The compound with asterisk (*) is a compound of the general formula (1) of the present invention. The notations used for characteristics have the following meanings:

TNI: Nematic-isotropic liquid transition temperature (° C.)

η: Viscosity (mPa·s)

Δn: Optical anisotropy

Δε: Dielectric anisotropy

Vth: Threshold voltage (V).

Example 5 (Use Example 2)

| | |
|---|---|
| *C-BH-T1V | 10.0% |
| 1V2-BEB(F,F)-C | 5.0% |
| 3-HB-C | 15.0% |
| 1-BTB-3 | 5.0% |
| 2-BTB-1 | 10.0% |
| 3-HH-4 | 11.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |

Below are various physical properties of this liquid crystalline composition.

TNI=86.9 (° C.)

η=28.3 (mPa·s)

Δn=0.163

Δε=5.9

Vth=2.30 (V).

Example 6 (Use Example 3)

| | |
|---|---|
| *C-BH-T1V | 6.0% |
| *5-HH-V2T | 4.0% |
| V2-HB-C | 12.0% |
| 1V2-HB-C | 12.0% |
| 3-HB-C | 24.0% |
| 3-HB(F)-C | 5.6% |
| 2-BTB-1 | 2.0% |
| 3-HH-4 | 4.0% |
| 2-HHB-C | 3.0% |
| 3-HHB-C | 6.0% |
| 3-HB(F)TB-2 | 8.0% |
| 3-H2BTB-2 | 5.0% |
| 3-H2BTB-3 | 5.0% |
| 3-H2BTB-4 | 4.0% |

Below are various Physical properties of this liquid crystalline composition.

TNI=88.2 (° C.)

η=25.9 (mPa·s)

Δn=0.161

Δε=9.0

Vth=1.96 (V).

Example 7 (Use Example 4)

| | |
|---|---|
| *5-HH-V2T | 6.0% |
| 2O1-BEB(F)-C | 5.0% |
| 3O1-BEB(F)-C | 15.0% |
| 4O1-BEB(F)-C | 13.0% |
| 5O1-BEB(F)-C | 13.0% |
| 2-HHB(F)-C | 15.0% |
| 3-HHB(F)-C | 15.0% |
| 3-HB(F)TB-2 | 2.0% |
| 3-HB(F)TB-3 | 2.0% |
| 3-HB(F)TB-4 | 2.0% |
| 3-HHB-1 | 8.0% |
| 3-HHB-O1 | 4.0% |

Below are various physical properties of this liquid crystalline composition.

TNI=90.2 (° C.)

η=85.9 (mPa·s)

Δn=0.141

Δε=30.8

Vth=0.86 (V).

Example 8 (Use Example 5)

| Component | Percentage |
|---|---|
| *5-HH-V2T | 5.0% |
| 5-PyB-F | 4.0% |
| 3-PyB(F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-05 | 3.0% |
| 6-PyB-06 | 3.0% |
| 6-PyB-07 | 3.0% |
| 6-PyB-08 | 3.0% |
| 3-PyBB-F | 6.0% |
| 4-PyBB-F | 6.0% |
| 5-PyBB-F | 6.0% |
| 3-HHB-1 | 6.0% |
| 3-HHB-3 | 8.0% |
| 2-H2BTB-2 | 4.0% |
| 2-H2BTB-3 | 2.0% |
| 2-H2BTB-4 | 2.0% |
| 3-H2BTB-2 | 5.0% |
| 3-H2BTB-3 | 5.0% |
| 3-H2BTB-4 | 5.0% |

Below are various physical properties of this liquid crystalline composition.

TNI=93.4 (° C.)

η=34.4 (mPa·s)

Δn=0.195

Δε=6.3

Vth=2.30 (V).

Example 9 (Use Example 6)

| Component | Percentage |
|---|---|
| *C-BH-T1V | 2.0% |
| *5-HH-V2T | 3.0% |
| 3-DB-C | 10.0% |
| 4-DB-C | 10.0% |
| 2-BEB-C | 10.0% |
| 3-BEB-C | 4.0% |
| 3-PyB(F)-F | 6.0% |
| 3-HEB-04 | 5.0% |
| 4-HEB-02 | 6.0% |
| 5-HEB-01 | 6.0% |
| 3-HEB-02 | 5.0% |
| 5-HEB-02 | 4.0% |
| 5-HEB-5 | 5.0% |
| 4-HEB-5 | 5.0% |
| 10-BEB-2 | 4.0% |
| 3-HHB-1 | 6.0% |
| 3-HHEBB-C | 3.0% |
| 3-HBEBB-C | 3.0% |
| 5-HBEBB-C | 3.0% |

Below are various physical properties of this liquid crystalline composition.

TNI=70.3 (° C.)

η=40.5 (mPa·s)

Δn=0.120

Δε=11.0

Vth=1.33 (V).

Example 10 (Use Example 7)

| Component | Percentage |
|---|---|
| *5-HHV2T | 4.0% |
| 3-HB-C | 18.0% |
| 5-HB-C | 3.0% |
| 1O1-HB-C | 10.0% |
| 3-HB(F)-C | 10.0% |
| 2-PyB-2 | 2.0% |
| 3-PyB-2 | 2.0% |
| 4-PyB-2 | 2.0% |
| 101-HH-3 | 7.0% |
| 2-BTB-01 | 7.0% |
| 3-HHB-1 | 7.0% |
| 3-HHB-F | 4.0% |
| 3-HHB-O1 | 4.0% |
| 3-HHB-3 | 4.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |

Below are various physical properties of this liquid crystalline composition.

TNI=79.3 (° C.)

η=18.0 (mPa·s)

Δn=0.139

Δε=8.0

Vth=1.76 (V).

Example 11 (Use Example 8)

| Component | Percentage |
|---|---|
| *5-HH-V2T | 5.0% |
| 201-BEB(F)-C | 5.0% |
| 301-BEB(F)-C | 12.0% |
| 501-BEB(F)-C | 4.0% |
| 1V2-BEB(F,F)-C | 10.0% |
| 3-HH-EMe | 10.0% |
| 3-HB-O2 | 18.0% |
| 3-HHEB | 3.0% |
| 5-HHEB-F | 3.0% |
| 3-HBEB-F | 4.0% |
| 201-HBEB(F)-C | 2.0% |
| 3-HBEB(F,F)-C | 4.0% |
| 3-HHB-F | 4.0% |
| 3-HHB-O1 | 4.0% |
| 3-HHB-3 | 8.0% |
| 3-HEBEB-F | 2.0% |
| 3-HEBEBN-1 | 2.0% |

Below are various physical properties of this liquid crystalline composition.

TNI=75.5 (° C.)

η=35.3 (mPa·s)

Δn=0.114

Δε=23.4

Vth=0.99 (V).

Example 12 (Use Example 9)

| Component | Percentage |
|---|---|
| *C-BHT1V | 3.0% |
| *5-HH-V2T | 5.0% |
| 5-BEB(F)-C | 5.0% |
| V-HB-C | 8.0% |
| 5-PyB-C | 6.0% |
| 4-BB-3 | 11.0% |
| 3-HH-2V | 10.0% |
| 5-HH-V | 11.0% |

-continued

| | |
|---|---|
| V-HHB-1 | 7.0% |
| V2-HHB-1 | 15.0% |
| 3-HHB-1 | 4.0% |
| 1V2-HHB-2 | 10.0% |
| 3-HHEBH-3 | 5.0% |

Below are various physical properties of this liquid crystalline composition.

TNI=89.0 (° C.)

$\eta$=18.3 (mPa·s)

$\Delta$n=0.114

$\Delta\epsilon$=4.4

Vth=2.46 (V).

Example 13 (Use Example 10)

| | |
|---|---|
| *5-HH-V2T | 3.0% |
| *2-BEB-C | 12.0% |
| 3-BEB-C | 4.0% |
| 4-BEB-C | 6.0% |
| 3-HB-C | 28.0% |
| 3-HEB-04 | 12.0% |
| 4-HEB-02 | 8.0% |
| 5-HEB-01 | 8.0% |
| 3-HEB-02 | 6.0% |
| 5-HEB-02 | 5.0% |
| 3-HHB-1 | 4.0% |
| 3-HHB-01 | 4.0% |

Below are various physical properties of this liquid crystalline composition.

TNI=61.6 (° C.)

$\eta$=25.7 (mPa·s)

$\Delta$n=0.112

$\Delta\epsilon$=9.7

Vth=1.37 (V).

Example 14 (Use Example 11)

| | |
|---|---|
| *5-HH-V2T | 4.0% |
| 7-HB(F)-F | 5.0% |
| 5-H2B(F)-F | 5.0% |
| 3-HH-4 | 5.0% |
| 3-HB-02 | 10.0% |
| 2-HHB(F)-F | 10.0% |
| 3-HHB(F)-F | 10.0% |
| 5-HHB(F)-F | 10.0% |
| 3-H2HB(F)-F | 5.0% |
| 2-HBB(F)-F | 3.0% |
| 3-HBB(F)-F | 3.0% |
| 5-HBB(F)-F | 6.0% |
| 2-H2BB(F)-F | 5.0% |
| 3-H2BB(F)-F | 6.0% |
| 3-HHB-1 | 4.0% |
| 3-HHB-01 | 5.0% |
| 3-HHB-3 | 4.0% |

Below are various physical properties of this liquid crystalline composition.

TNI=87.2 (° C.)

$\eta$=18.4 (mPa·s)

$\Delta$n=0.092

$\Delta\epsilon$=3.1

Vth=2.73 (V).

Example 15 (Use Example 12)

| | |
|---|---|
| *5-HH-V2T | 4.0% |
| 7-HB(F,F)-F | 3.0% |
| 3-HB-02 | 7.0% |
| 2-HHB(F)-F | 10.0% |
| 3-HHB(F)-F | 10.0% |
| 5-HHB(F)-F | 10.0% |
| 2-HBB(F)-F | 9.0% |
| 3-HBB(F)-F | 9.0% |
| 5-HBB(F)-F | 16.0% |
| 3-HBB-F | 4.0% |
| 5-HBB-F | 3.0% |
| 3-HBB(F,F)-F | 5.0% |
| 5-HBB(F,F)-F | 10.0% |

Below are various physical properties of this liquid crystalline composition.

TNI=86.9 (° C.)

$\eta$=24.7 (mPa·s)

$\Delta$n=0.114

$\Delta\epsilon$=5.7

Vth=2.01 (V).

Example 16 (Use Example 13)

| | |
|---|---|
| *5-HH-V2T | 7.0% |
| 7-HB(F,F)-F | 4.0% |
| 3-H2HB(F,F)-F | 12.0% |
| 4-H2H8(F,F)-F | 10.0% |
| 5-H2HB(F,F)-F | 10.0% |
| 3-HHB(F,F)-F | 5.0% |
| 4-HHB(F,F)-F | 3.0% |
| 3-HH2B(F,F)-F | 15.0% |
| 5-HH2B(F,F)-F | 10.0% |
| 3-HBB(F,F)-F | 12.0% |
| 5-HBB(F,F)-F | 12.0% |

Below are various physical properties of this liquid crystalline composition.

TNI=75.9 (° C.)

$\eta$=26.8 (mPa·s)

$\Delta$n=0.087

$\Delta\epsilon$=8.0

Vth=1.64 (V).

Example 17 (Use Example 4)

| | |
|---|---|
| *5-HHV2T | 4.0% |
| 3-HB-CL | 10.0% |
| 5-HB-CL | 4.0% |
| 7-HB-CL | 4.0% |
| 101-HH-5 | 5.0% |
| 2-HBB(F)-F | 8.0% |
| 3-HBB(F)-F | 8.0% |
| 5-HBB(F)-F | 14.0% |
| 4-HHB-CL | 8.0% |
| 5-HBB-CL | 8.0% |
| 3-H2HB(F)-CL | 4.0% |
| 3-HBB(F,F)-F | 10.0% |
| 5-H2BB(F,F)-F | 9.0% |
| 3-HB(F)VB-2 | 2.0% |
| 3-HB(F)VB-3 | 2.0% |

Below are various physical properties of this liquid crystalline composition.

TNI=89.3 (° C.)

η=20.3 (mPa·s)

Δn=0.123

Δε=4.7

Vth=2.37 (V).

Example 18 (Use Example 15)

| | |
|---|---|
| *5-HH-V2T | 5.0% |
| 3-HHB(F,F)-F | 6.0% |
| 3-H2H8(F,F)-F | 8.0% |
| 4-H2H8(F,F)-F | 8.0% |
| 5-H2H8(F,F)-F | 8.0% |
| 3-HBB(F,F)-F | 21.0% |
| 5-HBB(F,F)-F | 20.0% |
| 3-H2BB(F,F)-F | 10.0% |
| 5-HHBB(F,F)-F | 3.0% |
| 3-HH2BB(F,F)-F | 2.0% |
| 5-HHEBB-F | 3.0% |
| 101-HBBH-F | 3.0% |
| 101-HBBH-4 | 2.0% |
| 101-HBBH-5 | 4.0% |

Below are various physical properties of this liquid crystalline composition.

TNI=96.4 (° C.)

η=33.6 (mPa·s)

Δn=0.115

Δε=8.6

Vth=1.80 (V).

Example 19 (Use Example 16)

| | |
|---|---|
| *5-HH-V2T | 5.0% |
| 5-HB-F | 12.0% |
| 6-HB-F | 9.0% |
| 7-HB-F | 7.0% |
| 2-HHB-OCF3 | 7.0% |
| 3-HHB-OCF3 | 6.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB(F,F)-F | 5.0% |
| 3-HBB(F)-F | 10.0% |
| 5-HBB(F)-F | 10.0% |
| 3-HH2B(F)-F | 3.0% |
| 3-HB(F)BH-3 | 3.0% |
| 5-HBBH-3 | 3.0% |

Below are various physical properties of this liquid crystalline composition.

TNI=87.0 (° C.)

η=14.7 (mPa·s)

Δn=0.092

Δε=4.3

Vth=2.46 (V).

Example 20 (Use Example 17)

| | |
|---|---|
| *5-HH-V2T | 5.0% |
| 5-HB-CL | 20.0% |
| 3-HB-02 | 6.0% |
| 3-HH-4 | 4.0% |
| 3-HHB-1 | 4.0% |
| 3-HHB(F,F)-F | 8.0% |
| 3-HBB(F,F)-F | 11.0% |
| 5-HBB(F,F)-F | 11.0% |
| 3-HHEB(F,F)-F | 10.0% |
| 4-HHEB(F,F)-F | 3.0% |
| 5-HHEB((F,F)-F | 3.0% |
| 2-HBEB(F,F)-F | 3.0% |
| 3-HBEB(F,F)-F | 3.0% |
| 5-HBEB(F,F)-F | 3.0% |
| 3-HHEBB-F | 3.0% |
| 5-HHEBB-F | 3.0% |

Below are various physical properties of this liquid crystalline composition.

TNI=77.6 (° C.)

η=20.2 (mPa·s)

Δn=0.098

Δε=7.1

Vth=1.73 (V).

Example 21 (Use Example 18)

| | |
|---|---|
| *3-HH-V2T1 | 5.0% |
| *3-BHH-V2T1 | 4.0% |
| 201-BEB-(F)-C | 5.0% |
| 301-BEB(F)-C | 12.0% |
| 501-BEB(F)-C | 4.0% |
| 1V2-BEB(F,F)-C | 16.0% |
| 3-HB-02 | 5.0% |
| 3-HH-4 | 3.0% |
| 3-HHB-F | 3.0% |
| 3-HHB-1 | 4.0% |
| 3-HHB-01 | 4.0% |
| 3-HBEB-F | 4.0% |
| 3-HHEB-F | 5.0% |
| 5-HHEB-F | 7.0% |
| 7-HEB-F | 2.0% |
| 3-H2BTB-2 | 4.0% |
| 3-H2BTB-3 | 4.0% |
| 3-H2BTB-4 | 4.0% |
| 3-HB(F)TB-2 | 5.0%. |

Example 22 (Use Example 19)

| | |
|---|---|
| *3-HVHH-2V2T | 3.0% |
| *3-HV2TH-5 | 3.0% |
| 2-BEB-C | 10.0% |
| 5-BB-C | 12.0% |
| 7-BB-C | 7.0% |
| 1-BTB-3 | 7.0% |
| 2-BTB-1 | 10.0% |
| 10-BEB-2 | 10.0% |
| 10-BEB-5 | 12.0% |
| 2-HHB-1 | 4.0% |
| 3-HHB-F | 4.0% |
| 3-HHB-1 | 7.0% |
| 3-HHB-01 | 4.0% |
| 3-HHB-3 | 7.0% |

Example 23 (Use Example 20)

| | |
|---|---|
| *3-HH-V2T1 | 5.0% |
| *3-HVHH-2V2T | 5.0% |
| 2-HHB(F)-F | 15.0% |
| 3-HHB(F)-F | 15.0% |
| 5-HHB(F)-F | 15.0% |
| 2-H2HB(F)-F | 9.0% |
| 3-H2HB(F)-F | 4.5% |
| 5-H2HB(F)-F | 9.0% |
| 2-HBB(F)-F | 5.6% |
| 3-HBB(F)-F | 5.6% |
| 5-HBB(F)-F | 11.3% |

Example 24 (Use Example 21)

| | |
|---|---|
| *3-BHH-V2T1 | 6.0% |
| *3-HV2TH-5 | 4.0% |
| 2-HHB(F)-F | 2.0% |
| 3-HHB(F)-F | 2.0% |
| 5-HHB(F)-F | 2.0% |
| 2-HBB(F)-F | 5.0% |
| 3-HBB(F)-F | 5.0% |
| 5-HBB(F)-F | 10.0% |
| 2-H2BB(F)-F | 8.0% |
| 3-H2BB(F)-F | 8.0% |
| 3-HBB(F,F)-F | 24.0% |
| 5-HBB(F,F)-F | 16.0% |
| 101-HBBH-4 | 4.0% |
| 101-HBBH-5 | 4.0% |

The present invention indeed exhibits outstanding technical effects, particularly in that it provides novel liquid crystalline compounds and novel liquid crystalline compositions comprising at least one of the novel liquid crystalline compounds which are suitable as a material for electroptical display elements. The liquid crystalline compounds of the present invention are distinguished by their characteristics of steep threshold voltage, an adequate magnitude of values in optical or dielectric anisotropy, an extremely high ratio of elastic constants and low viscosity in addition to good compatibility with other liquid crystalline compounds. As compared with the known conventional alkenyl compounds (a typical example of the conventional compounds known to have a high ratio of K33/K11) in Examples 4 and 5, the liquid crystalline compounds of the present invention exhibit an extremely high ratio of K33/K11. In addition, It is noteworthy that the liquid crystalline compounds of the present invention are indeed especially remarkable in compatibility with other novel or conventional liquid crystalline compounds.

It is understood that the preceding representative examples may be varied within the scope of the present specification both as to ingredients and reaction conditions, by those skilled in the art to achieve essentially the same effects.

As many widely different embodiments of the present invention may be made without departing from the spirit and scope thereof, it is to be construed that the invention is not limited to the specific embodiments thereof except as defined in the appended claims.

What is claimed is:

1. A liquid crystalline compound of the general formula:

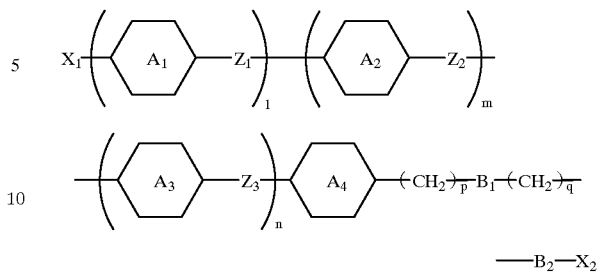

wherein $X_1$ stands for a hydrogen atom, a cyano group, a halogen atom, or an alkyl group with 1–20 carbon atoms, and one or more methylene groups in the alkyl group may be replaced by —CH=CH—, —C≡C—, or oxygen atoms and one or more hydrogen atoms may be substituted by halogen atoms;

$X_2$ stands for a hydrogen atom, an alkyl group with 1–10 carbon atoms, or a substituent of —$(A_5$—$Z_4)_s$—$A_6$—$X_3$; l, m, n and s each stands for an integer of 0 or 1, p, stands for an integer of 0–5; $X_3$ for an alkyl group with 1–10 carbon atoms; $Z_1$–$Z_4$ each independently stands for a covalent bond or an alkylene group with 1–5 carbon atoms, and one or more methylene groups in the alkylene group may be replaced by —CH=CH—, —C≡C—, or an oxygen atom and one or more hydrogen atoms in the alkylene group may be substituted by halogen atoms; the rings $A_1$–$A_6$ each independently stands for a 1,4-phenylene, a 1,4-cyclohexenylene, or a trans-1,4-cyclohexylene, and the carbon atoms in the ring may be replaced by nitrogen atoms or oxygen atoms and the hydrogen atoms in the ring may be substituted by halogen atoms or cyano groups; and $B_1$ and $B_2$ each independently stands for —CH=CH— or —C≡C—, with the proviso that both of $B_1$ and $B_2$ should not be —CH=CH— at the same time.

2. A liquid crystalline compound according to claim 1, wherein $X_1$ stands for an alkyl group, an alkenyl group, an alkoxymethyl group, a halogen atom, or a cyano group.

3. A liquid crystalline compound according to claim 2, wherein $X_2$ stands for a hydrogen atom or an alkyl group with 1–10 carbon atoms.

4. A liquid crystalline compound according to claim 2, wherein $X_2$ stands for a substituent of —$(A_5$—$Z_4)_s$—$A_6$—$X_3$ wherein $A_5$, $Z_4$, $A_6$, and $X_3$ have the same meanings as given above.

5. A liquid crystalline composition which comprises at least one of the liquid crystalline compounds as claimed in claim 1–4.

6. A liquid crystalline composition which comprises at least one liquid crystalline compound as claimed in any of the claims 1–4 as a first component and at least one liquid crystalline compound selected from the group consisting of the general formulas (2), (3), and (4):

(2)

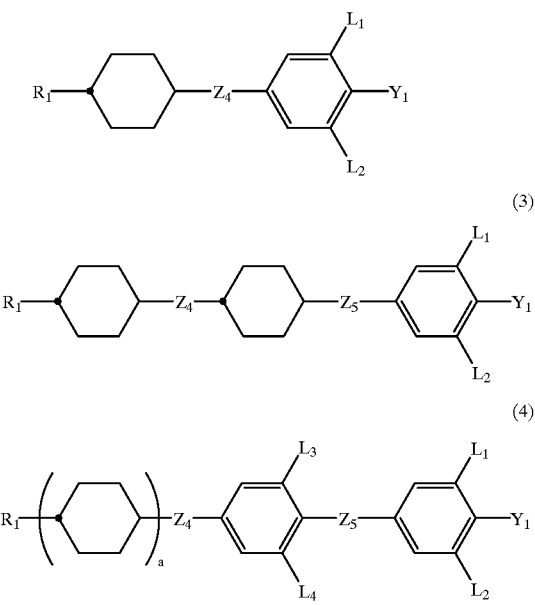

(3)

(4)

wherein $R_1$ stands for an alkyl group with 1–10 carbon atoms; $Y_1$ stands for a fluorine atom, a chlorine atom, —$OCF_3$, —$OCF_2H$, —$CF_3$, —$CF_2H$, or —$CFH_2$; $L_1, L_2, L_3$ and $L_4$ each independently stands for a hydrogen atom or a fluorine atom; $Z_4$ and $Z_5$ each independently stands for —$CH_2CH_2$—, —CH=CH—, or a covalent bond; and a stands for an integer of 1 or 2, as a second component.

7. A liquid crystalline composition which comprises at least one liquid crystalline compound claimed in any one of the claims 1–4 as a first component and at least one liquid crystalline compound selected from the group consisting of the following general formulas (5), (6), (7), (8), (9):

(5)

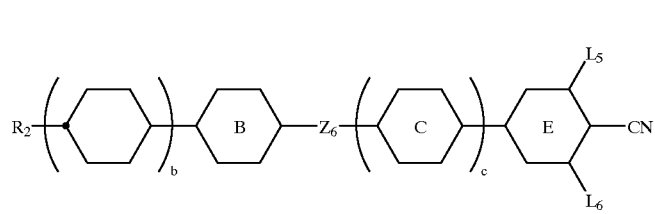

wherein $R_2$ stands for a fluorine atom, and an alkyl group with 1–10 carbon atoms, or an alkenyl group with 2–10 carbon atoms, and one or more methylene groups in those groups may be replaced by oxygen atoms with the proviso that plural consecutive methylene groups are not replaced by oxygen atoms; the ring B stands for a trans-1,4-cyclohexylene, a 1,4-phenylene, or a trans-1,3-dioxan-2,5-diyl; the ring C stands for a trans-1,4-cyclohexylene, a 1,4-phenylene, or a pyrimidin-2,5-diyl; the ring E stands for a tans-1,4-cyclohexylene, or a 1,4-phenylene group; $Z_6$ stands for —$CH_2CH_2$—, —$CO_2$, or a covalent bond; $L_5$ and $L_6$ each independently stands for a hydrogen atom or a fluorine atom; and b and c each independently stands for an integer of 0 or 1, (6)

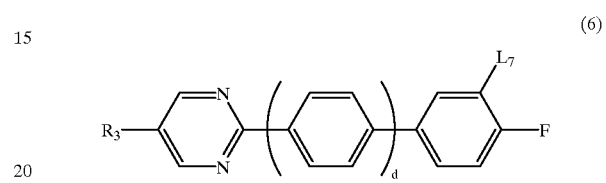

wherein $R_3$ stands for an alkyl group with 1–10 carbon atoms; $L_7$ stands for a hydrogen atom or a fluorine atom; and d stands for an integer of 0 or 1, (7)

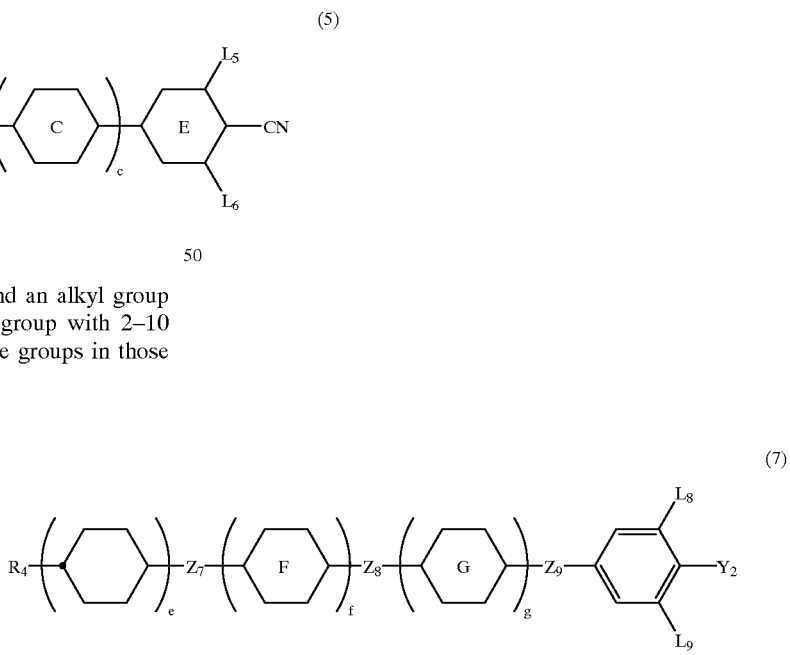

wherein $R_4$ stands for an alkyl group with 1–10 carbon atoms; the rings F and G each independently stands for a trans-1,4-cyclohexylene or a 1,4-phenylene; $Z_7$ and $Z_8$ each independently stands for —$CO_2$— or a covalent bond; $Z_9$ stands for —$CO_2$— or —C≡C—; $L_8$ and $L_9$ each independently stands for a hydrogen atom or fluorine atom; $Y_2$ stands for a fluorine atom, —$OCF_2H$, —$CF_3$, —$CF_2H$, or —$CFH_2$; and e, f and g each independently stands for an integer of 0 or 1,

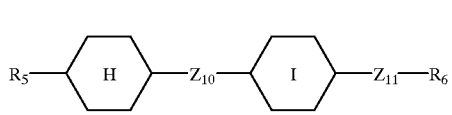

(8)

wherein $R_5$ and $R_6$ each independently stands for an alkyl group with 1–10 carbon atoms or an alkenyl group with 2–10 carbon atoms, one or more methylene groups in those groups may be replaced by oxygen atoms with the proviso that plural consecutive methylene groups are not replaced by oxygen atoms; the ring H stands for a trans-1,4-cyclohexylene, a 1,4-phenylene, or pyrimidin-2,5-diyl; the ring I stands for a trans-1,4-cyclohexylene or a 1,4-phenylene; $Z_{10}$ stands for —C≡C—, —$CO_2$—, —$CH_2$—$CH_2$—, —CH=CH—C≡C—, or a covalent bond; and $Z_{11}$ stands for —$CO_2$— or a covalent bond,

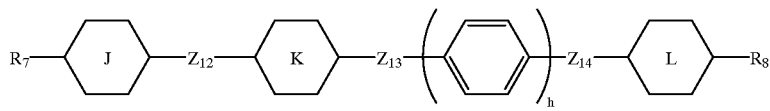

(9)

wherein $R_7$ and $R_8$ each independently stands for an alkyl group with 1–10 carbon atoms or an alkenyl group with 2–10 carbon atoms, one or more methylene groups in those groups may be replaced by an oxygen atom, with the proviso that plural consecutive methylene groups are not replaced by oxygen atoms; the ring J stands for a trans-1,4-cyclohexylene, a 1,4-phenylene, or a pyrimidin-2,5-diyl; the ring K stands for a trans-1,4-cyclohexylene, a 1,4-phenylene, in which one or more hydrogen atoms on the 1,4-phenylene ring may be substituted by one or more fluorine atoms, or a pyrimidin-2,5-diyl; the ring L stands for a trans-1,4-cyclohexylene or a 1,4-phenylene; $Z_{12}$ and $Z_{13}$ each independently stands for —$CO_2$—, —$CH_2CH_2$— or a covalent bond; $Z_{14}$ stands for —CH=CH—, —C≡C—, —$CO_2$— or a covalent bond; and h stands for an integer of 0 or 1, as a second component.

8. A liquid crystal display element containing the liquid crystalline composition as claimed in claim 5.

9. A liquid crystal display element containing the liquid crystalline composition as claimed in claim 6.

10. A liquid crystal display element containing the liquid crystalline composition as claimed in claim 7.

11. A liquid crystalline composition which comprises at least one liquid crystalline compound as claimed in any one of the claims 1–4 as a first component, at least one liquid crystalline compound selected from the group consisting of the general formulas (2), (3), and (4) as a part of a second component, and at least one liquid crystalline compound selected from the group consisting of the general formulas (5), (6), (7), (8), and (9) as the other part of the second component:

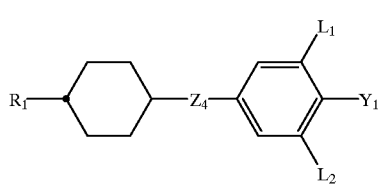

-continued (3)

(4)

wherein $R_1$ stands for an alkyl group with 1–10 carbon atoms; $Y_1$ stands for a fluorine atom, a chlorine atom, —$OCF_3$, —$OCF_2H$, —$CF_3$, —$CF_2H$, or —$CFH_2$; $L_1$, $L_2$, $L_3$ and $L_4$ each independently stands for a hydrogen atom or a fluorine atom; $Z_4$ and $Z_5$ each independently stands for —$CH_2CH_2$—, —CH=CH—, or a covalent bond; and a stands for an integer of 1 or 2,

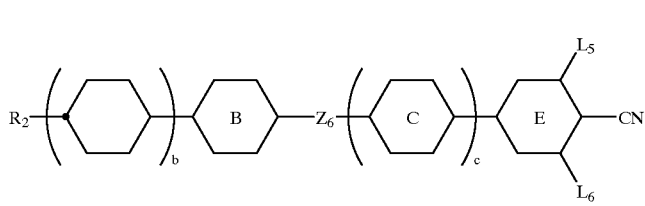

wherein $R_2$ stands for a fluorine atom, and an alkyl group with 1–10 carbon atoms, or an alkenyl group with 2–10 carbon atoms, and one or more methylene groups in those groups may be replaced by oxygen atoms with the proviso that plural consecutive methylene groups are not replaced by oxygen atoms; the ring B stands for a trans-1,4-cyclohexylene, a 1,4-phenylene, or a trans-1,3-dioxan-2,5-diyl; the ring C stands for a trans-1,4-cyclohexylene, a 1,4-phenylene, or a pyrimidin-2,5-diyl; the ring E stands for a tans-1,4-cyclohexylene, or a 1,4-phenylene group; $Z_6$ stands for —$CH_2CH_2$—, —$CO_2$, or a covalent bond; $L_5$ and $L_6$ each independently stands for a hydrogen atom or a fluorine atom; and b and c each independently stands for an integer of 0 or 1,

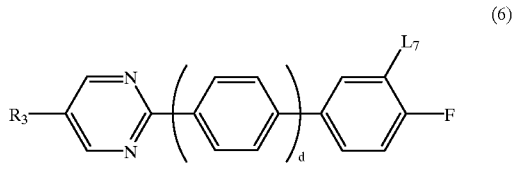

wherein $R_3$ stands for an alkyl group with 1–10 carbon atoms; $L_7$ stands for a hydrogen atom or a fluorine atom; and d stands for an integer of 0 or 1,

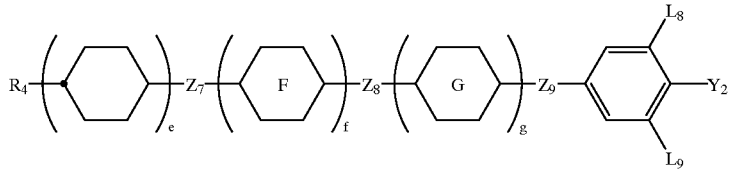

wherein $R_4$ stands for an alkyl group with 1–10 carbon atoms; the rings F and G each independently stands for a trans-1,4-cyclohexylene or a 1,4-phenylene; $Z_7$ and $Z_8$ each independently stands for —$CO_2$— or a covalent bond; $Z_9$ stands for —$CO_2$— or —C≡C—; $L_8$ and $L_9$ each independently stands for a hydrogen atom or fluorine atom; $Y_2$ stands for a fluorine atom, —$OCF_2H$, —$CF_3$, —$CF_2H$, or —$CFH_2$; and e, f and g each independently stands for an integer of 0 or 1,

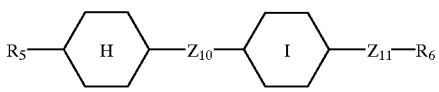

wherein $R_5$ and $R_6$ each independently stands for an alkyl group with 1–10 carbon atoms or an alkenyl group with 2–10 carbon atoms, one or more methylene groups in those groups may be replaced by oxygen atoms with the proviso that plural consecutive methylene groups are not replaced by oxygen atoms; the ring H stands for a trans-1,4-cyclohexylene, a 1,4-phenylene, or pyrimidin-2,5-diyl; the ring I stands for a trans-1,4-cyclohexylene or a 1,4-phenylene; $Z_{10}$ stands for —C≡C—, —$CO_2$—, —$CH_2$—$CH_2$—, —CH=CH—C≡C—, or a covalent bond; and $Z_{11}$ stands for —$CO_2$— or a covalent bond,

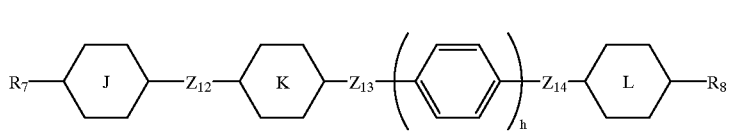

wherein $R_7$ and $R_8$ each independently stands for an alkyl group with 1–10 carbon atoms or an alkenyl group with 2–10 carbon atoms, one or more methylene groups in those groups may be replaced by an oxygen atom, with the proviso that plural consecutive methylene groups are not replaced by oxygen atoms; the ring J stands for a trans-1,4-cyclohexylene, a 1,4-phenylene, or a pyrimidin-2,5-diyl; the ring K stands for a trans-1,4-cyclohexylene, a 1,4-phenylene, in which one or more hydrogen atoms on the 1,4-phenylene ring may be substituted by one or more fluorine atoms, or a pyrimidin-2,5-diyl; the ring L stands for a trans-1,4-cyclohexylene or a 1,4-phenylene; $Z_{12}$ and $Z_{13}$ each independently stands for —$CO_2$—, —$CH_2CH_2$— or a covalent bond; $Z_{14}$ stands for —CH=CH—, —C≡C—, —$CO_2$— or a covalent bond; and h stands for an integer of 0 or 1.

12. A liquid crystal display element containing the liquid crystalline composition as claimed in claim 11.

* * * * *

UNITED STATES PATENT AND TRADEMARK OFFICE
CERTIFICATE OF CORRECTION

PATENT NO. : 6,015,508
DATED : January 18, 2000
INVENTOR(S) : Noriyuki Ohnishi et al.

Page 1 of 1

It is certified that error appears in the above-identified patent and that said Letters Patent is hereby corrected as shown below:

Abstract,
Line 4, below the formulas, change "-≡C-" to -- -C≡C- --;
Line 7, below the formulas, change "-($A_4$-" to -- -($A_5$- --.

Claim 1, column 116,
Line 19, change "-CH≡CH-" to -- -CH=CH- --;
Line 26, after "p" delete the comma, and change "$X_3$" to -- q stands for an integer of 1-5; $X_3$ stands --.

Claim 7, column 117,
Line 52, after "atom," delete "and";

Claim 7, column 118,
Line 7, change "tans" to -- trans --;
Line 8, change "-$CO_2$" to -- -$CO_2$- --.

Claim 11, column 121,
Line 21, change "tans" to -- trans --;
Line 22, change "-$CO_2$" to -- -$CO_2$- --.

Signed and Sealed this

Second Day of October, 2001

Attest:

NICHOLAS P. GODICI
Attesting Officer   Acting Director of the United States Patent and Trademark Office